US009573950B2

(12) United States Patent
Backfisch et al.

(10) Patent No.: US 9,573,950 B2
(45) Date of Patent: Feb. 21, 2017

(54) SUBSTITUTED [1,4]DIAZEPINO[6,7,1-IJ]QUINOLINES AS SEROTONIN 5-HT2C RECEPTOR MODULATORS

(71) Applicant: AbbVie Deutschland GmbH & Co. KG, Wiesbaden (DE)

(72) Inventors: Gisela Backfisch, Ludwigshafen (DE); Margaretha Henrica Maria Bakker, Ludwigshafen (DE); Günter Blaich, Ludwigshafen (DE); Wilfried Braje, Ludwigshafen (DE); Karla Drescher, Ludwigshafen (DE); Thomas Erhard, Ludwigshafen (DE); Andreas Haupt, Ludwigshafen (DE); Hannes Koolman, North Chicago, IL (US); Viktor Lakics, Ludwigshafen (DE); Anna Linsenmeier, Ludwigshafen (DE); Helmut Mack, Ludwigshafen (DE); Raimund Peter, Wilmslow (GB); Ana Lucia Relo, Ludwigshafen (DE); Xiaona Zhao, Tianjin (CN); Jincheng Wang, Tianjin (CN)

(73) Assignee: AbbVie Deutschland GmbH & Co KG, Wiesbaden (DE)

( * ) Notice: Subject to any disclaimer, the term of this patent is extended or adjusted under 35 U.S.C. 154(b) by 0 days.

(21) Appl. No.: 14/657,840

(22) Filed: Mar. 13, 2015

(65) Prior Publication Data
US 2015/0259343 A1 Sep. 17, 2015

Related U.S. Application Data

(60) Provisional application No. 61/953,424, filed on Mar. 14, 2014.

(51) Int. Cl.
*A61K 31/551* (2006.01)
*C07D 487/16* (2006.01)
*C07D 471/06* (2006.01)
*C07D 471/04* (2006.01)

(52) U.S. Cl.
CPC ........... *C07D 471/06* (2013.01); *C07D 471/04* (2013.01)

(58) Field of Classification Search
CPC .............................. A61K 31/551; C07D 487/16
USPC .......... 514/220; 540/559; 549/356, 429, 510
See application file for complete search history.

(56) References Cited

U.S. PATENT DOCUMENTS

2007/0225274 A1 9/2007 Jacobson
2007/0225277 A1 9/2007 Rosenzweig-Lipson
2008/0146583 A1 6/2008 McMurray et al.

FOREIGN PATENT DOCUMENTS

WO          03091250 A1   11/2003
WO       2014041131 A1    3/2014
WO    WO 2015/136090   *  9/2015

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Jordan, V. C. Nature Reviews: Drug Discovery, 2, 2003, 205.*
Hackam, et al. JAMA, 296(14), 2006, 1731-1732.*
Sharif N.A., et al., "AL-34662: A Potent, Selective, and Efficacious Ocular Hypotensive Serotonin-2 Receptor Agonist," Journal of Ocular Pharmacology and Therapeutics, 2007, vol. 23 (1), pp. 1-13.
Shen J.H., et al., "A 6-Week Randomized, Double-Blind, Placebo-Controlled, Comparator Referenced Trial of Vabicaserin in Acute Schizophrenia," Journal of Psychiatric Research, 2014, vol. 53, pp. 14-22.
Shimada I., et al., "Synthesis and Structure-Activity Relationships of a Series of Benzazepine Derivatives as 5-HT2C Receptor Agonists," Bioorganic & Medicinal Chemistry, 2008, vol. 16 (6), pp. 3309-3320.
Siuciak J.A., et al., "CP-809,101, A Selective 5-HT2C Agonist, Shows Activity in Animal Models of Antipsychotic Activity," Neuropharmacology, 2007, vol. 52 (2), pp. 279-290.
Smith B.M., et al., "Discovery and Structure-Activity Relationship of (1R)-8-Chloro-2,3,4,5-Tetrahydro-1-Methyl-1H-3-Benzazepine (Lorcaserin), A Selective Serotonin 5-HT2C Receptor Agonist for the Treatment of Obesity," Journal of Medicinal Chemistry, 2008, vol. 51 (2), pp. 305-313.
Tecott L.H., et al., "Eating Disorder and Epilepsy in Mice Lacking 5-HT2C Serotonin Receptors," Nature, 1995, vol. 374 (6522), pp. 542-546.
Thomsen W.J., et al., "Lorcaserin, A Novel Selective Human 5-Hydroxytryptamine2C Agonist: In Vitro and In Vivo Pharmacological Characterization," The Journal of Pharmacology and Experimental Therapeutics, 2008, vol. 325 (2), pp. 577-587.
Thorslund K., et al., "Serotonergic Drugs a Possible Role in the Treatment of Psoriasis," Drug News & Perspectives, 2007, vol. 20 (8), pp. 521-525.
Weinberger D.R., et al., "Prefrontal Function in Schizophrenia: Confounds and Controversies," Philosophical Transactions of the Royal Society of London, 1996, vol. 351 (1346), pp. 1495-1503.
Werry T.D., et al., "RNA Editing of the Serotonin 5HT2C Receptor and its Effects on Cell Signalling, Pharmacology and Brain Function," Pharmacology & Therapeutics, 2008, vol. 119 (1), pp. 7-23.

(Continued)

*Primary Examiner* — Douglas M Willis
(74) *Attorney, Agent, or Firm* — Neal Gerber & Eisenberg LLP

(57) ABSTRACT

The present invention relates to compound of formula (I) as tricyclic hexahydrodiazepinoquinolines carrying a cyclic substituent, useful for modulating the $5\text{-HT}_{2C}$ receptor and preventing and/or treating conditions and disorders that respond to the modulation of the $5\text{-HT}_{2C}$ receptor. The present invention also relates to methods for producing compounds of formula (I), pharmaceutical compositions containing such compounds, and methods for preventing or treating conditions and disorders that respond to the modulation of the $5\text{-HT}_{2C}$ receptor by administering compounds of formula (1) or pharmaceutical compositions thereof.

48 Claims, No Drawings

(56) References Cited

OTHER PUBLICATIONS

Lindstrom et al., "Microwave Assisted Organic Synthesis-A Review," Tetrahedron 57 (2001) pp. 9225-9283.
"Microwaves in Organic Synthesis", André Loupy (Ed.), Wiley-VCH 2002.
International Search Report and Written Opinion for Application No. PCT/EP2015/055335, mailed on May 6, 2015, 9 pages.
Arjona A.A., et al., "Effect of a 5-Ht(2C) Serotonin Agonist, Dexnorfenfluramine, on Amyloid Precursor Protein Metabolism in Guinea Pigs," Brain Research, 2002, vol. 951 (1), pp. 135-140.
Barr A.M., et al., "The Selective Serotonin-2A Receptor Antagonist M100907 Reverses Behavioral Deficits in Dopamine Transporter Knockout Mice," Neuropsychopharmacology, 2004, vol. 29 (2), pp. 221-228.
Berge S.M., et al., "Pharmaceutical Salts," Journal of Pharmaceutical Sciences, 1977, vol. 66 (1), pp. 1-19.
Brennan P.E., et al., "Discovery of a Novel Azepine Series of Potent and Selective 5-Ht2C Agonists as Potential Treatments for Urinary Incontinence," Bioorganic Medicinal Chemistry Letters, 2009, vol. 19 (17), pp. 4999-5003.
Brus R., et al., "Influence of 5,7-Dihydroxytryptamine (5,7-DHT) on the Antinociceptive Effect of Serotonine (5-HT) 5-HT 2C Receptor Agonist in Male and Female Rats," Medical Science & Monitoring, 1997, vol. 3 (5), pp. 654-656.
Bubar M.J., et al., "Prospects for Serotonin 5-HT2R Pharmacotherapy in Psychostimulant Abuse," Progress in Brain Research, 2008, vol. 172, pp. 319-346.
Chou-Green J.M., et al., "Compulsive Behavior in the 5-HT2C Receptor Knockout Mouse," Physiology & Behavior, 2003, vol. 78 (4-5), pp. 641-649.
Chou-Green J.M., et al., "Repeated Stress in Young and Old 5-HT(2C) Receptor Knockout Mice," Physiology & Behavior, 2003, vol. 79 (2), pp. 217-226.
Cryan J.F., et al., "Antidepressant-Like Behavioral Effects Mediated by 5-Hydroxytryptamine(2C) Receptors," The Journal of Pharmacology and Experimental Therapeutics, 2000, vol. 295 (3), pp. 1120-1126.
Davis K.L., et al., "Dopamine in Schizophrenia: A Review and Reconceptualization," The American Journal of Psychiatry, 1991, vol. 148 (11), pp. 1474-1486.
Dekeyne A., et al., "S32006, A Novel 5-HT2C Receptor Antagonist Displaying Broad-Based Antidepressant and Anxiolytic Properties in Rodent Models," Psychopharmacology, 2008, pp. 199 (4), pp. 549-568.
Del Guidice T., et al., "Stimulation of 5-HT2C Receptors Improves Cognitive Deficits Induced by Human Tryptophan Hydroxylase 2 Loss of Function Mutation," Neuropsychopharmacology, 2014, vol. 39 (5), pp. 1125-1134.
Denkewalter R.G., et al., Progress in Drug Research, 1966, vol. 10, 23 pages.
Di Giovanni G., et al., "Preferential Modulation of Mesolimbic vs. Nigrostriatal Dopaminergic Function by Serotonin (2C/2B) Receptor Agonists: A Combined in Vivo Electrophysiological and Microdialysis Study," Synapse, 2000, vol. 35 (1), pp. 53-61.
Di Matteo V., et al., "SB 242084, A Selective Serotonin2C Receptor Antagonist, Increases Dopaminergic Transmission in the Mesolimbic System," Neuropharmacology, 1999, vol. 38 (8), pp. 1195-1205.
Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.
Du Y., et al., "Editing of the Serotonin 2C Receptor Pre-mRNA: Effects of the Morris Water Maze," Gene, 2007, vol. 391 (1-2), pp. 186-197.

Dunlop J., et al., "Characterization of Vabicaserin (SCA-136), a Selective 5-hydroxytryptamine 2C Receptor Agonist," Journal of Pharmacology and Experimental Therapeutics, 2011, vol. 337 (3), pp. 673-680.
Dunlop J., et al., "Pharmacological Profile of the 5-HT2C Receptor Agonist Way-163909; Therapeutic Potential in Multiple Indications," CNS Drug Reviews, 2006, vol. 12 (3-4), pp. 167-177.
Dunlop J., et al., "Way-163909 [(7bR,10aR)-1,2,3,4,8,9,10,10a-Octahydro-7bHcyclopenta-[b][1,4]Diazepino[6,7,1Hi] Indole], A Novel 5- Hydroxytryptamine 2C Receptor-Selective Agonist with Anorectic Activity," The Journal of Pharmacology and Experimental Therapeutics, 2005, vol. 313 (2), pp. 862-869.
Esposito E., et al., "Role of central 5-HT2C receptor in the control of basal ganglia functions," The Basal Ganglia Pathophysiology, 2007, pp. 97-127.
Fletcher P.J., et al., "Serotonin Receptors as Potential Targets for Modulation of Nicotine Use and Dependence," Progress in Brain Research, 2008, vol. 172, pp. 361-383.
Frank M.G., et al., "Sleep and Sleep Homeostasis in Mice Lacking the 5-HT2C Receptor," Neuropsychopharmacology, 2002, vol. 27 (5), pp. 869-873.
Isaac M., "Serotonergic 5-HT2C Receptors as a Potential Therapeutic Target for the Design Antiepileptic Drugs," Current Topic in Medicinal Chemistry, 2005, vol. 5 (1), pp. 59-67.
Iwamoto K., et al., "Altered RNA Editing of Serotonin 2C Receptor in a Rat Model of Depression," Neuroscience Search, 2005, vol. 53 (1), pp. 69-76.
Iwamoto K., et al., "RNA Editing of Serotonin 2C Receptor in Human Postmortem Brains of Major Mental Disorders," Neuroscience Letters, 2003, vol. 346 (3), pp. 169-172.
Kao T., et al., "Role of the 5-HT2C Receptor in Improving Weight-Supported Stepping in Adult Rats Spinalized as Neonates," Brain Research, 2006, vol. 1112 (1), pp. 159-168.
Kaufman M.J., et al., "Cyclic Gmp Inhibits Phosphoinositide Turnover in Choroid Plexus: Evidence for Interactions between Second Messengers Concurrently Triggered by 5-HT2C Receptors," Neuroscience Letters, 1996, vol. 206 (2-3), pp. 153-156.
Leone M., et al., "The Serotonergic System in Migraine," Journal of Headache Pain, 2001, vol. 2, pp. S43-S46.
Liu J., et al., "Prediction of Efficacy of Vabicaserin, a 5-HT2C Agonist, for the Treatment of Schizophrenia Using a Quantitative Systems Pharmacology Model," CPT: Pharmacometrics & Systems Pharmacology, 2014, vol. 3, p. e111.
Lopez-Gimenez J.F., et al., "Regional Distribution and Cellular Localization of 5-HT2C Receptor MRNA in Monkey Brain: Comparison with [3H]Mesulergine Binding Sites and Choline Acetyltransferase MRNA," Synapse, 2001, vol. 42, pp. 2010-12-26.
Loupy A., Ed., "A Tentative Rationalization of Microwave effects in Organic synthesis according to the reaction medium and mechanistic considerations," Tetrahedron 57 (2001) pp. 9199-9223.
Marquis K.L., et al., "Way-163909 [(7bR,10aR)-1,2,3,4,8,9,10,10a-Octahydro-7bH-Cyclopenta-[b][1,4]Diazepino [6,7,1Hi]Indole]: A Novel 5-Hydroxytryptamine 2C Receptor-Selective Agonist with Preclinical Antipsychotic-Like Activity," The Journal of Pharmacology and Experimental Therapeutics, 2007, vol. 320 (1), pp. 486-496.
Mbaki Y., et al., "Investigation of the Role of 5-HT2 Receptor Subtypes in the Control of the Bladder and the Urethra in the Anaesthetized Female Rat," British Journal of Pharmacology, 2008, vol. 155 (3), pp. 343-356.
Mosienko V., "Exaggerated Aggression and Decreased Anxiety in Mice Deficient in Brain Serotonin," Translational Psychiatry, 2012, vol. 2, p. e122.
Motofei I.G., "A Dual Physiological Character for Sexual Function: The Role of Serotonergic Receptors," BJU International, 2008, vol. 101 (5), pp. 531-534.
Nakae A., et al., "Serotonin2C Receptor MRNA Editing in Neuropathic Pain Model," Neuroscience Research, 2008, vol. 60 (2), pp. 228-231.

(56) References Cited

OTHER PUBLICATIONS

Nakae A., et al., "The Role of RNA Editing of the Serotonin 2C Receptor in a Rat Model of Oro-Facial Neuropathic Pain," The European Journal of Neuroscience, 2008, vol. 27 (9), pp. 2373-2379.

Niswender C.M., et al., "RNA Editing of the Human Serotonin 5-HT2C Receptor. Alterations in Suicide and Implications for Serotonergic Pharmacotherapy," Neuropsychopharmacology, 2001, vol. 24 (5), pp. 478-491.

Nunes-De-Souza V., et al., "5-HT2 Receptor Activation in the Midbrain Periaqueductal Grey (PAG) Reduces Anxiety-Like Behaviour in Mice," Behavioural Brain Research, 2008, vol. 187 (1), pp. 72-79.

Obata H., et al., "Antiallodynic Effects of Intrathecally Administered 5-HT(2C) Receptor Agonists in Rats with Nerve Injury," Pain, 2004, vol. 108 (1-2), pp. 163-169.

Obata H., et al., "Possible Involvement of Spinal Noradrenergic Mechanisms in the Antiallodynic Effect of Intrathecally Administered 5-HT2C Receptor Agonists in the Rats with Peripheral Nerve Injury," European Journal of Pharmacology, 2007, vol. 567 (1-2), pp. 89-94.

Pompeiano M., et al., "Distribution of the Serotonin 5-HT2 Receptor Family mRNAs: Comparison between 5-HT2A and 5-HT2C Receptors," Molecular Brain Research, 1994, vol. 23 (1-2), pp. 163-178.

Prescott, Ed., Methods in Cell Biology, vol. XIV, Academic Press, New York, 1976, pp. 33.

Remington G., et al., "Atypical antipsychotics: are some more atypical than others," Psychopharmacology, 2000, vol. 148, pp. 3-15.

Rocha B.A., et al., "Enhanced Locomotor, Reinforcing, and Neurochemical Effects of Cocaine in Serotonin 5-Hydroxytryptamine 2C Receptor Mutant Mice," The Journal of Neuroscience, 2002, vol. 22 (22), pp. 10039-10045.

Rosenzweig-Lipson S., et al., "5-HT2C Receptor Agonists as an Innovative Approach for Psychiatric Disorders," Drug News & Perspectives, 2007, vol. 20 (9), pp. 565-571.

Rosenzweig-Lipson S., et al., "Antidepressant-Like Effects of the Novel, Selective, 5-HT2C Receptor Agonist Way-163909 in Rodents," Psychopharmacology, 2007, vol. 192 (2), pp. 159-170.

Rosenzweig-Lipson S., et al., "Antiobesity-Like Effects of the 5-HT2C Receptor Agonist Way-161503," Brain Research, 2006, vol. 1073-1074, pp. 240-251.

Schmauss C., "Serotonin 2C Receptors: Suicide, Serotonin, and Runaway RNA Editing," The Neuroscientist, 2003, vol. 9 (4), pp. 237-242.

* cited by examiner

SUBSTITUTED [1,4]DIAZEPINO[6,7,1-IJ]QUINOLINES AS SEROTONIN 5-HT2C RECEPTOR MODULATORS

CROSS-REFERENCE TO RELATED APPLICATION(S)

This claims priority to U.S. Provisional Patent Application No. 61/953,424, filed on Mar. 14, 2014, the entire contents of which are fully incorporated herein by reference.

FIELD OF THE INVENTION

The present invention relates to tricyclic hexahydrodiazepinoquinolines carrying a cyclic substituent, to a method for producing them, to a pharmaceutical composition containing such compounds, to their use as modulators, especially agonists or partial agonists, of the 5-HT$_{2C}$ receptor, their use for preparing a medicament for the prevention or treatment of conditions and disorders which respond to the modulation of 5-HT$_{2C}$ receptor, to a method for preventing or treating conditions and disorders which respond to the modulation of 5-HT$_{2C}$ receptor, and processes for preparing such compounds and compositions.

BACKGROUND OF THE INVENTION

Diseases, disorders and conditions where 5-HT$_{2C}$ modulation is desired are for example depression, anxiety, schizophrenia, bipolar disorder, obsessive compulsive disorder, migraine, pain, epilepsy, substance abuse, eating disorders, obesity, diabetes, erectile dysfunction and others.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of adenylate cyclase or phospholipase Cγ.

Alterations in the activity of multiple neurotransmitter receptor systems (dopamine, serotonin, glutamate, GABA, acetylcholine) have been implicated in the manifestation of the symptoms of schizophrenia. The most widely accepted "Dopamine Hypothesis of Schizophrenia" in its simplest form states that the positive symptoms of this pathology relate to a functional hyperactivity of the mesolimbic dopaminergic system, while the negative and cognitive aspects can be traced to a functional hypoactivity of the mesocortical dopaminergic projections. Atypical antipsychotics block the mesolimbic dopaminergic neurotransmission, thereby controlling positive symptoms, with little or no effect on the nigrostriatal system, leading to less induction of extrapyramidal side effects (EPS).

Primary negative and cognitive symptoms of schizophrenia reflect a dysfunction of the frontal cortex ("hypofrontality"), which is thought to be induced by a decreased tone in the mesocortical dopaminergic projection field [Davis K L, Kahn R S, Ko G and Davidson M (1991). Dopamine in schizophrenia: a review and re-conceptualization. *Am J Psychiatry* 148: 1474-86. Weinberger D R and Berman K F (1996). Prefrontal function in schizophrenia: confounds and controversies. *Philos Trans R Soc Lond B Biol Sci* 351: 1495-503]. Agents that selectively enhance dopamine levels in the cortex have the potential to address the negative symptoms of this disorder. Atypical antipsychotics lack robust efficacy against negative and cognitive components of the schizophrenic syndrome.

The schizophrenic symptomatology is further complicated by the occurrence of drug-induced so-called secondary negative symptoms and cognitive impairment, which are difficult to distinguish from primary negative and cognitive symptoms [Remington G and Kapur S (2000). Atypical antipsychotics: are some more atypical than others? *Psychopharmacol* 148: 3-15]. The occurrence of secondary negative symptoms not only limits therapeutic efficacy but also, together with these side effects, negatively affects patient compliance.

It may thus be hypothesized that a novel mechanistic approach that blocks dopaminergic neurotransmission in the limbic system but does not affect the striatal and pituitary projection fields, and stimulates frontocortical projection fields, would provide an efficacious treatment for all parts of the schizophrenic pathology, including its positive, negative and cognitive symptoms. Moreover, a selective compound that is substantially free of the ancillary pharmacology that characterizes current agents would be expected to avoid a variety of off-target side effects that plague current treatments such as extrapyramidal side effects (EPS) and weight gain.

The 5-HT$_{2C}$ receptor, previously named 5-HT1C, is a G-protein-coupled receptor, which couples to multiple cellular effector systems including the phospholipase C, A and D pathways. It is found primarily in the brain and its distribution is particularly high in the plexus choroideus, where it is assumed to control cerebrospinal fluid production [Kaufman M J, Hirata F (1996) Cyclic GMP inhibits phosphoinositide turnover in choroid plexus: evidence for interactions between second messengers concurrently triggered by 5-HT$_{2C}$ receptors. *Neurosci Lett* 206:153-156]. Very high levels were also found in the retrosplenial, piriform and entorhinal cortex, anterior olfactory nucleus, lateral septal nucleus, subthalamic nucleus, amygdala, subiculum and ventral part of CA3, lateral habenula, substantia nigra pars compacta, several brainstem nuclei and the whole grey matter of the spinal cord [Pompeiano M, Palacios J M, Mengod G (1994). Distribution of the serotonin 5-HT2 receptor family mRNAs: comparison between 5-HT$_{2A}$ and 5-HT$_{2C}$ receptors. *Brain Res Mol Brain Res* 23:163-178]. A comparison of the distribution of 5-HT$_{2C}$ mRNA with that of 5-HT$_{2C}$ protein in monkey and human brains has revealed both pre- and postsynaptic localization [Lopez-Gimenez J F, Mengod G, Palacios J M, Vilaro M T (2001) Regional distribution and cellular localization of 5-HT$_{2C}$ receptor mRNA in monkey brain: comparison with [$^3$H]mesulergine binding sites and choline acetyltransferase mRNA. *Synapse* 42:12-26].

It is anticipated that modulation of the 5-HT$_{2C}$ receptor will improve disorders such as depression, anxiety, schizophrenia, cognitive deficits of schizophrenia, obsessive compulsive disorder, bipolar disorder, neuropsychiatric symptoms in Parkinson' disease, in Alzheimer's disease or Lewy Body dementia, migraine, epilepsy, substance abuse, eating disorders, obesity, diabetes, sexual dysfunction/erectile dysfunction, sleep disorders, psoriasis, Parkinson's disease, pain conditions and disorders, and spinal cord injury, smoking cessation, ocular hypertension and Alzheimer's disease. Modulators of the 5-$HT_{2C}$ receptor are also shown to be useful in the modulation of bladder function, including the prevention or treatment of urinary incontinence.

Compounds with a structure similar to the compounds of the present invention have been described in WO 2014/041131 and WO 03/091250.

There is an ongoing need for providing compounds having high affinity and in particular also high selectivity for the 5-$HT_{2C}$ receptor. In particular the compounds should have low affinity to adrenergic receptors, such as the $\alpha_1$-adrenergic receptor, histamine receptors, such as the $H_1$-receptor, and dopaminergic receptors, such as the $D_2$-receptor, in order to avoid or reduce side effects associated with modulation of these receptors, such as postural hypotension, reflex tachycardia, potentiation of the antihypertensive effect of prazosin, terazosin, doxazosin and labetalol or dizziness associated with the blockade of the $\alpha_1$-adrenergic receptor, weight gain, sedation, drowsiness or potentiation of central depressant drugs associated with the blockade of the $H_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, mentstrual changes, sexual dysfunction in males), associated with the blockade of the $D_2$-receptor, and even more important no induction of weight gain in combination with severe metabolic dysfunction found for marketed antipsychotic drugs.

It is moreover desirable that the compounds have low affinity or alternatively an antagonistic effect to/on other serotonergic receptors, especially the 5-$HT_{2A}$ and/or 5-$HT_{2B}$ receptors, in order to avoid or reduce side effects associated with modulation of these receptors, such as changes (thickening) of the heart tissue associated with agonism at the 5-$HT_{2B}$ receptor, and psychotomimetic effect induced by agonism at the 5-$HT_{2A}$ receptor. Ideally they should show an agonistic action on the 5-$HT_{2C}$ receptor, an antagonistic action on the 5-$HT_{2A}$ receptor or alternatively no affinity to the 5-$HT_{2A}$ receptor and no affinity to the 5-$HT_{2B}$ receptor or alternatively an antagonistic action on the 5-$HT_{2B}$ receptor. Even more ideally the compounds should display an agonistic action on the 5-$HT_{2C}$ receptor in combination with an antagonistic action on the 5-$HT_{2A}$ receptor and no affinity to the 5-$HT_{2B}$ receptor.

Besides the affinity and selectivity for the 5-$HT_{2C}$ receptor, further properties may be advantageous for the treatment and/or prophylaxis of 5-$HT_{2C}$-related disorders, such as, for example:

1.) the metabolic stability, for example determined from the half-lives, measured in vitro, in liver microsomes from various species (e.g. rat or human);

2.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

3.) a suitable solubility in water (in mg/mL);

4.) suitable pharmacokinetics (time course of the concentration of the compound of the invention in plasma or in tissue, for example brain). The pharmacokinetics can be described by the following parameters: half-life (in h), volume of distribution (in l·kg-l), plasma clearance (in l·h-l·kg-l), AUC (area under the curve, area under the concentration-time curve, in ng·h·l-l), oral bioavailability (the dose-normalized ratio of AUC after oral administration and AUC after intravenous administration), the so-called brain-plasma ratio (the ratio of AUC in brain tissue and AUC in plasma);

5.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was an object of the present invention to provide compounds for the treatment or prophylaxis of various 5-$HT_{2C}$-related diseases. The compounds were intended to have a high affinity to the 5-$HT_{2C}$ receptor and be potent and efficacious 5-$HT_{2C}$ agonists. In addition, the compounds of the invention were intended to have one or more of the aforementioned advantages, namely low affinity on other serotonergic receptors, and especially the lack of potent agonistic effect (antagonism preferred) on the 5-$HT_{2A}$ and/or 5-$HT_{2B}$ receptors, and additionally one or more of those advantages mentioned under 1.) to 5.).

The present invention provides compounds which have an affinity for the 5-$HT_{2C}$, thus allowing the treatment of disorders related to or affected by the 5-$HT_{2C}$ receptor.

SUMMARY OF THE INVENTION

The present invention relates to tricyclic hexahydrodiazepinoquinolines carrying a cyclic substituent, to a method for producing them, to compositions comprising such compounds, their use as modulators, especially agonists or partial agonists, of the 5-$HT_{2C}$ receptor, their use for preparing a medicament for the prevention or treatment of conditions and disorders which respond to the modulation of 5-$HT_{2C}$ receptor, to a method for preventing or treating conditions and disorders which respond to the modulation of 5-$HT_{2C}$ receptor, and processes for preparing such compounds and compositions.

In one aspect, the present invention relates to compounds of the formula (I):

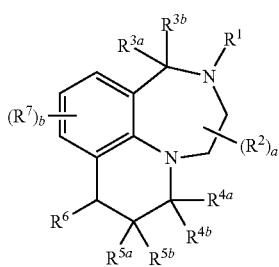

(I)

wherein
$R^1$ is selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —C(=O)$R^9$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{10}$;

each $R^2$ is independently selected from the group consisting of cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy-$C_1$-$C_4$-alkyl, fluorinated $C_1$-$C_6$-alkoxy-$C_1$-$C_4$-alkyl, —$CH_2NR^{11a}R^{11b}$, —C(=O)$R^9$, phenyl, phenyl-$C_1$-$C_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; or
two radicals $R^2$ bound to the same carbon atom, together with the carbon atom they are bound to, form a 3-, 4-, 5-, 6-, 7- or 8-membered saturated, partially unsaturated or maximally unsaturated ring (i.e. a spiro-bound ring), where the ring may contain 1, 2, 3 or 4 heteroatoms or heteroatom-containing groups selected from O, S, N, SO, $SO_2$, C=O and C=S as ring members, and where the ring may be substituted with one or more substituents $R^{10}$;

$R^{3a}$ and $R^{3b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy-$C_1$-$C_4$-alkyl, fluorinated $C_1$-$C_6$-alkoxy-$C_1$-$C_4$-alkyl, —$CH_2NR^{11a}R^{11b}$, —C(=O)$R^9$, phenyl, phenyl-$C_1$-$C_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$;

$R^{4a}$ and $R^{4b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy-$C_1$-$C_4$-alkyl, fluorinated $C_1$-$C_6$-alkoxy-$C_1$-$C_4$-alkyl, —$CH_2NR^{11a}R^{11b}$, —C(=O)$R^9$, phenyl, phenyl-$C_1$-$C_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; or
$R^{4a}$ and $R^{4b}$ form together a group =O or =S; or
$R^{4a}$ and $R^{4b}$, together with the carbon atom they are bound to, form a 3-, 4-, 5-, 6-, 7- or 8-membered saturated, partially unsaturated or maximally unsaturated ring (i.e. a spiro-bound ring), where the ring may contain 1, 2, 3 or 4 heteroatoms or heteroatom-containing groups selected from O, S, N, SO, $SO_2$, C=O and C=S as ring members, and where the ring may be substituted with one or more substituents $R^{10}$;

$R^{5a}$ and $R^{5b}$, independently of each other, are selected from the group consisting of hydrogen, halogen, cyano, nitro, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{11a}R^{11b}$, —$CH_2NR^{11a}R^{11b}$, —$NR^{11a}C(O)R^9$, —C(=O)$R^9$, $SO_2NR^{11a}R^{11b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; where $R^{5a}$ and $R^{5b}$ are not simultaneously hydroxyl; or
$R^{5a}$ and $R^{5b}$, together with the carbon atom they are bound to, form a 3-, 4-, 5-, 6-, 7- or 8-membered saturated, partially unsaturated or maximally unsaturated ring (i.e. a spiro-bound ring), where the ring may contain 1, 2, 3 or 4 heteroatoms or heteroatom-containing groups selected from O, S, N, SO, $SO_2$, C=O and C=S as ring members, and where the ring may be substituted with one or more substituents $R^{10}$;

$R^6$ is a cyclic radical selected from the group consisting of $C_3$-$C_6$-cycloalkyl which may carry one or more radicals $R^8$; and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$, and optionally also 1 or 2 groups C=O and/or C=S, as ring members, where the heterocyclic ring may be substituted with one or more substituents $R^{10}$;

each $R^7$ is independently selected from the group consisting of halogen, cyano, nitro, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkenyl, fluorinated $C_3$-$C_8$-cycloalkenyl, $C_1$-$C_6$-alkoxy, fluorinated $C_1$-$C_6$-alkoxy, $C_1$-$C_6$ alkoxy $C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{11a}R^{11b}$, —$CH_2NR^{11a}R^{11b}$, —$NR^{11a}C(O)R^9$, —$C(O)R^9$, $SO_2NR^{11a}R^{11b}$, $C_1$-$C6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; or two radicals $R^7$ bound on neighboring carbon atoms, together with the carbon atoms they are bound to, form a 3-, 4-, 5-, 6-, 7- or 8-membered partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{10}$;

each $R^8$ is independently selected from the group consisting of halogen, cyano, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, —$NR^{11a}R^{11b}$, —$CH_2NR^{11a}R^{11b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{10}$;

or two radicals $R^8$ bound to the same carbon atom may form together a group =O or =S;

each $R^9$ is independently selected from the group consisting of hydrogen, cyano, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —$NR^{11a}R^{11b}$, —$CH_2NR^{11a}R^{11b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{10}$;

each $R^{10}$ is independently selected from the group consisting of halogen, cyano, nitro, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —COOH, —$NR^{11a}R^{11b}$, —$CH_2NR^{11a}R^{11b}$, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, $SO_2NR^{11a}R^{11b}$, $C_1$-$C_6$-alkylcarbonyloxy and fluorinated $C_1$-$C_6$-alkylcarbonyloxy;

or two radicals $R^{10}$, together with the atom(s) they are bound to, form a saturated, partially unsaturated or maximally unsaturated 3-, 4-, 5-, 6- or 7-membered carbocyclic or heterocyclic ring, where the heterocyclic ring contains 1, 2 or 3 heteroatoms or heteroatom groups independently selected from N, O, S, NO, SO, $SO_2$, C=O and C=S as ring members;

$R^{11a}$ and $R^{11b}$, independently of each other and independently of each occurrence, are selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, phenyl and benzyl, where the phenyl moieties in the two last-mentioned radicals may carry 1, 2 or 3 substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy; or, if $R^{11a}$ and $R^{11b}$ are bound to the same nitrogen atom, together with this nitrogen atom may form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy;

a is 0, 1 or 2; and
b is 0, 1, 2 or 3;
or an N-oxide, a tautomeric form, a stereoisomer or a pharmaceutically acceptable salt thereof.

In another aspect, the invention relates to a pharmaceutical composition comprising a therapeutically effective amount of at least one compound of formula I or an N-oxide, a tautomeric form, a stereoisomer or a pharmaceutically acceptable salt thereof, in combination with at least one pharmaceutically acceptable carrier and/or auxiliary substance.

In yet another aspect, the invention relates to a compound of formula I or an N-oxide, a tautomeric form, a stereoisomer or a pharmaceutically acceptable salt thereof for use as a medicament.

In yet another aspect, the invention relates to a compound of formula I or an N-oxide, a tautomeric form, a stereoisomer or a pharmaceutically acceptable salt thereof for the treatment of disorders which responds to the modulation of the 5-$HT_{2C}$ receptor.

In yet another aspect, the invention relates to the use of a compound of formula I or of an N-oxide, a tautomeric form, a stereoisomer or a pharmaceutically acceptable salt thereof for the manufacture of a medicament for the treatment of disorders which respond to the modulation of the 5-$HT_{2C}$ receptor.

In yet another aspect, the invention relates to the use of a compound of formula I or of an N-oxide, a tautomeric form, a stereoisomer or a pharmaceutically acceptable salt thereof for the manufacture of a medicament for the treatment of disorders selected from the group consisting of damage of the central nervous system, disorders of the central nervous system, eating disorders, ocular hypertension, cardiovascular disorders, gastrointestinal disorders and diabetes, and especially from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, neuropsychiatric symptoms in Alzheimer's disease (e.g. aggression), behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, neuropsychiatric symptoms in Parkinson's disease (e.g. aggression), Lewy Body dementia, neuropsychiatric symptoms in Lewy Body dementia (e.g. aggression), spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance.

In yet another aspect, the invention relates to a method for treating disorders which respond to the modulation of the 5-HT$_{2C}$ receptor, which method comprises administering to a subject in need thereof at least one compound of formula I or an N-oxide, a tautomeric form, a stereoisomer or a pharmaceutically acceptable salt thereof.

In yet another aspect, the invention relates to a method for treating disorders selected from the group consisting of damage of the central nervous system, disorders of the central nervous system, eating disorders, ocular hypertension, cardiovascular disorders, gastrointestinal disorders and diabetes, and especially from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, neuropsychiatric symptoms in Alzheimer's disease (e.g. aggression), behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, neuropsychiatric symptoms in Parkinson's disease (e.g. aggression), Lewy Body dementia, neuropsychiatric symptoms in Lewy Body dementia (e.g. aggression), spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance, which method comprises administering to a subject in need thereof at least one compound of formula I or an N-oxide, a tautomeric form, a stereoisomer or a pharmaceutically acceptable salt thereof.

DETAILED DESCRIPTION

The compounds of the formula I may exist in different spatial arrangements. For example, if the compounds possess one or more centers of asymmetry, polysubstituted rings or double bonds, or as different tautomers, the present invention contemplates the possible use of enantiomeric mixtures, in particular racemates, diastereomeric mixtures and tautomeric mixtures, such as the respective essentially pure enantiomers, diastereomers and tautomers of the compounds of formula I and/or their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, acetic acid, trifluoroacetic acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhäuser Verlag, Basel and Stuttgart, 1966.

The compounds of formula I may also be present in the form of tautomers. In one aspect, tautomery may be present in compounds I wherein $R^{4a}$ and $R^{4b}$ form together a group =O and $R^{5a}$ or $R^{5b}$ is H. For example, the compounds of formula I may have the following tautomeric formulae:

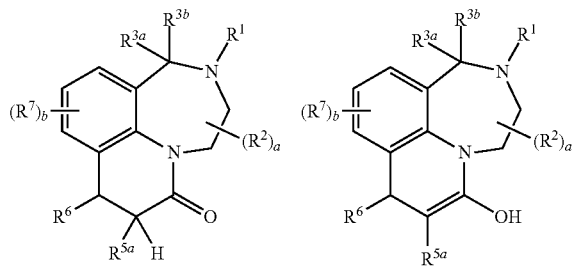

In another aspect, tautomery may be present in compounds I containing rings which have one or more C=O groups as ring members which are neighbored to a $CH_2$ group.

The organic moieties mentioned in the above definitions of the variables are, like the term halogen, collective terms for individual listings of the individual group members. The prefix $C_n$-$C_m$ indicates in each case the possible number of carbon atoms in the group.

The term "halogen" denotes in each case fluorine, bromine, chlorine or iodine. In one aspect, the halogen may be fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "fluorinated alkyl" as used herein refers to straight-chain or branched alkyl groups having 1 to 2 ("fluorinated $C_1$-$C_2$-alkyl"), 1 to 3 ("fluorinated $C_1$-$C_3$-alkyl"), 1 to 4 ("fluorinated $C_1$-$C_4$-alkyl") or 1 to 6 ("fluorinated $C_1$-$C_6$-alkyl") carbon atoms (as mentioned above), where some or all of the hydrogen atoms in these groups are replaced by fluorine atoms. Fluorinated $C_1$-$C_2$-alkyl is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl. Fluorinated $C_1$-$C_4$-alkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like. Fluorinated $C_1$-$C_6$-alkyl is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Additionally examples include for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 6-fluorohexyl, (R)-6-fluorohexyl, (S)-6-fluorohexyl, and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position, such as $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; and $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "fluorinated alkenyl" as used herein refers to unsaturated straight-chain or branched hydrocarbon radicals having 2 to 3 ("fluorinated $C_2$-$C_3$-alkenyl"), 2 to 4 ("fluorinated $C_2$-$C_4$-alkenyl") or 2 to 6 ("fluorinated $C_2$-$C_6$-alkenyl") carbon atoms and a double bond in any position (as mentioned above), where some or all of the hydrogen atoms in these groups are replaced by fluorine atoms, such as, fluorovinyl, fluoroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("C2-C6-alkynyl") carbon atoms and one or two triple bonds in any position, such as $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, and $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1- dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "fluorinated alkynyl" as used herein refers to unsaturated straight-chain or branched hydrocarbon radicals having 2 to 3 ("fluorinated $C_2$-$C_3$-alkynyl"), 3 to 4 ("fluorinated $C_3$-$C_4$-alkynyl") or 2 to 6 ("fluorinated $C_2$-$C_6$-alkynyl") carbon atoms and one or two triple bonds in any position (as mentioned above), where some or all of the hydrogen atoms in these groups are replaced by fluorine atoms.

The term "cycloalkyl" as used herein refers to monocyclic saturated hydrocarbon radicals having 3 to 8 ("$C_3$-$C_8$-cycloalkyl"), in particular 3 to 6 carbon atoms ("$C_3$-$C_6$-cycloalkyl") or 3 to 5 carbon atoms ("$C_3$-$C_5$-cycloalkyl") or 3 or 4 carbon atoms ("$C_3$-$C_4$-cycloalkyl"). Examples for $C_3$-$C_4$-cycloalkyl are cyclopropyl and cyclobutyl. Examples of $C_3$-$C_5$-cycloalkyl are cyclopropyl, cyclobutyl and cyclopentyl. Examples of $C_3$-$C_6$-cycloalkyl are cyclopropyl, cyclobutyl, cyclopentyl and cyclohexyl. Examples of $C_3$-$C_8$-cycloalkyl are cyclopropyl, cyclobutyl, cyclopentyl, cyclohexyl, cycloheptyl and cyclooctyl.

The term "fluorinated cycloalkyl" as used herein refers to monocyclic saturated hydrocarbon groups having 3 to 8 ("$C_3$-$C_8$-halocycloalkyl") or preferably 3 to 6 ("$C_3$-$C_6$-halocycloalkyl") or 3 to 5 ("$C_3$-$C_5$-halocycloalkyl") carbon ring members (as mentioned above) in which some or all of the hydrogen atoms are replaced by fluorine atoms. Examples include 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, 1,2,2-trifluorocyclobutyl, 1-fluorocycloheptyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

The term "cycloalkenyl" as used herein refers to monocyclic partially unsaturated, non-aromatic hydrocarbon radicals having 3 to 8 ("$C_3$-$C_8$-cycloalkenyl"), in particular 5 to 7 carbon atoms ("$C_5$-$C_7$-cycloalkenyl") or 5 or 6 carbon atoms ("$C_5$-$C_6$-cycloalkenyl") and one or more non-cumulative, preferably one, C—C double bonds in the ring. Examples for $C_5$-$C_6$-cycloalkenyl are cyclopent-1-en-1-yl, cyclopent-1-en-3-yl, cyclopent-1-en-4-yl, cyclopenta-1,3-dien-1-yl, cyclopenta-1,3-dien-2-yl, cyclopenta-1,3-dien-5-yl, cyclohex-1-en-1-yl, cyclohex-1-en-3-yl, cyclohex-1-en-4-yl, cyclohexa-1,3-dien-1-yl, cyclohexa-1,3-dien-2-yl, cyclohexa-1,3-dien-5-yl, cyclohexa-1,4-dien-1-yl and cyclohexa-1,4-dien-3-yl. Examples of $C_5$-$C_7$-cycloalkenyl are, apart those mentioned above, include for $C_5$-$C_6$-cycloalkenyl, cyclohept-1-en-1-yl, cyclohept-1-en-3-yl, cyclohept-1-en-4-yl, cyclohept-1-en-5-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl and cyclohepta-1,4-dien-6-yl. Examples of $C_3$-$C_8$-cycloalkenyl are, apart those mentioned above for $C_5$-$C_6$-cycloalkenyl, cycloprop-1-en-1-yl, cycloprop-1-en-3-yl, cyclobut-1-en-1-yl, cyclobut-1-en-3-yl, cyclooct-1-en-1-yl, cyclooct-1-en-3-yl, cyclooct-1-en-4-yl, cyclooct-1-en-5-yl, cycloocta-1,3-dien-1-yl, cycloocta-1,3-dien-2-yl, cycloocta-1,3-dien-5-yl, cycloocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,5-dien-1-yl, and cycloocta-1,5-dien-3-yl.

The term "fluorinated cycloalkenyl" as used herein refers to monocyclic partially unsaturated, non-aromatic hydrocarbon radicals having 3 to 8 ("fluorinated $C_3$-$C_8$-cycloalkenyl"), in particular 5 to 7 carbon atoms ("fluorinated $C_5$-$C_7$-cycloalkenyl") or 5 or 6 carbon atoms ("fluorinated $C_5$-$C_6$-cycloalkenyl") and one or more non-cumulative, preferably one, C—C double bonds in the ring and in which some or all of the hydrogen atoms are replaced by fluorine atoms.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl") as defined above which is bound to the remainder of the molecule via a $C_1$-$C_4$-alkyl group, as defined above. The term "cycloalkyl-$C_1$-$C_2$-alkyl" refers to a $C_3$-$C_8$-cycloalkyl group ("$C_3$-$C_8$-cycloalkyl-$C_1$-$C_2$-alkyl"), preferably a $C_3$-$C_6$-cycloalkyl group ("$C_3$-$C_6$-cycloalkyl-$C_1$-$C_2$-alkyl") as defined above which is bound to the remainder of the molecule via a $C_1$-$C_2$-alkyl group, as defined above. Examples for $C_3$-$C_6$-cycloalkyl-$C_1$-$C_2$-alkyl are cyclopropylmethyl, cyclopropylethyl, cyclobutylmethyl, cyclobutylethyl, cyclopentylmethyl, cyclopentylethyl, cyclohexylmethyl and cyclohexylethyl. Examples for $C_3$-$C_6$-cycloalkyl-$C_1$-$C_4$-alkyl, apart those mentioned for $C_3$-$C_6$-cycloalkyl-$C_1$-$C_2$-alkyl, are cyclopropylpropyl, cyclopropylbutyl, cyclobutylpropyl, cyclobutylbutyl, cyclopentylpropyl, cyclopentylbutyl, cyclohexylpropyl and cyclohexylbutyl. Examples for $C_3$-$C_8$-cycloalkyl-$C_1$-$C_2$-alkyl, apart those mentioned for $C_3$-$C_6$-cycloalkyl-$C_1$-$C_2$-alkyl, are cycloheptylmethyl, cycloheptylethyl, cyclooctylmethyl and cyclooctylethyl. Examples for $C_3$-$C_8$-cycloalkyl-$C_1$-$C_4$-alkyl, apart those mentioned for $C_3$-$C_8$-cycloalkyl-$C_1$-$C_2$-alkyl, are cycloheptylpropyl, cycloheptylbutyl, cyclooctylpropyl and cyclooctylbutyl.

The term "fluorinated cycloalkyl-$C_1$-$C_4$-alkyl" refers to a fluorinated $C_3$-$C_8$-cycloalkyl group ("fluorinated $C_3$-$C_8$-cycloalkyl-$C_1$-$C_4$-alkyl"), preferably a fluorinated C3-C6-cycloalkyl group ("fluorinated $C_3$-$C_6$-cycloalkyl-$C_1$-$C_4$-alkyl") as defined above which is bound to the remainder of the molecule via a $C_1$-$C_4$-alkyl group, as defined above. The term "fluorinated cycloalkyl-$C_1$-$C_2$-alkyl" refers to a fluorinated $C_3$-$C_8$-cycloalkyl group ("fluorinated $C_3$-$C_8$-cycloalkyl-$C_1$-$C_2$-alkyl"), preferably a fluorinated $C_3$-$C_6$-cycloalkyl group ("fluorinated $C_3$-$C_6$-cycloalkyl-$C_1$-$C_2$-alkyl") as defined above which is bound to the remainder of the molecule via a $C_1$-$C_2$-alkyl group, as defined above.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof.

The term "fluorinated $C_1$-$C_2$-alkoxy" is a fluorinated $C_1$-$C_2$-alkyl group, as defined above, attached via an oxygen atom. The term "fluorinated $C_1$-$C_3$-alkoxy" is a fluorinated $C_1$-$C_3$-alkyl group, as defined above, attached via an oxygen atom. The term "fluorinated $C_1$-$C_6$-haloalkoxy" is a fluorinated $C_1$-$C_6$-alkyl group, as defined above, attached via an oxygen atom. Fluorinated $C_1$-$C_2$-alkoxy is, for example, $OCH_2F$, $OCHF_2$, $OCF_3$, 1-fluoroethoxy, (R)-1-fluoroethoxy, (S)-1-fluoroethoxy, 2-fluoroethoxy, 1,1-difluoroethoxy, 1,2-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy or $OC_2F_5$. Fluorinated $C_1$-$C_3$-alkoxy is additionally, for example, 1-fluoropropoxy, (R)-1-fluoropropoxy, (S)-1-fluoropropoxy, 2-fluoropropoxy, (R)-2-fluoropropoxy, (S)-2-fluoropropoxy, 3-fluoropropoxy, 1,1-difluoropropoxy, 2,2-difluoropropoxy, 2,3-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, $OCH_2$—$C_2F_5$, $OCF_2$—$C_2F_5$ or 1-($CH_2F$)-2-fluoroethoxy. Fluorinated $C_1$-$C_4$-alkoxy is additionally, for example, 1-fluorobutoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy or nonafluorobutoxy. Fluorinated $C_1$-$C_6$-alkoxy is additionally, for example, 5-fluoropentoxy, undecafluoropentoxy, 6-fluorohexoxy or tridecafluorohexoxy.

The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "fluorinated $C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above, and wherein at least one, e.g. 1, 2, 3, 4 or all of the remaining hydrogen atoms (either in the alkoxy moiety or in the alkyl moiety or in both) are replaced by fluorine atoms. The term "fluorinated $C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above, and wherein at least one, e.g. 1, 2, 3, 4 or all of the remaining hydrogen atoms (either in the alkoxy moiety or in the alkyl moiety or in both) are replaced by fluorine atoms. Examples are difluoromethoxymethyl ($CHF_2OCH_2$), trifluoromethoxymethyl, 1-difluoromethoxyethyl ($CHF_2OCH(CH_3)$), 1-trifluoromethoxyethyl ($CF_3OCH(CH_3)$), 2-difluoromethoxyethyl ($CHF_2OCH_2CH_2$), 2-trifluoromethoxyethyl ($CF_3OCH_2CH_2$), methoxy-difluoromethyl ($CH_3OCF_2$), 2-methoxy-1,1-difluoroethyl ($CH_3OCH_2CF_2$), 2-methoxy-2,2-difluoroethyl ($CH_3OCF_2CH_2$), and the like.

The term "hydroxy-$C_1$-$C_4$-alkyl" as used herein, refers to a straight-chain or branched alkyl group having 1 to 4 carbon atoms, as defined above, where one hydrogen atom is replaced by a hydroxyl group. The term "hydroxy-$C_1$-$C_6$-alkyl" as used herein, refers to a straight-chain or branched alkyl group having 1 to 6 carbon atoms, as defined above, where one hydrogen atom is replaced by a hydroxyl group. Examples for hydroxy-$C_1$-$C_4$-alkyl include hydroxymethyl, 1-hydroxyethyl, 2-hydroxyethyl, 1-hydroxypropyl, 2-hydroxypropyl, 3-hydroxypropyl, 1-hydroxyprop-2-yl, 2-hydroxyprop-2-yl, 1-hydroxybutyl, 2-hydroxybutyl, 3-hydroxybutyl, 4-hydroxybutyl, 1-hydroxybut-2-yl, 2-hydroxybut-2-yl, 3-hydroxybut-2-yl, 4-hydroxybut-2-yl, hydroxy-tert-butyl and the like. Examples for hydroxy-$C_1$-$C_6$-alkyl are, apart those mentioned for hydroxy-$C_1$-$C_4$-alkyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl and the like.

The term "hydroxy-$C_1$-$C_4$-alkoxy" as used herein, refers to a $C_1$-$C_4$-alkoxy group, as defined above, where one hydrogen atom is replaced by a hydroxy group. The term "hydroxy-$C_1$-$C_6$-alkoxy" as used herein, refers to a $C_1$-$C_6$-alkoxy group, as defined above, where one hydrogen atom is replaced by a hydroxy group. Examples for hydroxy-$C_1$-$C_4$-alkoxy include hydroxymethoxy, 1-hydroxyethoxy, 2-hydroxyethoxy, 1-hydroxypropoxy, 2-hydroxypropoxy, 3-hydroxypropoxy, 1-hydroxy-2-propoxy, 2-hydroxy-2-propoxy, 1-hydroxybutoxy, 2-hydroxybutoxy, 3-hydroxybutoxy, 4-hydroxybutoxy, 1-hydroxy-2-butoxy, 2-hydroxy-2-butoxy, 3-hydroxy-2-butoxy, 4-hydroxy-2-butoxy, hydroxy-tert-butoxy and the like. Examples for hydroxy-$C_1$-$C_6$-alkoxy include, apart those mentioned for hydroxy-$C_1$-$C_4$-alkoxy, 1-hydroxypentoxy, 2-hydroxypentoxy, 3-hydroxypentoxy, 4-hydroxypentoxy, 5-hydroxypentoxy, 1-hydroxyhexoxy, 2-hydroxyhexoxy, 3-hydroxyhexoxy, 4-hydroxyhexoxy, 5-hydroxyhexoxy, 6-hydroxyhexoxy and the like.

The term "$C_1$-$C_4$-alkoxy-$C_1$-$C_4$-alkoxy" as used herein, refers to a $C_1$-$C_4$-alkoxy group, as defined above, where one hydrogen atom is replaced by a $C_1$-$C_4$-alkoxy group, as defined above. The term "$C_1$-$C_6$-alkoxy-$C_1$-$C_4$-alkoxy" as used herein, refers to a $C_1$-$C_4$-alkoxy group, as defined above, where one hydrogen atom is replaced by a $C_1$-$C_6$-alkoxy group, as defined above. Examples are methoxymethoxy, ethoxymethoxy, propoxymethoxy, isopropoxymethoxy, butoxymethoxy, sec-butoxymethoxy, isobutoxymethoxy, tert-butoxymethoxy, 1-methoxyethoxy, 1-ethoxyethoxy, 1-propoxyethoxy, 1-isopropoxyethoxy, 1-butoxyethoxy, 1-sec-butoxyethoxy, 1-isobutoxyethoxy, 1-tert-butoxyethoxy, 2-methoxyethoxy, 2-ethoxyethoxy, 2-propoxyethoxy, 2-isopropoxyethoxy, 2-butoxyethoxy, 2-sec-butoxyethoxy, 2-isobutoxyethoxy, 2-tert-butoxyethoxy, 1-methoxypropoxy, 1-ethoxypropoxy, 1-propoxypropoxy, 1-isopropoxypropoxy, 1-butoxypropoxy, 1-sec-butoxypropoxy, 1-isobutoxypropoxy, 1-tert-butoxypropoxy, 2-methoxypropoxy, 2-ethoxypropoxy, 2-propoxypropoxy, 2-isopropoxypropoxy, 2-butoxypropoxy, 2-sec-butoxypropoxy, 2-isobutoxypropoxy, 2-tert-butoxypropoxy, 3-methoxypropoxy, 3-ethoxypropoxy, 3-propoxypropoxy, 3-isopropoxypropoxy, 3-butoxypropoxy, 3-sec-butoxypropoxy, 3-isobutoxypropoxy, 3-tert-butoxypropoxy and the like.

The term "$C_1$-$C_2$-alkylthio" is a $C_1$-$C_2$-alkyl group, as defined above, attached via a sulfur atom. The term "$C_1$-$C_3$-alkylthio" refers to a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" refers to a $C_1$-$C_6$-alkyl group, as defined above, attached via a sulfur atom. The term "$C_1$-$C_{10}$-alkylthio" refers to a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio.

The term "fluorinated $C_1$-$C_2$-alkylthio" refers to a fluorinated $C_1$-$C_2$-alkyl group, as defined above, attached via a sulfur atom. The term "fluorinated $C_1$-$C_3$-alkylthio" refers to a fluorinated $C_1$-$C_3$-alkyl group, as defined above, attached via a sulfur atom. The term "fluorinated $C_1$-$C_4$-alkylthio" refers to a fluorinated $C_1$-$C_4$-alkyl group, as defined above, attached via a sulfur atom. The term "fluorinated $C_1$-$C_6$-alkylthio" refers to a fluorinated $C_1$-$C_6$-alkyl group, as defined above, attached via a sulfur atom. Fluorinated $C_1$-$C_2$-alkylthio refers to, for example, $SCH_2F$, $SCHF_2$, $SCF_3$, 2-fluoroethylthio, 2,2-difluoroethylthio, 2,2,2-trifluoroethylthio, or $SC_2F_5$. Fluorinated $C_1$-$C_3$-alkylthio may additionally, for example, include 2-fluoropropylthio, 3-fluoropropylthio, 2,2-difluoropropylthio, 2,3-difluoropropylthio, 3,3,3-trifluoropropylthio, $SCH_2$—$C_2F_5$, $SCF_2$—$C_2F_5$ or 1-($CH_2F$)-2-fluoroethylthio. Fluorinated $C_1$-$C_4$-alkylthio may additionally, for example, include 4-fluorobutylthio or nonafluorobutylthio. Fluorinated $C_1$-$C_6$-alkylthio is additionally, for example, 5-fluoropentylthio, undecafluoropentylthio, 6-fluorohexylthio or dodecafluorohexylthio.

The term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "fluorinated $C_1$-$C_2$-alkylsulfinyl" refers to a fluorinated $C_1$-$C_2$-alkyl group, as defined above, attached via a sulfinyl [S(O)] group. The term "fluorinated $C_1$-$C_3$-alkylsulfinyl" refers to a fluorinated $C_1$-$C_3$-alkyl group, as defined above, attached via a sulfinyl [S(O)] group. The term "fluorinated $C_1$-$C_4$-alkylsulfinyl" refers to a fluorinated $C_1$-$C_4$-alkyl group, as defined above, attached via a sulfinyl [S(O)] group. The term "fluorinated $C_1$-$C_6$-alkylsulfinyl" refers to a fluorinated $C_1$-$C_6$-alkyl group, as defined above, attached via a sulfinyl [S(O)] group. Fluorinated $C_1$-$C_2$-alkylsulfinyl is, for example, $S(O)CH_2F$, $S(O)CHF_2$, $S(O)CF_3$, 2-fluoroethylsulfinyl, 2,2-difluoroethylsulfinyl, 2,2,2-trifluoroethylsulfinyl, or $S(O)C_2F_5$. Fluorinated $C_1$-$C_3$-alkylsulfinyl may additionally, for example, include 2-fluoropropylsulfinyl, 3-fluoropropylsulfinyl, 2,2-difluoropropylsulfinyl, 2,3-difluoropropylsulfinyl, 3,3,3-trifluoropropylsulfinyl, $S(O)CH_2$—$C_2F_5$, $S(O)CF_2$—$C_2F_5$ or 1-($CH_2F$)-2-fluoroethylsulfinyl. Fluorinated $C_1$-$C_4$-alkylsulfinyl may additionally, for example, include 4-fluorobutylsulfinyl or nonafluorobutylsulfinyl. Fluorinated $C_1$-$C_6$-alkylsulfinyl may additionally, for example, include 5-fluoropentylsulfinyl, undecafluoropentylsulfinyl, 6-fluorohexylsulfinyl or dodecafluorohexylsulfinyl.

The term "$C_1$-$C_2$-alkylsulfonyl" refers to a $C_1$-$C_2$-alkyl group, as defined above, attached via a sulfonyl [S(O)$_2$] group. The term "$C_1$-$C_4$-alkylsulfonyl" refers to a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. $C_1$-$C_2$-Alkylsulfonyl refers to a methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "fluorinated $C_1$-$C_2$-alkylsulfonyl" refers to a fluorinated $C_1$-$C_2$-alkyl group, as defined above, attached via a sulfonyl $[S(O)_2]$ group. The term "fluorinated $C_1$-$C_3$-alkylsulfonyl" refers to a fluorinated $C_1$-$C_3$-alkyl group, as defined above, attached via a sulfonyl $[S(O)_2]$ group. The term "fluorinated $C_1$-$C_4$-alkylsulfonyl" refers to a fluorinated $C_1$-$C_4$-alkyl group, as defined above, attached via a sulfonyl $[S(O)_2]$ group. The term "fluorinated $C_1$-$C_6$-alkylsulfonyl" refers to a fluorinated $C_1$-$C_6$-alkyl group, as defined above, attached via a sulfonyl $[S(O)_2]$ group. Fluorinated $C_1$-$C_2$-alkylsulfonyl is, for example, $S(O)_2CH_2F$, $S(O)_2CHF_2$, $S(O)_2CF_3$, 2-fluoroethylsulfonyl, 2,2-difluoroethylsulfonyl, 2,2,2-trifluoroethylsulfonyl, or $S(O)_2C_2F_5$. Fluorinated $C_1$-$C_3$-alkylsulfonyl is additionally, for example, 2-fluoropropylsulfonyl, 3-fluoropropylsulfonyl, 2,2-difluoropropylsulfonyl, 2,3-difluoropropylsulfonyl, 3,3,3-trifluoropropylsulfonyl, $S(O)_2CH_2$—$C_2F_5$, $S(O)_2CF_2$—$C_2F_5$ or 1-($CH_2F$)-2-fluoroethylsulfonyl. Fluorinated $C_1$-$C_4$-alkylsulfonyl is additionally, for example, 4-fluorobutylsulfonyl or nonafluorobutylsulfonyl. Fluorinated $C_1$-$C_6$-alkylsulfonyl is additionally, for example, 5-fluoropentylsulfonyl, undecafluoropentylsulfonyl, 6-fluorohexylsulfonyl or dodecafluorohexylsulfonyl.

$C_1$-$C_4$-Alkylcarbonyl refers to a straight-chain or branched alkyl group having from 1 to 4 carbon atoms), which is bound to the remainder of the molecule via a carbonyl group (CO), such as in acetyl, propionyl, isopropylcarbonyl, butylcarbonyl, sec-butylcarbonyl, isobutylcarbonyl, and tert-butylcarbonyl. $C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonylpentylcarbonyl, hexylcarbonyl and the constitutional isomers thereof.

Fluorinated $C_1$-$C_4$-alkylcarbonyl refers to a straight-chain or branched fluorinated alkyl group having from 1 to 4 carbon atoms as defined above, which is bound to the remainder of the molecule via a carbonyl group (CO). Fluorinated $C_1$-$C_6$-alkylcarbonyl is a straight-chain or branched fluorinated alkyl group having from 1 to 6 carbon atoms as defined above, which is bound to the remainder of the molecule via a carbonyl group (CO). Examples include trifluoromethylcarbonyl, 2,2,2-trifluoroethylcarbonyl and the like.

$C_3$-$C_6$-cycloalkylcarbonyl relates to a $C_3$-$C_6$-cycloalkyl group as defined above which is bound to the remainder of the molecule via a carbonyl group (CO), such as in cyclopropylcarbonyl, cyclobutylcarbonyl, cyclopentylcarbonyl and cyclohexylcarbonyl.

$C_1$-$C_6$-Alkoxycarbonyl refers to a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

Fluorinated $C_1$-$C_6$-alkoxycarbonyl refers to a straight-chain or branched fluorinated alkoxy group having from 1 to 6, especially 1 to 4 carbon atoms (=fluorinated $C_1$-$C_4$-alkoxycarbonyl), in particular 1 to 3 carbon atoms (=fluorinated $C_1$-$C_3$-alkoxycarbonyl) as defined above, which is bound to the remainder of the molecule via a carbonyl group (CO). Examples include trifluoromethoxycarbonyl, 2,2,2-trifluoroethoxycarbonyl and the like.

$C_1$-$C_4$-Alkylcarbonyloxy refers to a straight-chain or branched alkyl group having from 1 to 4 carbon atoms, which is bound to the remainder of the molecule via a carbonyloxy group [C(O)—O—], such as in acet(yl)oxy, propionyloxy, isopropylcarbonyloxy, butylcarbonyloxy, sec-butylcarbonyloxy, isobutylcarbonyloxy, and tert-butylcarbonyloxy. $C_1$-$C_6$-Alkylcarbonyloxy is a straight-chain or branched alkyl group having from 1 to 6 carbon atoms, which is bound to the remainder of the molecule via a carbonyloxy group [C(O—O—]. Examples include, apart those listed above for $C_1$-$C_4$-alkylcarbonyloxy, pentylcarbonyloxy, hexylcarbonyloxy and the constitutional isomers thereof.

Fluorinated $C_1$-$C_4$-alkylcarbonyloxy refers to a straight-chain or branched fluorinated alkyl group having from 1 to 4 carbon atoms as defined above, which is bound to the remainder of the molecule via a carbonyloxy group [C(O)—O—]. Fluorinated $C_1$-$C_6$-alkylcarbonyloxy is a straight-chain or branched fluorinated alkyl group having from 1 to 6 carbon atoms as defined above, which is bound to the remainder of the molecule via a carbonyloxy group [C(O)—O—]. Examples include trifluoromethylcarbonyloxy, 2,2,2-trifluoroethylcarbonyloxy and the like.

Phenyl-$C_1$-$C_2$-alkyl is a phenyl group bound to the remainder of the molecule via a $C_1$-$C_2$-alkyl group. Examples are benzyl, 1-phenylethyl and 2-phenylethyl (phenethyl).

The term "3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members" denotes a 3-, 4-, 5-, 6-, 7- or 8-membered, preferably a 3-, 4-, 5-, 6- or 7-membered saturated, partially unsaturated or maximum unsaturated heteromonocyclic ring containing 1, 2, 3 or 4 (preferably 1, 2 or 3) heteroatoms or heteroatom groups selected from N, O, S, SO and $SO_2$ and optionally also 1 or 2 C=O and/or C=S groups as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. 7- and 8-membered rings cannot be aromatic. They are homoaromatic (7-membered ring, 3 double bonds) or have 4 double bonds (8-membered ring). Partially unsaturated rings contain less than the maximum number of C—C and/or C—N and/or N—N double bond(s) allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

In heterocyclic rings containing N as a ring member this nitrogen atom may either be present as tertiary N formally bound by a double and a single bond (like in pyridyl) or may be present as secondary NH (if N is not part of a ring double bond). In case that N is actually present as NH, and the ring is substituted, the substituent may either be bound to a carbon ring atom or to such a secondary nitrogen ring atom. In case that N is actually present as NH, the ring may either be bound to the remainder of the molecule via a carbon ring atom or such a secondary nitrogen ring atom.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrofuran-2-on-3-yl, tetrahydrofuran-2-on-4-yl, tetrahydrofuran-2-on-5-yl, tetrahydrofuran-2-thion-3-yl, tetrahydrofuran-2-thion-4-yl, tetrahydrofuran- 2-thion-5-yl, tetrahydrothien-2-yl, tetrahydrothien-3-yl, tetrahydrothien-2-on-3-yl, tetrahydrothien-2-on-4-yl, tetrahydrothien-2-on-5-yl, tetrahydrothien-2-thion-3-yl, tetrahydrothien-2-thion-4-yl, tetrahydrothien-2-thion-5-yl, pyrrolidin-1-yl, pyrrolidine-2-on-1-yl, pyrrolidine-2,5-dion-1-yl, pyrrolidine-2-thion-1-yl, pyrrolidin-2-yl, pyrrolidin-3-yl, pyrrolidine-2-on-3-yl, pyrrolidine-2-on-4-yl, pyrrolidine-2-on-5-yl, pyrrolidine-2,5-dion-3-yl, pyrrolidine-2-thion-3-yl, pyrrolidine-2-thion-4-yl, pyrrolidine-2-thion-5-yl, pyrazolidin-1-yl, pyrazolidin-3-yl, pyrazolidin-4-yl, pyrazolidin-5-yl, imidazolidin-1-yl, imidazolidin-2-on-1-yl, imidazolidin-2-thion-1-yl, imidazolidin-2-yl, imidazolidin-4-yl, imidazolidin-2-on-4-yl, imidazolidin-2-thion-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-on-1-yl, piperidin-2,5-dion-1-yl, piperidine-2-thion-1-yl, piperidin-2-yl, piperidin-3-yl, piperidin-2-on-3-yl, piperidin-2,5-dion-3-yl, piperidin-2-thion-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan 2-, 3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6-, 7- or 8-membered saturated heterocyclic ring further include oxocane, thiocane, azocane, [1,3]diazocane, [1,4]diazocane, [1,5]diazocane, [1,5]oxazocane and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of a 3-, 4-, 5-, 6-, 7- or 8-membered partially unsaturated heterocyclic ring further include 1,2,3,4,5,6-hexahydroazocine, 2,3,4,5,6,7-hexahydroazocine, 1,2,3,4,5,8-hexahydroazocine, 1,2,3,4,7,8-hexahydroazocine, 1,2,3,4,5,6-hexahydro-[1,5]diazocine,1,2,3,4,7,8-hexahydro-[1,5]diazocine and the like.

Examples of a 3-, 4-, 5-, 6- or 7-membered maximally unsaturated (including aromatic) heterocyclic ring include 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples of a 3-, 4-, 5-, 6-, 7- or 8-membered maximally unsaturated heterocyclic ring further include [1,3]diazocine, [1,5]diazocine and [1,5]diazocine.

A 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, SO$_2$, C═O and C═S as ring members is either saturated, partially unsaturated and carbocyclic (if it contains only C═O and/or C═S as heteroatom group and no further heteroatoms or heteroatom groups) or saturated, partially unsaturated or maximally unsaturated heterocyclic. Examples are, in addition to the heterocyclic rings mentioned above, carbocyclic rings, such as cyclopropanonyl, cyclobutanonyl, cyclopentanonyl, cyclohexanonyl, cyclohexandionyl, cycloheptanonyl, cyclooctanonyl, cyclopropanthionyl, cyclobutanthionyl, cyclopentanthionyl, cyclohexanthionyl, cyclohexandithionyl, cycloheptanthionyl, cyclooctanthionyl, cyclopropenonyl, cyclopentenonyl, cyclohexenonyl and the like.

Examples of a 4-membered saturated heterocyclic ring containing 1 heteroatom or heteroatom group selected from N, O, S, NO, SO and SO$_2$ as ring member are oxetan-3-yl, oxetan-4-yl, azetidin-1-yl, azetidin-2-yl, azetidin-3-yl, thietan-2-yl, thietan-3-yl, 1-oxothietan-2-yl, 1-oxothietan-3-yl, 1,1-dioxothietan-2-yl and 1,1-dioxothietan-3-yl.

Examples of a 3-, 4-, 5- or 6-membered saturated heterocyclic ring containing 1 or 2 heteroatoms or heteroatom groups independently selected from N, O, S, NO, SO and SO$_2$ as ring members are, apart those listed above for the 4-membered saturated heterocyclic ring containing 1 heteroatom or heteroatom group selected from N, O, S, NO, SO and $SO_2$ as ring member, oxiral-2-yl, aziridin-1-yl, aziridin-2-yl, thiiran-2-yl, 1-oxothiiran-2-yl, 1,1-dioxothiiran-2-yl, tetrahydrofuran-2-yl, tetrahydrofuran-3-yl, tetrahydrothien-2-yl, tetrahydrothien-3-yl, pyrrolidin-1-yl, pyrroldin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl and 1,1-dioxothiomorpholin-4-yl.

The remarks made above and in the following with respect to preferred aspects of the invention, e.g. to preferred meanings of the variables $R^1$, $R^2$, $R^{3a}$, $R^{3b}$, $R^{4a}$, $R^{4b}$, $R^{5a}$, $R^{5b}$, $R^6$, $R^7$, $R^8$, $R^9$, $R^{10}$, $R^{11a}$, $R^{11b}$, a and b of compounds I, to preferred compounds I and to preferred embodiments of the method or the use according to the invention, apply in each case on their own or in particular to combinations thereof.

In a preferred embodiment, $R^1$ is selected from hydrogen and $C_1$-$C_6$-alkyl, in particular from hydrogen and methyl, and is specifically hydrogen.

In a preferred embodiment, $R^2$ is selected from cyano, nitro, $C_1$-$C_6$-alkyl, fluorinated $C_1$-$C_6$-alkyl, $C_1$-$C_6$-alkoxy-$C_1$-$C_4$-alkyl and fluorinated $C_1$-$C_6$-alkoxy-$C_1$-$C_4$-alkyl, more preferably from $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl, even more preferably from $C_1$-$C_6$-alkyl and fluorinated $C_1$-$C_6$-alkyl, in particular from methyl, ethyl, propyl, isopropyl and $CF_3$, more particularly from methyl, ethyl and $CF_3$, and is specifically methyl or $CF_3$. Among $C_1$-$C_6$-alkoxy-$C_1$-$C_4$-alkyl, $C_1$-$C_4$-alkoxy-$C_1$-$C_4$-alkyl, fluorinated $C_1$-$C_6$-alkoxy-$C_1$-$C_4$-alkyl and fluorinated $C_1$-$C_4$-alkoxy-$C_1$-$C_4$-alkyl radicals $R^2$, preference is given to $CH_2OCH_3$, $CH_2CH_2OCH_3$, $CH_2OCH_2CH_3$, $CH_2CH_2OCH_2CH_3$, $CH_2OCF_3$, $CH_2CH_2OCF_3$, $CH_2OCHF_2$ and $CH_2CH_2OCHF_2$.

In a preferred embodiment, $R^{3a}$ and $R^{3b}$, independently of each other, are selected from hydrogen, cyano, nitro, $C_1$-$C_6$-alkyl and fluorinated $C_1$-$C_6$-alkyl. More preferably, $R^{3a}$ is selected from hydrogen, cyano, nitro, $C_1$-$C_6$-alkyl and fluorinated $C_1$-$C_6$-alkyl, and $R^{3b}$ is hydrogen. Even more preferably, $R^{3a}$ is selected from hydrogen and methyl and $R^{3b}$ is hydrogen. In particular, both $R^{3a}$ and $R^{3b}$ are hydrogen.

In a preferred embodiment, $R^{4a}$ and $R^{4b}$, independently of each other, are selected from hydrogen, $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl, or form together a group =O, or form together a group —$(CH_2)_m$—, where m is 2, 3 or 4, in particular 2 or 3, especially 2, thus forming together a spiro-bound ring. More preferably, $R^{4a}$ is selected from hydrogen, $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl and $R^{4b}$ is hydrogen, or $R^{4a}$ and $R^{4b}$ are methyl, or $R^{4a}$ and $R^{4b}$ form together a group —$(CH_2)_m$—, where m is 2, 3 or 4, in particular 2 or 3, especially 2, thus forming together a spiro-bound ring. In a particular embodiment, they are hydrogen.

In a preferred embodiment, $R^{5a}$ is selected from hydrogen, halogen, $C_1$-$C_6$-alkyl, fluorinated $C_1$-$C_6$-alkyl and $C_1$-$C_6$-alkoxy-$C_1$-$C_4$-alkyl and $R^{5b}$ is hydrogen. In particular, $R^{5a}$ is hydrogen or methyl, specifically hydrogen, and $R^{5b}$ is hydrogen.

Among $C_1$-$C_6$-alkoxy-$C_1$-$C_4$-alkyl, $C_1$-$C_4$-alkoxy-$C_1$-$C_4$-alkyl, fluorinated $C_1$-$C_6$-alkoxy-$C_1$-$C_4$-alkyl and fluorinated $C_1$-$C_4$-alkoxy-$C_1$-$C_4$-alkyl radicals $R^{4a}$, $R^{4b}$ and $R^{5b}$ preference is given to $CH_2OCH_3$, $CH_2CH_2OCH_3$, $CH_2OCH_2CH_3$, $CH_2CH_2OCH_2CH_3$, $CH_2OCF_3$, $CH_2CH_2OCF_3$, $CH_2OCHF_2$ and $CH_2CH_2OCHF_2$.

In one embodiment, $R^6$ is $C_3$-$C_6$-cycloalkyl which may carry one or more, in particular one, radicals $R^8$.

In another embodiment, $R^6$ is a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$, and optionally also 1 or 2 groups C=O and/or C=S, as ring members, where the heterocyclic ring may be substituted with one or more substituents $R^{10}$.

As a substituent on a cycloalkyl radical $R^6$, preferably each $R^8$ is independently selected from the group consisting of halogen, cyano, $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl. Among $C_1$-$C_4$-alkoxy-$C_1$-$C_4$-alkyl and fluorinated $C_1$-$C_4$-alkoxy-$C_1$-$C_4$-alkyl radicals $R^8$, preference is given to $CH_2OCH_3$, $CH_2CH_2OCH_3$, $CH_2OCH_2CH_3$, $CH_2CH_2OCH_2CH_3$, $CH_2OCF_3$, $CH_2CH_2OCF_3$, $CH_2OCHF_2$ and $CH_2CH_2OCHF_2$. In particular, $R^8$ is halogen, specifically F.

In a preferred embodiment, $R^6$ is unsubstituted $C_3$-$C_6$-cycloalkyl; i.e. is selected from cyclopropyl, cyclobutyl, cyclopentyl and cyclohexyl. In another preferred embodiment, $R^6$ is fluorinated $C_3$-$C_6$-cycloalkyl, such as 1-fluorocyclopropyl, 2-fluorocyclopropyl, 2,2-difluorocyclopropyl, 1-fluorocyclobutyl, 2-fluorocyclobutyl, 3-fluorocyclobutyl, 2,2-difluorocyclobutyl, 3,3-difluorocyclobutyl and the like. More preferably, $R^6$ is selected from cyclopropyl, cyclobutyl, cyclopentyl, cyclohexyl, 2,2-difluorocyclopropyl or 3,3-difluorocyclobutyl. In particular, $R^6$ is selected from cyclopropyl and cyclobutyl, and is particularly preferably cyclopropyl. In another particular embodiment $R^6$ is 2,2-difluorocyclopropyl.

In an alternatively preferred embodiment, $R^6$ is a 3-, 4-, 5- or 6-membered saturated heterocyclic ring containing 1 or 2 heteroatoms or heteroatom groups independently selected from N, O, S, NO, SO and $SO_2$ as ring members, where the heterocyclic ring may be substituted with one or more substituents $R^{10}$, where $R^{10}$ has one of the above general or, in particular, one of the below preferred meanings.

In an alternative particular embodiment, $R^6$ is a 4-membered saturated heterocyclic ring containing 1 heteroatom or heteroatom group selected from N, O, S, NO, SO and $SO_2$, in particular from O, as ring member, where the heterocyclic ring may be substituted with one or more substituents $R^{10}$, where $R^{10}$ has one of the above general or, in particular, one of the below preferred meanings. Specifically, $R^6$ is oxetan-3-yl which may be substituted with one or more, especially one, substituents $R^{10}$, where $R^{10}$ has one of the above general or, in particular, one of the below preferred meanings.

In an alternative particular embodiment, $R^6$ is a 5- or 6-membered saturated heterocyclic ring containing 1 heteroatom or heteroatom group selected from N, O, S, NO, SO and SO$_2$, in particular from O, as ring member, where the heterocyclic ring may be substituted with one or more substituents R$^{10}$, where R$^{10}$ has one of the above general or, in particular, one of the below preferred meanings. Specifically, R$^6$ is tetrahydrofuran-3-yl or tetrahydropyran-4-yl which may be substituted with one or more, especially one, substituents R$^{10}$, where R$^{10}$ has one of the above general or, in particular, one of the below preferred meanings.

As a substituent on a heterocyclic ring R$^6$, each R$^{10}$ is independently preferably selected from the group consisting of halogen, cyano, C$_1$-C$_4$-alkyl, fluorinated C$_1$-C$_4$-alkyl, C$_1$-C$_4$-alkoxy and fluorinated C$_1$-C$_4$-alkoxy, more preferably from F, Cl, cyano, CH$_3$, CF$_3$, OCH$_3$ and OCF$_3$, and in particular from F, CH$_3$, CF$_3$, OCH$_3$ and OCF$_3$. Specifically R$^{10}$ is CH$_3$.

In a preferred embodiment, each R$^7$ is independently selected from the group consisting of halogen, cyano, nitro, hydroxyl, C$_1$-C$_6$-alkyl, fluorinated C$_1$-C$_6$-alkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy and fluorinated C$_1$-C$_6$-alkoxy. More preferably, each R$^7$ is independently selected from halogen, C$_1$-C$_4$-alkyl, fluorinated C$_1$-C$_4$-alkyl, C$_1$-C$_4$-alkoxy and fluorinated C$_1$-C$_4$-alkoxy, and is in particular fluorine. In an alternative embodiment, each R$^7$ is independently selected from the group consisting of cyano and C$_1$-C$_4$-alkoxy-C$_1$-C$_4$-alkyl.

In a preferred embodiment, a is 0 or 1. If a is 1, R$^2$ is preferably bound in β-position to the nitrogen ring atom carrying R$^1$.

In particular, a is 0 if R$^6$ is carbocyclic, i.e. C$_3$-C$_6$-cycloalkyl which may carry one or more radicals R$^8$; and a is 0 or 1 if R$^6$ is heterocyclic, i.e. a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and SO$_2$, and optionally also 1 or 2 groups C=O and/or C=S, as ring members, where the heterocyclic ring may be substituted with one or more substituents R$^{10}$.

In a preferred embodiment, b is 0 or 1 and specifically 0.

If not specified otherwise in a specific context, R$^9$, R$^{10}$, R$^{11a}$ and R$^{11b}$ have following preferred meanings:

Preferably each R$^9$ is independently selected from the group consisting of hydrogen, hydroxyl, C$_1$-C$_6$-alkyl, fluorinated C$_1$-C$_6$-alkyl, C$_1$-C$_6$-hydroxyalkyl, C$_3$-C$_6$-cycloalkyl, fluorinated C$_3$-C$_6$-cycloalkyl, C$_1$-C$_6$-alkoxy, fluorinated C$_1$-C$_6$-alkoxy, and —NR$^{11a}$R$^{11b}$, where R$^{11a}$ and R$^{11b}$ have one of the above general or, in particular, one of the below preferred meanings. In particular, each R$^9$ is independently selected from the group consisting of hydrogen, C$_1$-C$_4$-alkyl, fluorinated C$_1$-C$_2$-alkyl, C$_1$-C$_4$-hydroxyalkyl, C$_1$-C$_4$-alkoxy, fluorinated C$_1$-C$_2$-alkoxy, and —NR$^{11a}$R$^{11b}$, where R$^{11a}$ and R$^{11b}$ have one of the above general or, in particular, one of the below preferred meanings.

Preferably, each R$^{10}$ is independently selected from the group consisting of halogen, cyano, C$_1$-C$_4$-alkyl, fluorinated C$_1$-C$_4$-alkyl, C$_1$-C$_4$-alkoxy and fluorinated C$_1$-C$_4$-alkoxy, more preferably from F, Cl, cyano, CH$_3$, CF$_3$, OCH$_3$ and OCF$_3$, and in particular from F, CH$_3$, CF$_3$, OCH$_3$ and OCF$_3$.

Preferably, R$^{11a}$ and R$^{11b}$, independently of each other and independently of each occurrence, are selected from the group consisting of hydrogen, C$_1$-C$_6$-alkyl, fluorinated C$_1$-C$_6$-alkyl, C$_1$-C$_6$-alkylcarbonyl and fluorinated C$_1$-C$_6$-alkylcarbonyl.

In a particular embodiment, the compounds of the invention are compounds of formula I.1

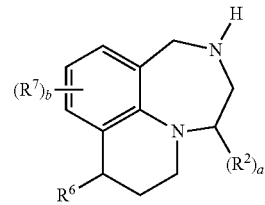

wherein R$^2$, R$^6$, R$^7$ and b have one of the above general or, in particular, one of the above preferred meanings, and a is 0 or 1.

In a more particular embodiment, the compounds of the invention are compounds of formula I.1.1

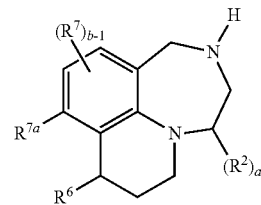

wherein

R$^{7a}$ is H, Cl, F or methyl, in particular H or F, specifically H;

a is 0 or 1; and

R$^2$, R$^6$, R$^7$ and b have one of the above general or, in particular, one of the above preferred meanings.

In compounds I.1.1 (b−1) is preferably 0.

In compounds I.1 and I.1.1 R$^2$ is preferably methyl.

In compounds I.1 and I.1.1 a is preferably 0 if R$^6$ is a carbocyclic (i.e. cycloalkyl) radical, and is 0 or 1 if R$^6$ is heterocyclic.

Examples of preferred compounds are compounds of the following formulae Ia.1 to Ia.36, where the variables have one of the general or preferred meanings given above. Examples of preferred compounds are the individual compounds compiled in the tables 1 to 28080 below. Moreover, the meanings mentioned below for the individual variables in the tables are per se, independently of the combination in which they are mentioned, a particularly preferred embodiment of the substituents in question.

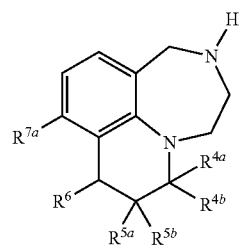

Ia.1

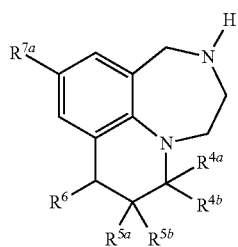
Ia.2
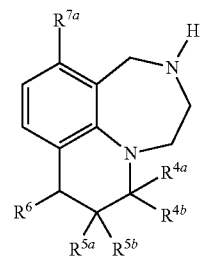
Ia.3
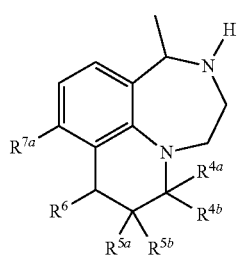
Ia.4
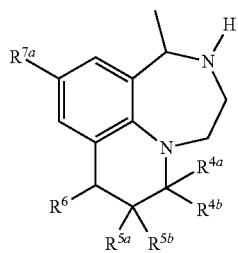
Ia.5
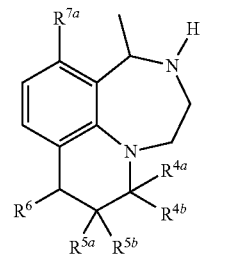
Ia.6
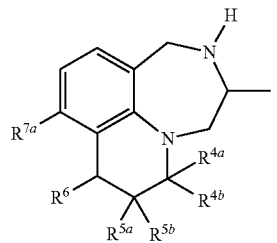
Ia.7
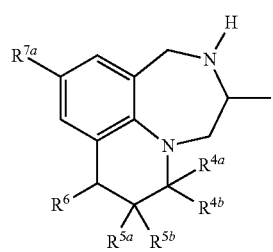
Ia.8
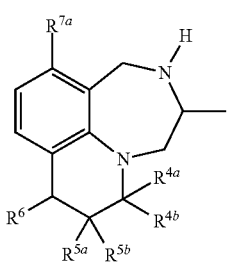
Ia.9
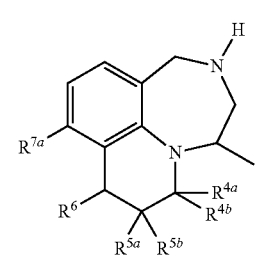
Ia.10
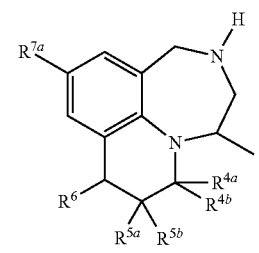
Ia.11
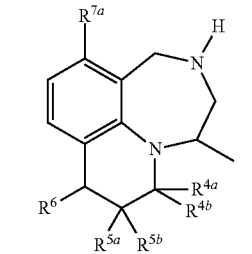
Ia.12
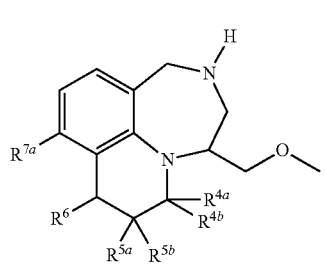
Ia.13

-continued

Ia.14

Ia.15

Ia.16

Ia.17

Ia.18

Ia.19

-continued

Ia.20

Ia.21

Ia.22

Ia.23

Ia.24

Ia.25

Ia.26 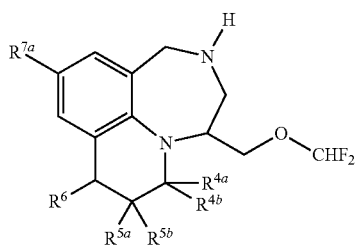

Ia.27 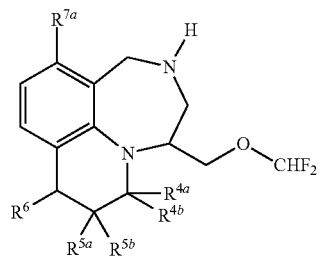

Ia.28 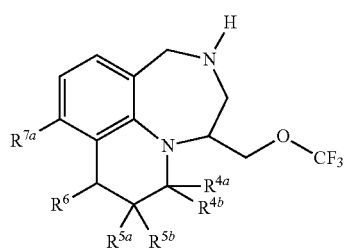

Ia.29 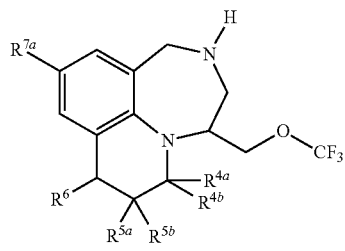

Ia.30 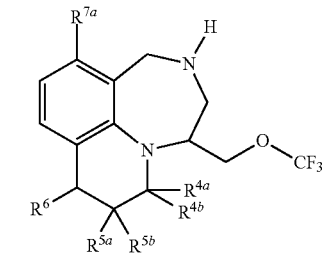

Ia.31 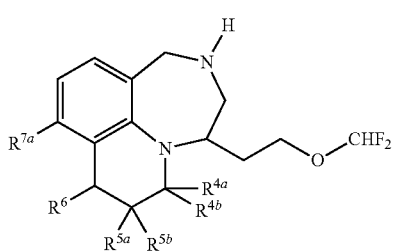

Ia.32 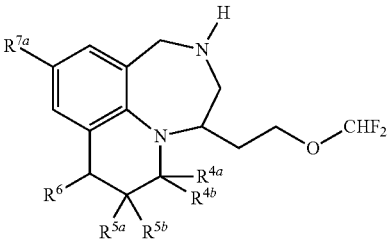

Ia.33 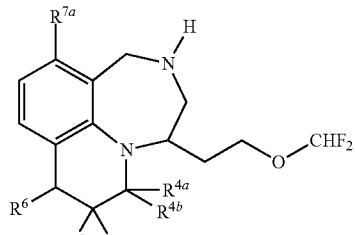

Ia.34 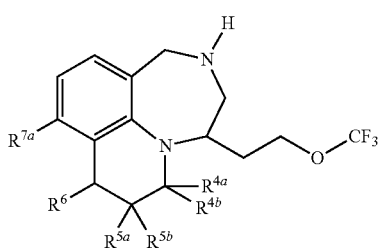

Ia.35 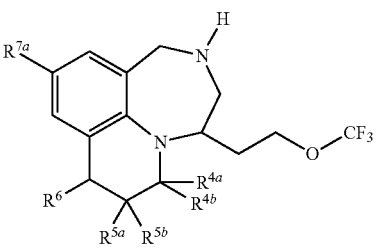

Ia.36 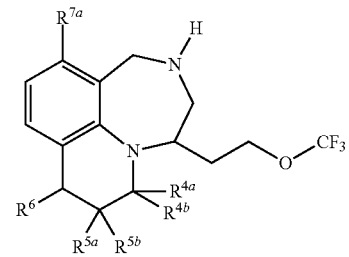

Table 1
Compounds of the formula Ia.1 in which $R^{4a}$ is H, $R^{4b}$ is H, $R^6$ is cyclopropyl and the combination of $R^{5a}$, $R^{5b}$ and $R^{7a}$ for a compound corresponds in each case to one row of Table A.

Table 2
Compounds of the formula Ia.1 in which $R^{4a}$ is H, $R^{4b}$ is H, $R^6$ is 1-fluorocyclopropyl and the combination of $R^{5a}$, $R^{5b}$ and $R^{7a}$ for a compound corresponds in each case to one row of Table A.

Table 3
Compounds of the formula Ia.1 in which $R^{4a}$ is H, $R^{4b}$ is H, $R^6$ is 2-fluorocyclopropyl and the combination of $R^{5a}$, $R^{5b}$ and $R^{7a}$ for a compound corresponds in each case to one row of Table A.

Table 4
Compounds of the formula Ia.1 in which $R^{4a}$ is H, $R^{4b}$ is H, $R^6$ is 2,2-difluorocyclopropyl and the combination of $R^{5a}$, $R^{5b}$ and $R^{7a}$ for a compound corresponds in each case to one row of Table A.

Table 5
Compounds of the formula Ia.1 in which $R^{4a}$ is H, $R^{4b}$ is H, $R^6$ is cyclobutyl and the combination of $R^{5a}$, $R^{5b}$ and $R^{7a}$ for a compound corresponds in each case to one row of Table A.

Table 6
Compounds of the formula Ia.1 in which $R^{4a}$ is H, $R^{4b}$ is H, $R^6$ is 1-fluorocyclobutyl and the combination of $R^{5a}$, $R^{5b}$ and $R^{7a}$ for a compound corresponds in each case to one row of Table A.

Table 7
Compounds of the formula Ia.1 in which $R^{4a}$ is H, $R^{4b}$ is H, $R^6$ is 2-fluorocyclobutyl and the combination of $R^{5a}$, $R^{5b}$ and $R^{7a}$ for a compound corresponds in each case to one row of Table A.

Table 8
Compounds of the formula Ia.1 in which $R^{4a}$ is H, $R^{4b}$ is H, $R^6$ is 3-fluorocyclobutyl and the combination of $R^{5a}$, $R^{5b}$ and $R^{7a}$ for a compound corresponds in each case to one row of Table A.

Table 9
Compounds of the formula Ia.1 in which $R^{4a}$ is H, $R^{4b}$ is H, $R^6$ is 2,2-difluorocyclobutyl and the combination of $R^{5a}$, $R^{5b}$ and $R^{7a}$ for a compound corresponds in each case to one row of Table A.

Table 10
Compounds of the formula Ia.1 in which $R^{4a}$ is H, $R^{4b}$ is H, $R^6$ is 3,3-difluorocyclobutyl and the combination of $R^{5a}$, $R^{5b}$ and $R^{7a}$ for a compound corresponds in each case to one row of Table A.

Table 11
Compounds of the formula Ia.1 in which $R^{4a}$ is H, $R^{4b}$ is H, $R^6$ is cyclopentyl and the combination of $R^{5a}$, $R^{5b}$ and $R^{7a}$ for a compound corresponds in each case to one row of Table A.

Table 12
Compounds of the formula Ia.1 in which $R^{4a}$ is H, $R^{4b}$ is H, $R^6$ is 1-fluorocyclopentyl and the combination of $R^{5a}$, $R^{5b}$ and $R^{7a}$ for a compound corresponds in each case to one row of Table A.

Table 13
Compounds of the formula Ia.1 in which $R^{4a}$ is H, $R^{4b}$ is H, $R^6$ is 2-fluorocyclopentyl and the combination of $R^{5a}$, $R^{5b}$ and $R^{7a}$ for a compound corresponds in each case to one row of Table A.

Table 14
Compounds of the formula Ia.1 in which $R^{4a}$ is H, $R^{4b}$ is H, $R^6$ is 3-fluorocyclopentyl and the combination of $R^{5a}$, $R^{5b}$ and $R^{7a}$ for a compound corresponds in each case to one row of Table A.

Table 15
Compounds of the formula Ia.1 in which $R^{4a}$ is H, $R^{4b}$ is H, $R^6$ is 2,2-difluorocyclopentyl and the combination of $R^{5a}$, $R^{5b}$ and $R^{7a}$ for a compound corresponds in each case to one row of Table A.

Table 16
Compounds of the formula Ia.1 in which $R^{4a}$ is H, $R^{4b}$ is H, $R^6$ is 3,3-difluorocyclopentyl and the combination of $R^{5a}$, $R^{5b}$ and $R^{7a}$ for a compound corresponds in each case to one row of Table A.

Table 17
Compounds of the formula Ia.1 in which $R^{4a}$ is H, $R^{4b}$ is H, $R^6$ is cyclohexyl and the combination of $R^{5a}$, $R^{5b}$ and $R^{7a}$ for a compound corresponds in each case to one row of Table A.

Table 18
Compounds of the formula Ia.1 in which $R^{4a}$ is H, $R^{4b}$ is H, $R^6$ is 1-fluorocyclohexyl and the combination of $R^{5a}$, $R^{5b}$ and $R^{7a}$ for a compound corresponds in each case to one row of Table A.

Table 19
Compounds of the formula Ia.1 in which $R^{4a}$ is H, $R^{4b}$ is H, $R^6$ is 2-fluorocyclohexyl and the combination of $R^{5a}$, $R^{5b}$ and $R^{7a}$ for a compound corresponds in each case to one row of Table A.

Table 20
Compounds of the formula Ia.1 in which $R^{4a}$ is H, $R^{4b}$ is H, $R^6$ is 3-fluorocyclohexyl and the combination of $R^{5a}$, $R^{5b}$ and $R^{7a}$ for a compound corresponds in each case to one row of Table A.

Table 21
Compounds of the formula Ia.1 in which $R^{4a}$ is H, $R^{4b}$ is H, $R^6$ is 4-fluorocyclohexyl and the combination of $R^{5a}$, $R^{5b}$ and $R^{7a}$ for a compound corresponds in each case to one row of Table A.

Table 22
Compounds of the formula Ia.1 in which $R^{4a}$ is H, $R^{4b}$ is H, $R^6$ is aziridin-1-yl and the combination of $R^{5a}$, $R^{5b}$ and $R^{7a}$ for a compound corresponds in each case to one row of Table A.

Table 23
Compounds of the formula Ia.1 in which $R^{4a}$ is H, $R^{4b}$ is H, $R^6$ is 1-(oxetan-3-yl)-aziridin-2-yl and the combination of $R^{5a}$, $R^{5b}$ and $R^{7a}$ for a compound corresponds in each case to one row of Table A.

Table 24
Compounds of the formula Ia.1 in which $R^{4a}$ is H, $R^{4b}$ is H, $R^6$ is 1-(tetrahydrofuran-3-yl)-aziridin-2-yl and the combination of $R^{5a}$, $R^{5b}$ and $R^{7a}$ for a compound corresponds in each case to one row of Table A.

Table 25
Compounds of the formula Ia.1 in which $R^{4a}$ is H, $R^{4b}$ is H, $R^6$ is oxiran-2-yl and the combination of $R^{5a}$, $R^{5b}$ and $R^{7a}$ for a compound corresponds in each case to one row of Table A.

Table 26
Compounds of the formula Ia.1 in which $R^{4a}$ is H, $R^{4b}$ is H, $R^6$ is azetidin-1-yl and the combination of $R^{5a}$, $R^{5b}$ and $R^{7a}$ for a compound corresponds in each case to one row of Table A.

Table 27
Compounds of the formula Ia.1 in which $R^{4a}$ is H, $R^{4b}$ is H, $R^6$ is 1-(oxetan-3-yl)-azetidin-2-yl and the combination of $R^{5a}$, $R^{5b}$ and $R^{7a}$ for a compound corresponds in each case to one row of Table A.

Table 28
Compounds of the formula Ia.1 in which $R^{4a}$ is H, $R^{4b}$ is H, $R^6$ is 1-(tetrahydrofuran-3-yl)-azetidin-2-yl and the combination of $R^{5a}$, $R^{5b}$ and $R^{7a}$ for a compound corresponds in each case to one row of Table A.

Table 29
Compounds of the formula Ia.1 in which $R^{4a}$ is H, $R^{4b}$ is H, $R^6$ is 1-(oxetan-3-yl)-azetidin-3-yl and the combination of $R^{5a}$, $R^{5b}$ and $R^{7a}$ for a compound corresponds in each case to one row of Table A.

Table 30
Compounds of the formula Ia.1 in which $R^{4a}$ is H, $R^{4b}$ is H, $R^6$ is 1-(tetrahydrofuran-3-yl)-azetidin-2-yl and the com- Table 31
Compounds of the formula Ia.1 in which $R^{4a}$ is H, $R^{4b}$ is H, $R^6$ is oxetan-2-yl and the combination of $R^{5a}$, $R^{5b}$ and $R^{7a}$ for a compound corresponds in each case to one row of Table A.

Table 32
Compounds of the formula Ia.1 in which $R^{4a}$ is H, $R^{4b}$ is H, $R^6$ is oxetan-3-yl and the combination of $R^{5a}$, $R^{5b}$ and $R^{7a}$ for a compound corresponds in each case to one row of Table A.

Table 33
Compounds of the formula Ia.1 in which $R^{4a}$ is H, $R^{4b}$ is H, $R^6$ is 3-methyloxetan-2-yl and the combination of $R^{5a}$, $R^{5b}$ and $R^{7a}$ for a compound corresponds in each case to one row of Table A.

Table 34
Compounds of the formula Ia.1 in which $R^{4a}$ is H, $R^{4b}$ is H, $R^6$ is 3-methyloxetan-3-yl and the combination of $R^{5a}$, $R^{5b}$ and $R^{7a}$ for a compound corresponds in each case to one row of Table A.

Table 35
Compounds of the formula Ia.1 in which $R^{4a}$ is H, $R^{4b}$ is H, $R^6$ is 2-methyloxetan-3-yl and the combination of $R^{5a}$, $R^{5b}$ and $R^{7a}$ for a compound corresponds in each case to one row of Table A.

Table 36
Compounds of the formula Ia.1 in which $R^{4a}$ is H, $R^{4b}$ is H, $R^6$ is pyrrolidin-1-yl and the combination of $R^{5a}$, $R^{5b}$ and $R^{7a}$ for a compound corresponds in each case to one row of Table A.

Table 37
Compounds of the formula Ia.1 in which $R^{4a}$ is H, $R^{4b}$ is H, $R^6$ is 1-(oxetan-3-yl)-pyrrolidin-2-yl and the combination of $R^{5a}$, $R^{5b}$ and $R^{7a}$ for a compound corresponds in each case to one row of Table A.

Table 38
Compounds of the formula Ia.1 in which $R^{4a}$ is H, $R^{4b}$ is H, $R^6$ is 1-(tetrahydrofuran-3-yl)-azetidin-2-yl and the combination of $R^{5a}$, $R^{5b}$ and $R^{7a}$ for a compound corresponds in each case to one row of Table A.

Table 39
Compounds of the formula Ia.1 in which $R^{4a}$ is H, $R^{4b}$ is H, $R^6$ is 1-(oxetan-3-yl)-pyrrolidin-3-yl and the combination of $R^{5a}$, $R^{5b}$ and $R^{7a}$ for a compound corresponds in each case to one row of Table A.

Table 40
Compounds of the formula Ia.1 in which $R^{4a}$ is H, $R^{4b}$ is H, $R^6$ is 1-(tetrahydrofuran-3-yl)-pyrrolidin-3-yl and the combination of $R^{5a}$, $R^{5b}$ and $R^{7a}$ for a compound corresponds in each case to one row of Table A.

Table 41
Compounds of the formula Ia.1 in which $R^{4a}$ is H, $R^{4b}$ is H, $R^6$ is tetrahydrofuran-2-yl and the combination of $R^{5a}$, $R^{5b}$ and $R^{7a}$ for a compound corresponds in each case to one row of Table A.

Table 42
Compounds of the formula Ia.1 in which $R^{4a}$ is H, $R^{4b}$ is H, $R^6$ is tetrahydrofuran-3-yl and the combination of $R^{5a}$, $R^{5b}$ and $R^{7a}$ for a compound corresponds in each case to one row of Table A.

Table 43
Compounds of the formula Ia.1 in which $R^{4a}$ is H, $R^{4b}$ is H, $R^6$ is 3-(oxetan-3-yl)-oxazolidin-2-yl and the combination of $R^{5a}$, $R^{5b}$ and $R^{7a}$ for a compound corresponds in each case to one row of Table A.

Table 44
Compounds of the formula Ia.1 in which $R^{4a}$ is H, $R^{4b}$ is H, $R^6$ is oxazolidin-3-yl and the combination of $R^{5a}$, $R^{5b}$ and $R^{7a}$ for a compound corresponds in each case to one row of Table A.

Table 45
Compounds of the formula Ia.1 in which $R^{4a}$ is H, $R^{4b}$ is H, $R^6$ is 3-(oxetan-3-yl)-oxazolidin-4-yl and the combination of $R^{5a}$, $R^{5b}$ and $R^{7a}$ for a compound corresponds in each case to one row of Table A.

Table 46
Compounds of the formula Ia.1 in which $R^{4a}$ is H, $R^{4b}$ is H, $R^6$ is 3-(oxetan-3-yl)-oxazolidin-5-yl and the combination of $R^{5a}$, $R^{5b}$ and $R^{7a}$ for a compound corresponds in each case to one row of Table A.

Table 47
Compounds of the formula Ia.1 in which $R^{4a}$ is H, $R^{4b}$ is H, $R^6$ is isoxazolidin-2-yl and the combination of $R^{5a}$, $R^{5b}$ and $R^{7a}$ for a compound corresponds in each case to one row of Table A.

Table 48
Compounds of the formula Ia.1 in which $R^{4a}$ is H, $R^{4b}$ is H, $R^6$ is 2-(oxetan-3-yl)-isoxazolidin-3-yl and the combination of $R^{5a}$, $R^{5b}$ and $R^{7a}$ for a compound corresponds in each case to one row of Table A.

Table 49
Compounds of the formula Ia.1 in which $R^{4a}$ is H, $R^{4b}$ is H, $R^6$ is 2-(oxetan-3-yl)-isoxazolidin-4-yl and the combination of $R^{5a}$, $R^{5b}$ and $R^{7a}$ for a compound corresponds in each case to one row of Table A.

Table 50
Compounds of the formula Ia.1 in which $R^{4a}$ is H, $R^{4b}$ is H, $R^6$ is 2-(oxetan-3-yl)-isoxazolidin-5-yl and the combination of $R^{5a}$, $R^{5b}$ and $R^{7a}$ for a compound corresponds in each case to one row of Table A.

Table 51
Compounds of the formula Ia.1 in which $R^{4a}$ is H, $R^{4b}$ is H, $R^6$ is piperidin-1-yl and the combination of $R^{5a}$, $R^{5b}$ and $R^{7a}$ for a compound corresponds in each case to one row of Table A.

Table 52
Compounds of the formula Ia.1 in which $R^{4a}$ is H, $R^{4b}$ is H, $R^6$ is 4-(oxetan-3-yl)-piperazine-1-yl and the combination of $R^{5a}$, $R^{5b}$ and $R^{7a}$ for a compound corresponds in each case to one row of Table A.

Table 53
Compounds of the formula Ia.1 in which $R^{4a}$ is H, $R^{4b}$ is H, $R^6$ is 4-(tetrahydrofuran-3-yl)-piperazine-1-yl and the combination of $R^{5a}$, $R^{5b}$ and $R^{7a}$ for a compound corresponds in each case to one row of Table A.

Table 54
Compounds of the formula Ia.1 in which $R^{4a}$ is H, $R^{4b}$ is H, $R^6$ is morpholin-4-yl and the combination of $R^{5a}$, $R^{5b}$ and $R^{7a}$ for a compound corresponds in each case to one row of Table A.

Table 55
Compounds of the formula Ia.1 in which $R^{4a}$ is H, $R^{4b}$ is H, $R^6$ is tetrahydropyran-2-yl and the combination of $R^{5a}$, $R^{5b}$ and $R^{7a}$ for a compound corresponds in each case to one row of Table A.

Table 56
Compounds of the formula Ia.1 in which $R^{4a}$ is H, $R^{4b}$ is H, $R^6$ is tetrahydropyran-3-yl and the combination of $R^{5a}$, $R^{5b}$ and $R^{7a}$ for a compound corresponds in each case to one row of Table A.

Table 57
Compounds of the formula Ia.1 in which $R^{4a}$ is H, $R^{4b}$ is H, $R^6$ is tetrahydropyran-4-yl and the combination of $R^{5a}$, $R^{5b}$ and $R^{7a}$ for a compound corresponds in each case to one row of Table A.

Table 58
Compounds of the formula Ia.1 in which $R^{4a}$ is H, $R^{4b}$ is H, $R^6$ is 1,3-dioxan-2-yl and the combination of $R^{5a}$, $R^{5b}$ and $R^{7a}$ for a compound corresponds in each case to one row of Table A.

Table 59
Compounds of the formula Ia.1 in which $R^{4a}$ is H, $R^{4b}$ is H, $R^6$ is 1,3-dioxan-4-yl and the combination of $R^{5a}$, $R^{5b}$ and $R^{7a}$ for a compound corresponds in each case to one row of Table A.

Table 60
Compounds of the formula Ia.1 in which $R^{4a}$ is H, $R^{4b}$ is H, $R^6$ is 1,4-dioxan-2-yl and the combination of $R^{5a}$, $R^{5b}$ and $R^{7a}$ for a compound corresponds in each case to one row of Table A.

Tables 61 to 120
Compounds of the formula Ia.1 in which $R^{4a}$ is methyl, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 121 to 180
Compounds of the formula Ia.1 in which $R^{4a}$ is ethyl, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 181 to 240
Compounds of the formula Ia.1 in which $R^{4a}$ is $CH_2OCH_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 241 to 300
Compounds of the formula Ia.1 in which $R^{4a}$ is $CH_2OCH_2CH_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 301 to 360
Compounds of the formula Ia.1 in which $R^{4a}$ is $CH_2CH_2OCH_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 361 to 420
Compounds of the formula Ia.1 in which $R^{4a}$ is $CH_2CH_2OCH_2CH_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 421 to 480
Compounds of the formula Ia.1 in which $R^{4a}$ is $CH_2OCHF_2$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 481 to 540
Compounds of the formula Ia.1 in which $R^{4a}$ is $CH_2OCF_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 541 to 600
Compounds of the formula Ia.1 in which $R^{4a}$ is $CH_2CH_2OCHF_2$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 601 to 660
Compounds of the formula Ia.1 in which $R^{4a}$ is $CH_2CH_2OCF_3$, $R^{4b}$ is H, $R^6$ is as defined in tables 1 to 60 and the combination of $R^{5a}$, $R^{5b}$ and $R^{7a}$ for a compound corresponds in each case to one row of Table A.

Tables 661 to 720
Compounds of the formula Ia.1 in which $R^{4a}$ is methyl, $R^{4b}$ is methyl, $R^6$ is as defined in tables 1 to 60 and the combination of $R^{5a}$, $R^{5b}$ and $R^{7a}$ for a compound corresponds in each case to one row of Table A.

Tables 721 to 780
Compounds of the formula Ia.1 in which $R^{4a}$ and $R^{4b}$ form together —$CH_2$—$CH_2$—, $R^6$ is as defined in tables 1 to 60 and the combination of $R^{5a}$, $R^{5b}$ and $R^{7a}$ for a compound corresponds in each case to one row of Table A.

Tables 781 to 1560
Compounds of the formula Ia.2 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 1561 to 2340
Compounds of the formula Ia.3 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 2341 to 3120
Compounds of the formula Ia.4 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 3121 to 3900
Compounds of the formula Ia.5 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 3901 to 4680
Compounds of the formula Ia.6 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 4681 to 5460
Compounds of the formula Ia.7 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 5461 to 6240
Compounds of the formula Ia.8 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 6241 to 7020
Compounds of the formula Ia.9 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 7021 to 7800
Compounds of the formula Ia.10 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 7801 to 8580
Compounds of the formula Ia.11 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 8581 to 9360
Compounds of the formula Ia.12 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 9361 to 10140

Compounds of the formula Ia.13 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 10141 to 10920

Compounds of the formula Ia.14 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 10921 to 11700

Compounds of the formula Ia.15 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 11701 to 12480

Compounds of the formula Ia.16 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 12481 to 13260

Compounds of the formula Ia.17 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 13261 to 14040

Compounds of the formula Ia.18 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 14041 to 14820

Compounds of the formula Ia.19 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 14821 to 15600

Compounds of the formula Ia.20 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 15601 to 16380

Compounds of the formula Ia.21 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 16381 to 17160

Compounds of the formula Ia.22 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 17161 to 17940

Compounds of the formula Ia.23 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 17941 to 18720

Compounds of the formula Ia.24 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 18721 to 19500

Compounds of the formula Ia.25 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 19501 to 20280

Compounds of the formula Ia.26 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 20281 to 21060

Compounds of the formula Ia.27 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 21061 to 21840

Compounds of the formula Ia.28 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 21841 to 22620

Compounds of the formula Ia.29 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 22621 to 23400

Compounds of the formula Ia.30 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 23401 to 24180

Compounds of the formula Ia.31 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 24181 to 24960

Compounds of the formula Ia.32 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 24961 to 25740

Compounds of the formula Ia.33 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 25741 to 26520

Compounds of the formula Ia.34 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 26521 to 27300

Compounds of the formula Ia.35 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

Tables 27301 to 28080

Compounds of the formula Ia.36 in which the combination of $R^{4a}$, $R^{4b}$ and $R^6$ is as defined in tables 1 to 780 and the combination of $R^{5a}$, $R^{5b}$ and $R^{7a}$ for a compound corresponds in each case to one row of Table A.

TABLE A

| No. | $R^{7a}$ | $R^{5a}$ | $R^{5b}$ |
| --- | --- | --- | --- |
| A-1 | H | H | H |
| A-2 | F | H | H |
| A-3 | Cl | H | H |
| A-4 | $CH_3$ | H | H |
| A-5 | $CHF_2$ | H | H |
| A-6 | $CF_3$ | H | H |
| A-7 | $OCH_3$ | H | H |
| A-8 | $OCHF_2$ | H | H |

TABLE A-continued

| No. | $R^{7a}$ | $R^{5a}$ | $R^{5b}$ |
|---|---|---|---|
| A-9 | $OCF_3$ | H | H |
| A-10 | cyclopropyl | H | H |
| A-11 | CN | H | H |
| A-12 | $CH_2OCH_3$ | H | H |
| A-13 | $CH_2CH_2OCH_3$ | H | H |
| A-14 | H | $CH_3$ | H |
| A-15 | F | $CH_3$ | H |
| A-16 | Cl | $CH_3$ | H |
| A-17 | $CH_3$ | $CH_3$ | H |
| A-18 | $CHF_2$ | $CH_3$ | H |
| A-19 | $CF_3$ | $CH_3$ | H |
| A-20 | $OCH_3$ | $CH_3$ | H |
| A-21 | $OCHF_2$ | $CH_3$ | H |
| A-22 | $OCF_3$ | $CH_3$ | H |
| A-23 | cyclopropyl | $CH_3$ | H |
| A-24 | CN | $CH_3$ | H |
| A-25 | $CH_2OCH_3$ | $CH_3$ | H |
| A-26 | $CH_2CH_2OCH_3$ | $CH_3$ | H |
| A-27 | H | $CH_2CH_3$ | H |
| A-28 | F | $CH_2CH_3$ | H |
| A-29 | Cl | $CH_2CH_3$ | H |
| A-30 | $CH_3$ | $CH_2CH_3$ | H |
| A-31 | $CHF_2$ | $CH_2CH_3$ | H |
| A-32 | $CF_3$ | $CH_2CH_3$ | H |
| A-33 | $OCH_3$ | $CH_2CH_3$ | H |
| A-34 | $OCHF_2$ | $CH_2CH_3$ | H |
| A-35 | $OCF_3$ | $CH_2CH_3$ | H |
| A-36 | cyclopropyl | $CH_2CH_3$ | H |
| A-37 | CN | $CH_2CH_3$ | H |
| A-38 | $CH_2OCH_3$ | $CH_2CH_3$ | H |
| A-39 | $CH_2CH_2OCH_3$ | $CH_2CH_3$ | H |
| A-40 | H | $CH_2OCH_3$ | H |
| A-41 | F | $CH_2OCH_3$ | H |
| A-42 | Cl | $CH_2OCH_3$ | H |
| A-43 | $CH_3$ | $CH_2OCH_3$ | H |
| A-44 | $CHF_2$ | $CH_2OCH_3$ | H |
| A-45 | $CF_3$ | $CH_2OCH_3$ | H |
| A-46 | $OCH_3$ | $CH_2OCH_3$ | H |
| A-47 | $OCHF_2$ | $CH_2OCH_3$ | H |
| A-48 | $OCF_3$ | $CH_2OCH_3$ | H |
| A-49 | cyclopropyl | $CH_2OCH_3$ | H |
| A-50 | CN | $CH_2OCH_3$ | H |
| A-51 | $CH_2OCH_3$ | $CH_2OCH_3$ | H |
| A-52 | $CH_2CH_2OCH_3$ | $CH_2OCH_3$ | H |
| A-53 | H | $CH_2OCH_2CH_3$ | H |
| A-54 | F | $CH_2OCH_2CH_3$ | H |
| A-55 | Cl | $CH_2OCH_2CH_3$ | H |
| A-56 | $CH_3$ | $CH_2OCH_2CH_3$ | H |
| A-57 | $CHF_2$ | $CH_2OCH_2CH_3$ | H |
| A-58 | $CF_3$ | $CH_2OCH_2CH_3$ | H |
| A-59 | $OCH_3$ | $CH_2OCH_2CH_3$ | H |
| A-60 | $OCHF_2$ | $CH_2OCH_2CH_3$ | H |
| A-61 | $OCF_3$ | $CH_2OCH_2CH_3$ | H |
| A-62 | cyclopropyl | $CH_2OCH_2CH_3$ | H |
| A-63 | CN | $CH_2OCH_2CH_3$ | H |
| A-64 | $CH_2OCH_3$ | $CH_2OCH_2CH_3$ | H |
| A-65 | $CH_2CH_2OCH_3$ | $CH_2OCH_2CH_3$ | H |
| A-66 | H | $CH_2CH_2OCH_3$ | H |
| A-67 | F | $CH_2CH_2OCH_3$ | H |
| A-68 | Cl | $CH_2CH_2OCH_3$ | H |
| A-69 | $CH_3$ | $CH_2CH_2OCH_3$ | H |
| A-70 | $CHF_2$ | $CH_2CH_2OCH_3$ | H |
| A-71 | $CF_3$ | $CH_2CH_2OCH_3$ | H |
| A-72 | $OCH_3$ | $CH_2CH_2OCH_3$ | H |
| A-73 | $OCHF_2$ | $CH_2CH_2OCH_3$ | H |
| A-74 | $OCF_3$ | $CH_2CH_2OCH_3$ | H |
| A-75 | cyclopropyl | $CH_2CH_2OCH_3$ | H |
| A-76 | CN | $CH_2CH_2OCH_3$ | H |
| A-77 | $CH_2OCH_3$ | $CH_2CH_2OCH_3$ | H |
| A-78 | $CH_2CH_2OCH_3$ | $CH_2CH_2OCH_3$ | H |
| A-79 | H | $CH_2CH_2OCH_2CH_3$ | H |
| A-80 | F | $CH_2CH_2OCH_2CH_3$ | H |
| A-81 | Cl | $CH_2CH_2OCH_2CH_3$ | H |
| A-82 | $CH_3$ | $CH_2CH_2OCH_2CH_3$ | H |
| A-83 | $CHF_2$ | $CH_2CH_2OCH_2CH_3$ | H |
| A-84 | $CF_3$ | $CH_2CH_2OCH_2CH_3$ | H |
| A-85 | $OCH_3$ | $CH_2CH_2OCH_2CH_3$ | H |
| A-86 | $OCHF_2$ | $CH_2CH_2OCH_2CH_3$ | H |
| A-87 | $OCF_3$ | $CH_2CH_2OCH_2CH_3$ | H |
| A-88 | cyclopropyl | $CH_2CH_2OCH_2CH_3$ | H |
| A-89 | CN | $CH_2CH_2OCH_2CH_3$ | H |
| A-90 | $CH_2OCH_3$ | $CH_2CH_2OCH_2CH_3$ | H |
| A-91 | $CH_2CH_2OCH_3$ | $CH_2CH_2OCH_2CH_3$ | H |
| A-92 | H | $CH_3$ | $CH_3$ |
| A-93 | F | $CH_3$ | $CH_3$ |
| A-94 | Cl | $CH_3$ | $CH_3$ |
| A-95 | $CH_3$ | $CH_3$ | $CH_3$ |
| A-96 | $CHF_2$ | $CH_3$ | $CH_3$ |
| A-97 | $CF_3$ | $CH_3$ | $CH_3$ |
| A-98 | $OCH_3$ | $CH_3$ | $CH_3$ |
| A-99 | $OCHF_2$ | $CH_3$ | $CH_3$ |
| A-100 | $OCF_3$ | $CH_3$ | $CH_3$ |
| A-101 | cyclopropyl | $CH_3$ | $CH_3$ |
| A-102 | CN | $CH_3$ | $CH_3$ |
| A-103 | $CH_2OCH_3$ | $CH_3$ | $CH_3$ |
| A-104 | $CH_2CH_2OCH_3$ | $CH_3$ | $CH_3$ |
| A-105 | H | $CH_2CH_3$ | $CH_3$ |
| A-106 | F | $CH_2CH_3$ | $CH_3$ |
| A-107 | Cl | $CH_2CH_3$ | $CH_3$ |
| A-108 | $CH_3$ | $CH_2CH_3$ | $CH_3$ |
| A-109 | $CHF_2$ | $CH_2CH_3$ | $CH_3$ |
| A-110 | $CF_3$ | $CH_2CH_3$ | $CH_3$ |
| A-111 | $OCH_3$ | $CH_2CH_3$ | $CH_3$ |
| A-112 | $OCHF_2$ | $CH_2CH_3$ | $CH_3$ |
| A-113 | $OCF_3$ | $CH_2CH_3$ | $CH_3$ |
| A-114 | cyclopropyl | $CH_2CH_3$ | $CH_3$ |
| A-115 | CN | $CH_2CH_3$ | $CH_3$ |
| A-116 | $CH_2OCH_3$ | $CH_2CH_3$ | $CH_3$ |
| A-117 | $CH_2CH_2OCH_3$ | $CH_2CH_3$ | $CH_3$ |

Among the above compounds, preference is given to compounds Ia.1 and Ia.10; the latter especially if $R^6$ is a heterocyclic ring, for examples as defined in table 22 to 60.

In a specific embodiment, the invention relates to compounds I selected from the compounds of the examples, either in form of free bases or of any pharmaceutically acceptable salt thereof or a steroisomer, the racemate or any mixture of stereoisomers thereof.

The compounds of the present invention can be prepared by using routine techniques familiar to a skilled person. In particular, the compounds of the formula I can be prepared according to the following schemes, wherein the variables, if not stated otherwise, are as defined above.

Compounds of formula I wherein $R^{4b}$ and $R^{5b}$ are H (=compounds I') can be synthesized as described in scheme 1 below. The readily available quinoline 1 in which X is a leaving group, such as Cl, Br I or triflate, is reacted with a suitable boron compound of $R^6$, such as $R^6$-boronic acid ($R^6$—$B(OH)_2$) or the potassium (trifluoro)borate of $R^6$ (e.g. potassium cyclobutyl(trifluoro)borate or potassium cyclopropyl(trifluoro)borate) in a Suzuki coupling reaction to 2. The reaction is carried out in the presence of a Pd catalyst, such as $Pd(OAc)_2$, in general in the presence of a phosphine ligand (e.g. tricyclohexylphosphine; di(adamantan-1-yl)(butyl)-phosphine etc.), or tetrakis(triphenylphosphine)palladium(0) and the like. Quinoline 2 is then N-alkylated with a suitable protective group, such as benzyl, e.g. by reaction with benzyl bromide, to 3. Reduction of the quinolinium compound 3 with a suitable reduction agent, such as sodium borohydride and $H_2$/Raney nickel, yields the 1,2,3,4-tetrahydroquinoline 4, which is then deprotected to 5. Reaction with the 2-halogenoacetamide 6, wherein Y is Cl, Br or I, affords the acetamide 7, the keto group of which is reduced with common reduction agents, like borane, borane-tetrahydrofurane-complex, borane-dimethylsulfide-complex or borohydrides such as sodium borohydride or LAH (lithium aluminium hydride) or DIBAL-H (diisobutyl aluminium hydride), to 8. Cyclization with formaldehyde/aldehyde/ketone 9 (C(O)R$^{3a}$R$^{3b}$=formaldehyde if R$^{3a}$ and R$^{3b}$ are hydrogen; another aldehyde if R$^{3a}$ is hydrogen and R$^{3b}$ is (fluorinated) alkyl, hydroxyalkyl, (fluorinated) alkenyl, (fluorinated) alkynyl, (fluorinated) cycloalkyl, phenyl, phenyl-alkyl or a heterocyclic ring; a ketone if R$^{3a}$ and R$^{3b}$ are (fluorinated) alkyl, hydroxyalkyl, (fluorinated) alkenyl, (fluorinated) alkynyl, (fluorinated) cycloalkyl, phenyl, phenyl-alkyl or a heterocyclic ring), generally in the presence of a strong acid, such as trifluoroacetic acid, yields I'. Alternatively, 2 can be reacted with the 2-halogenoacetamide 6 to 10, which is then reduced to 7.

Scheme 1

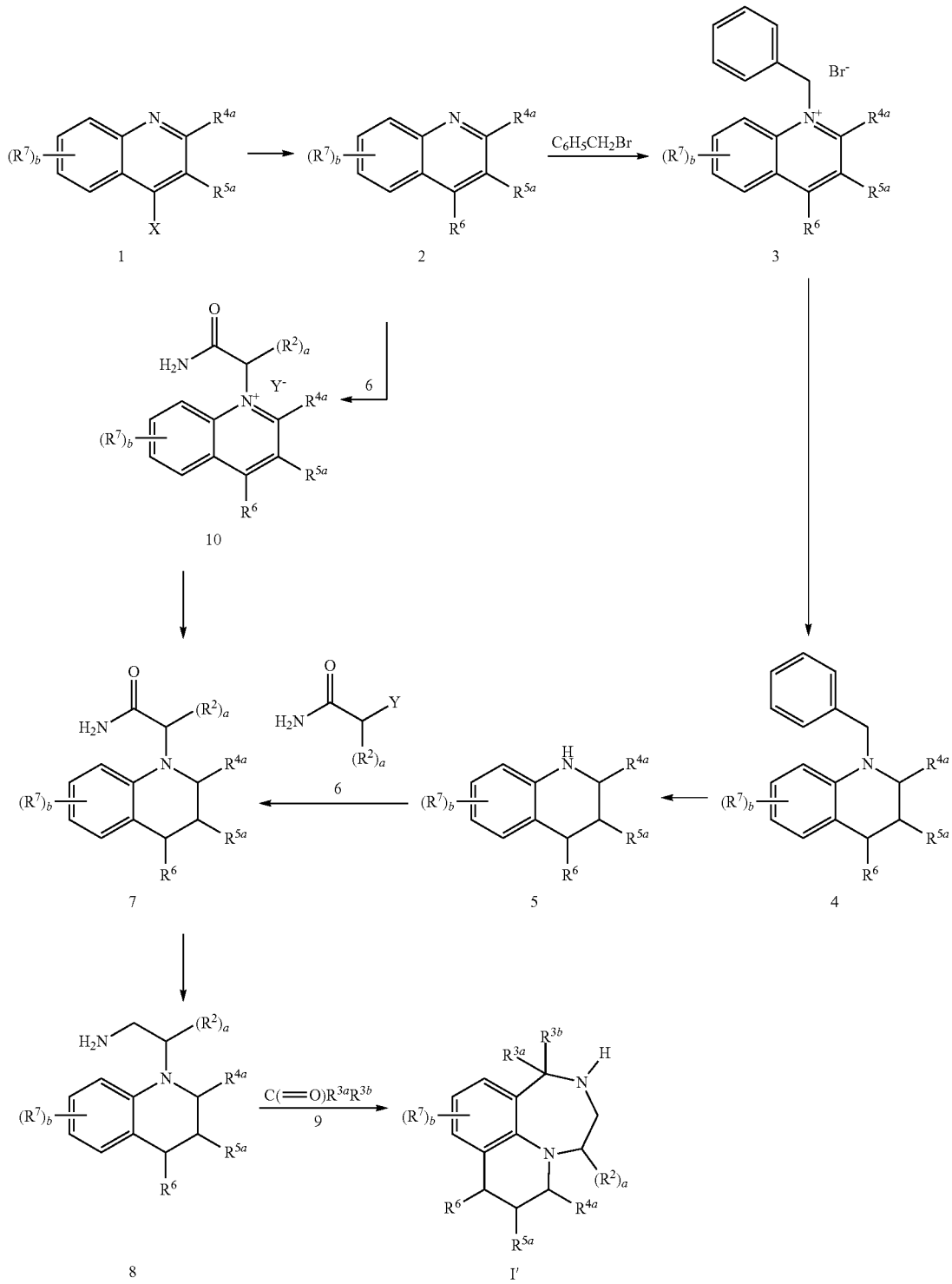

Compounds of formula I wherein $R^{4a}$, $R^{4b}$ and $R^{5b}$ are H (=compounds I") can alternatively be synthesized as described in scheme 2 below. The boronic acid 11 and the α,β-unsaturated ester 12 are reacted in a 1,4-addition in the presence of a Rhodium catalyst, e.g. [RhOH(COD)]$_2$ or Rh(acac)(CO)$_2$, if desired in the presence of a phosphine ligand, such as 1,4-bis(diphenylphosphino)butane (dppb), followed by lactam formation. The lactam 13 is then reduced with common reduction agents, like borane, borane-tetrahydrofurane-complex, borane-dimethylsulfide-complex or borohydrides such as sodium borohydride, to the tetrahydroquinoline 14. Like in the reaction sequence of scheme 1, reaction with the 2-halogenoacetamide 6, wherein Y is Cl, Br or I, affords the acetamide 15, the keto group of which is reduced with common reduction agents, like borane, borane-tetrahydrofurane-complex, borane-dimethylsulfide-complex or borohydrides such as sodium borohydride or LAH (lithium aluminium hydride) or DIBAL-H (diisobutyl aluminium hydride), to 16. Cyclization with formaldehyde/aldehyde/ketone 9, generally in the presence of a strong acid, such as trifluoroacetic acid, yields I".

Scheme 2

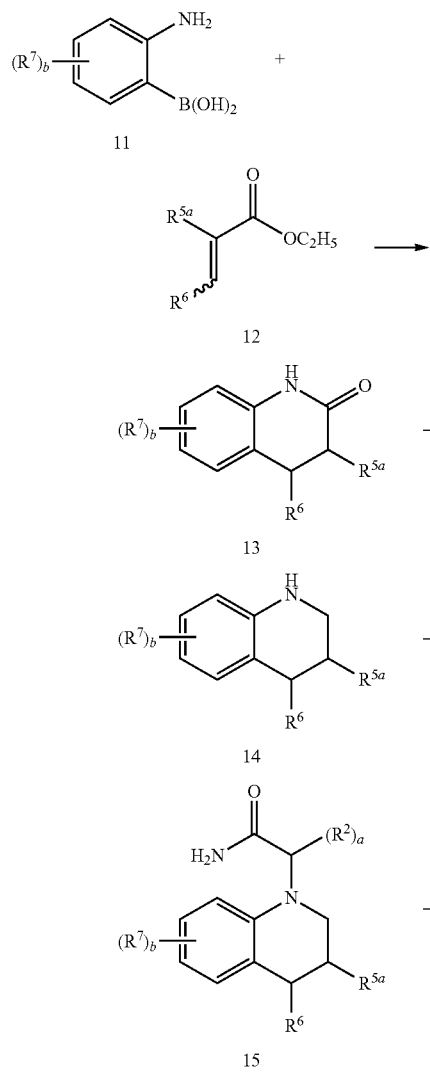

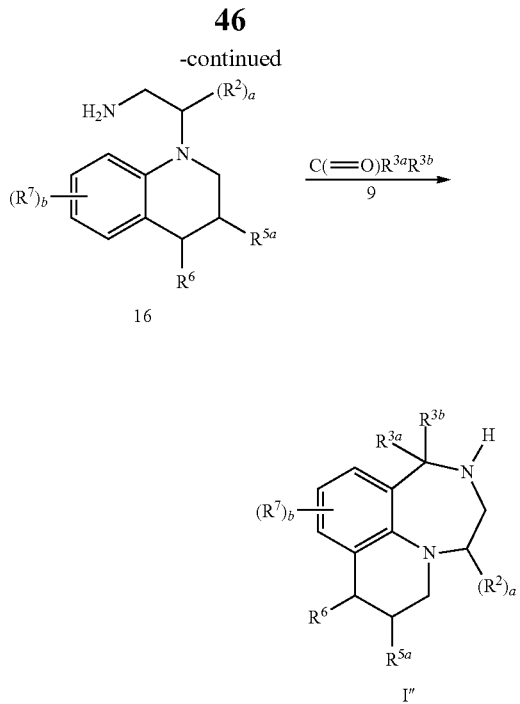

For obtaining compounds I wherein $R^{4a}$ and $R^{4b}$ form together =O, the lactam 13 is not reduced, but is directly reacted with the 2-halogenoacetamide 6 to 17, followed by reduction of the CO group in the amide to 18 and finally cyclisation, as shown in scheme 3 below. Alternatively, compounds I'" can be obtained as described below scheme 4.

Scheme 3

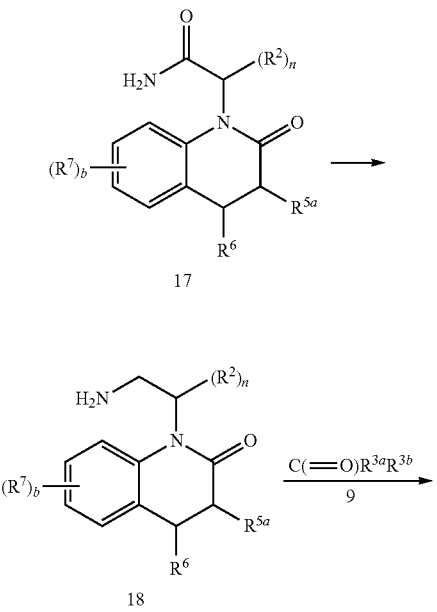

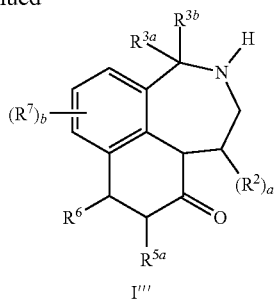

I'''

Compounds of formula I wherein $R^{4a}$, $R^{4b}$ and $R^{5b}$ are H (=compounds I''') can alternatively be synthesized as described in scheme 4 below. The protected tetrahydrobenzodiazepine 19, wherein Z is a hydrogen or a halogen atom, such as Cl, Br or I and PG is a common protective group, such as a carbamate, especially boc, is acylated with the acrylic acid derivative 20, wherein LG is an appropriate leaving group, such as Cl or an anhydride or a chloroformate, in the presence of a base, such as triethylamine or Hünig's base, in an organic solvent, such as ether or methylene chloride. Reaction of 21 with a Lewis acid or a Brönstedt acid HA or irradiation with a suitable wavelength commonly derived from a mercury lamp in an adequate solvent, such as acetone or toluene, in a common photoreactor yields cyclization to 22. Reduction of the carbonyl group with common reduction agents like borohydrides such as sodium borohydride or borane-tetrahydrofurane-complex yields 23, which is deprotected using suitable reagents such as strong bases or acids to I'', wherein $R^{4a}$ and $R^{4b}$ and $R^{5b}$ are H. Compounds I'''' wherein $R^{4a}$ and $R^{4b}$ form together =O can be obtained by skipping the reduction step to 23 and deprotecting 22.

Alternatively, compound 22 can be directly synthesized by reacting the tetrahydrobenzodiazepine 19, wherein Z is —B(OH)$_2$ with the acrylic acid derivative 20 in a 1,4-addition in the presence of a Rhodium catalyst, e.g. [RhOH(COD)]$_2$ or Rh(acac)(CO)$_2$, if desired in the presence of a phosphine ligand, such as 1,4-bis(diphenylphosphino)butane (dppb), followed by lactam formation to 22. This is then further reacted as described above.

Scheme 4

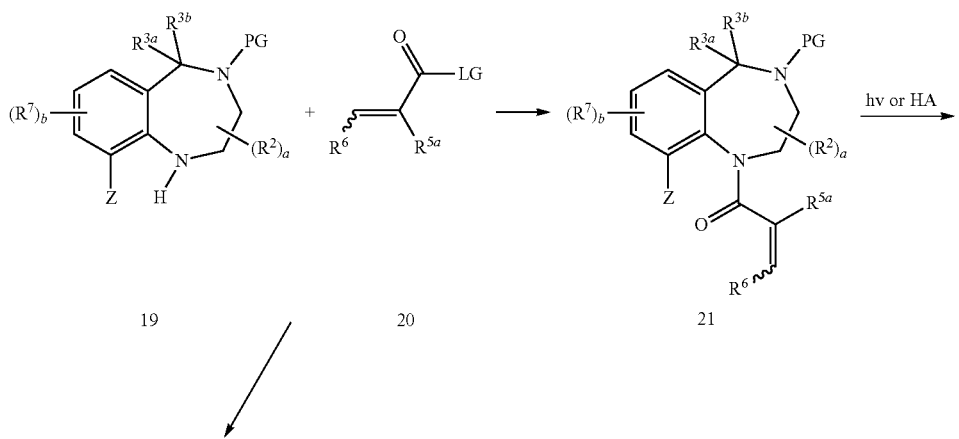

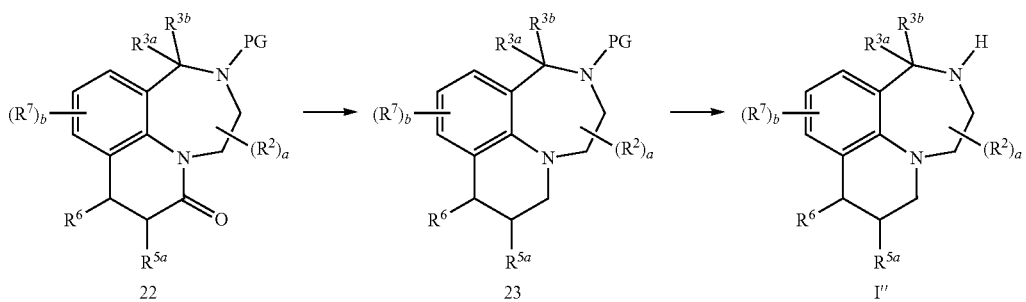

If compound 22 is deprotected, this yields compound I'"
as well as other compounds I in which $(R^2)_a$ is not necessarily bound to the same position as in compounds I'".

If desired, substituents $R^1$ different from hydrogen can be introduced for example via alkylation under typical conditions such as stirring in an appropriate solvent in the presence of an alkylhalide and a base or via other common substitution reactions, or via reductive amination using a suitable aldehyde or ketone in the presence of reduction agent, such as borohydrides, e.g. triacetoxyborohydride, sodium cyanoborohydride or sodium borohydride. —C(=O)$R^9$ as radical $R^1$ can be introduced via amidation under typical amidation conditions, e.g. via reaction with a compound X—C(=O)$R^9$, where X is OH or a halogen atom, under heating and removal of reaction water or using a coupling reagent, such as DCC (dicyclohexylcarbodiimide), DIC (diisopropylcarbodiimide), HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate), HCTU (1H-benzotriazolium-1-[bis(dimethylamino)methylene]-5-chloro tetrafluoroborate), BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) or Py-BrOP (bromotripyrrolidinphosphonium hexafluorophosphate.

Compounds I wherein $R^{5b}$ is different from H can be prepared, for example, by reacting compound 22 with a compound LG-$R^{5b}$ in the presence of a base, wherein LG is an appropriate leaving group, such as Cl or Br.

Alternatively to the method depicted in scheme 4, compounds I wherein $R^{4a}$, $R^{4b}$ and $R^{5b}$ are H (=compounds I") can be synthesized as described in scheme 5 below. Readily available anilines 24 are derivatized with carbonyl moieties 25 by acylation procedures employing appropriate leaving groups LG, such as chlorides or anhydrides, in the presence of a base such as triethylamine or Hünig's base, in an organic solvent, such as diethyl ether or methylene chloride to yield 26. Cyclization products 13 are received by irradiation with a suitable wavelength commonly derived from a mercury lamp in an adequate solvent such as acetone or toluene in a common photoreactor known to those skilled in the art. These are further reacted as depicted in schemes 2 and 3.

Scheme 5

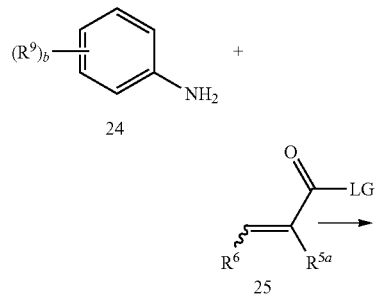

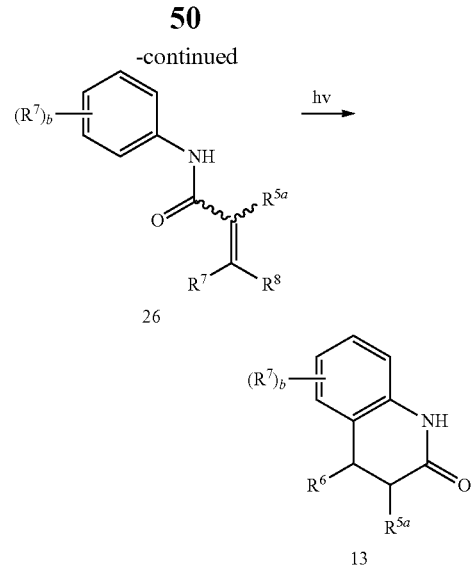

Compounds I wherein $R^{4a}$ and $R^{4b}$ are not H or do not form together a group =O can be prepared by standard derivatization methods of compounds wherein $R^{4a}$ and $R^{4b}$ form together a group =O. For instance, compounds wherein $R^{4a}$ and $R^{4b}$ form together a group =S may be prepared by reaction with a sulfurization agent, such as Lawesson's reagent or $P_2S_5$. Alkyl and related groups as radicals $R^{4a}$ and $R^{4b}$ may be introduced via Grignard reduction Amino and related groups may be introduced via reductive amination. Hydroxyl group $R^{4a}$ or $R^{4b}$ may be introduced by reducing the carbonyl group. This may be alkylated to yield alkoxy and related groups $R^{4a}$ and $R^{4b}$ or substituted by diverse groups.

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis ($3^{rd}$ ed.), John Wiley & Sons, N.Y. (1999), which is herein incorporated by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention further relates to a pharmaceutical composition comprising a therapeutically effective amount of at least one compound I as defined above or an N-oxide, a tautomeric form, a stereoisomer or a pharmaceutically acceptable salt thereof, in combination with at least one pharmaceutically acceptable carrier and/or auxiliary substance.

The present invention further relates to a compound I as defined above or an N-oxide, a tautomeric form, a stereoisomer or a pharmaceutically acceptable salt thereof for use as a medicament.

The present invention also relates to a compound I as defined above or an N-oxide, a tautomeric form, a stereoisomer or a pharmaceutically acceptable salt thereof for the treatment of disorders which respond to the modulation of the 5-HT$_{2C}$ receptor.

The present invention also relates to the use of a compound I as defined above or of an N-oxide, a tautomeric form, a stereoisomer or a pharmaceutically acceptable salt thereof for the manufacture of a medicament for the treatment of disorders which respond to the modulation of the 5-HT$_{2C}$ receptor, and to a method for treating disorders which respond to the modulation of the 5-HT$_{2C}$ receptor, which method comprises administering to a subject in need thereof at least one compound I as defined above or an N-oxide, a tautomeric form, a stereoisomer or a pharmaceutically acceptable salt thereof.

The compounds of the present invention are modulators of the 5-HT$_{2C}$ receptor. Specifically, the compounds of formula I are agonists or partial agonists of the 5-HT$_{2C}$ receptor. Thus, in a specific embodiment, the invention relates to a compound I as defined above or an N-oxide, a tautomeric form, a stereoisomer or a pharmaceutically acceptable salt thereof for the treatment of disorders which respond to 5-HT$_{2C}$ receptor agonists, further to the use of a compound I as defined above or of an N-oxide, a tautomeric form, a stereoisomer or a pharmaceutically acceptable salt thereof for the manufacture of a medicament for the treatment of disorders which respond to 5-HT$_{2C}$ receptor agonists, and to a method for treating disorders which respond to 5-HT$_{2C}$ receptor agonists, which method comprises administering to a subject in need thereof at least one compound I as defined above or an N-oxide, a tautomeric form, a stereoisomer or a pharmaceutically acceptable salt thereof.

Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

In one aspect of the invention, the diseases to be treated are disorders are damage of the central nervous system, disorders of the central nervous system, eating disorders, ocular hypertension, cardiovascular disorders, gastrointestinal disorders and diabetes.

Disorders or diseases of the central nervous system are understood as meaning disorders which affect the spinal cord and, in particular, the brain. These are, for example, cognitive dysfunction, attention deficit disorder/hyperactivity syndrome and cognitive deficits related with schizophrenia, attention deficit/hyperactivity syndrome, personality disorders, affective disorders, motion or motor disorders, pain, migraine, sleep disorders (including disturbances of the Circadian rhythm), feeding disorders, diseases associated with neurodegeneration, addiction diseases, obesity or psoriasis.

Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are obesity, bulimia, weight loss and anorexia, especially anorexia nervosa. Examples of diseases associated with neurodegeneration are stroke, spinal or head trauma, and head injuries, such as hydrocephalus.

Pain condition includes nociceptive pain, neuropathic pain or a combination thereof. Such pain conditions or disorders can include, but are not limited to, post-operative pain, osteoarthritis pain, pain due to inflammation, rheumatoid arthritis pain, musculoskeletal pain, burn pain (including sunburn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer.

In certain other embodiments, the disease condition is bladder dysfunction, including urinary incontinence.

Diabetes includes diabetes insipidus, diabetes mellitus, type I diabetes, type II diabetes, type III diabetes, diabetes secondary to pancreatic diseases, diabetes related to steroid use, diabetes complications, hyperglycemia and insulin resistance.

The addiction diseases include psychiatric disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate, other stimulants including caffeine and nicotine. Addictive substances which come particularly into consideration are opioids, cocaine, amphetamine or amphetamine-like substances, nicotine and alcohol. Especially, addiction disorders include alcohol abuse, cocaine abuse, tobacco abuse and smoking cessation.

With regard to the treatment of addiction diseases, particular preference is given to those compounds according to the invention of the formula (I) which themselves do not possess any psychotropic effect. This can also be observed in a test using rats, which, after having been administered compounds which can be used in accordance with the invention, reduce their self administration of psychotropic substances, for example cocaine.

Examples of gastrointestinal disorders are irritable bowel syndrome.

Preferably, the disorders are selected from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, neuropsychiatric symptoms in Alzheimer's disease (e.g. aggression), behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, psychosis in Parkinson's disease, neuropsychiatric symptoms in Parkinson's disease (e.g. aggression), Lewy Body dementia, neuropsychiatric symptoms in Lewy Body dementia (e.g. aggression), spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance, and are specifically schizophrenia, depression, bipolar disorders, obesity, substance use disorders, neuropsychiatric symptoms in Alzheimer's disease (e.g. aggression) or neuropsychiatric symptoms in Parkinson's disease (e.g. aggression).

The compounds of the invention may be used for a preventive treatment (prophylaxis), in particular as relapse prophylaxis or phase prophylaxis, but are preferably used for a treatment in its proper sense (i.e. non-prophylactic), i.e. for the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

In another embodiment, the present invention relates to the use of a compound I as defined above or an N-oxide, a tautomeric form, a stereoisomer or a pharmaceutically acceptable salt thereof for preparing a medicament for preventing (the development of) a disease condition as described above and to a method for preventing (the development of) a disease condition as described above comprises administering to the subject in need of treatment thereof (e.g., a mammal, such as a human) a therapeutically effective amount of a compound I as defined above or an N-oxide, a tautomeric form, a stereoisomer or a pharmaceutically acceptable salt thereof. As used herein, the term "prevent" a disease condition by administration of any of the compounds described herein means that the detectable physical characteristics or symptoms of the disease or condition do not develop following the administration of the compound described herein. Alternatively, the method comprises administering to the subject a therapeutically effective amount of a compound I as defined above or an N-oxide, a tautomeric form, a stereoisomer or a pharmaceutically acceptable salt thereof, in combination with a therapeutically effective amount of at least one cognitive enhancing drug.

In yet another embodiment, the present invention relates to the use a compound I as defined above or an N-oxide, a tautomeric form, a stereoisomer or a pharmaceutically acceptable salt thereof for preparing a medicament for preventing the progression (e.g., worsening) of a disease condition and to a method for preventing the progression (e.g., worsening) of a disease condition, which method comprises administering to the subject in need of treatment thereof (e.g., a mammal, such as a human) a therapeutically effective amount of a compound I as defined above or an N-oxide, a tautomeric form, a stereoisomer or a pharmaceutically acceptable salt thereof.

There are several lines of evidence suggesting that 5-$HT_{2C}$ agonists or partial agonists would have therapeutic use in a variety of diseases, disorders and conditions.

Knockout mice models lacking the 5-$HT_{2C}$ receptor exhibit hyperphagia, obesity and are more prone to seizures and sudden death [Tecott L H, Sun L M, Akana S F, Strack A M, Lowenstein D H, Dallman M F, Julius D (1995) Eating disorder and epilepsy in mice lacking 5-$HT_{2C}$ serotonin receptors. Nature 374:542-546]. They also exhibit compulsive-like behavior [Chou-Green J M, Holscher T D, Dallman M F, Akana S F (2003). Compulsive behavior in the 5-$HT_{2C}$ receptor knockout mouse. Phys. Behav. 78:641-649], hyperresponsiveness to repeated stress [Chou-Green J M, Holscher T D, Dallman M F, Akana S F (2003). Repeated stress in young and old 5-$HT_{2C}$ receptor knockout mouse. Phys. Behav. 79:217-226], wakefulness [Frank M G, Stryker M P, Tecott L H (2002). Sleep and sleep homeostasis in mice lacking the 5-$HT_{2C}$ receptor. Neuropsychopharmacology 27:869-873], hyperactivity and drug dependence [Rocha B A, Goulding E H, O'Dell L E, Mead A N, Coufal N G, Parsons L H, Tecott L H (2002). Enhanced locomotor, reinforcing and neurochemical effects of cocaine in serotonin 5-hydroxytryptamine 2C receptor mutant mice. J. Neurosci. 22:10039-10045].

5-$HT_{2C}$ is unique among other G-protein-coupled receptors (GPCRs) in that its pre-mRNA is a substrate for base modification via hydrolytic deamination of adenosines to yield inosines. Five adenosines, located within a sequence encoding the putative second intracellular domain can be converted to inosines. This editing can alter the coding potential of the triplet codons and allows for the generation of multiple different receptor isoforms. The edited receptor isoforms were shown to have reduced ability to interact with G-proteins in the absence of agonist stimulation [Werry, T D, Loiacono R, Sexton Pa., Christopoulos A (2008). RNA editing of the serotonin 5-HT$_{2C}$ receptor and its effects on cell signaling, pharmacology and brain function. *Pharmac. Therap.* 119:7-23].

Edited 5-HT$_{2C}$ isoforms with reduced function are significantly expressed in the brains of depressed suicide victims [Schmauss C (2003) Serotonin 2C receptors: suicide, serotonin, and runaway RNA editing. *Neuroscientist* 9:237-242. Iwamoto K, Kato T (2003). RNA editing of serotonin 2C receptor in human postmortem brains of major mental disorders. *Neurosci. Lett.* 346:169-172] and in the learned helplessness rats (a well established animal model of depression) [Iwamotoa K, Nakatanib N, Bundoa M, Yoshikawab T, Katoa T (2005). Altered RNA editing of serotonin 2C receptor in a rat model of depression. *Neurosci. Res.* 53: 69-76] suggesting a link between 5-HT$_{2C}$ function and depression. There are also implications of edited 5-HT$_{2C}$ isoforms and spatial memory [Du Y, Stasko M, Costa A C, Davissone M T, Gardiner K J (2007). Editing of the serotonin 2C receptor pre-mRNA Effects of the Morris Water Maze. *Gene* 391:186-197]. In addition, fully edited isoforms of the human 5-HT$_{2C}$ receptor display a striking reduction in sensitivity to lysergic acid diethylamide (LSD) and to atypical antipsychotic drugs clozapine and loxapine, suggesting a possible role of the receptor in the etiology and pharmacology of schizophrenia [Niswender C M, Herrick-Davis K, Dilley G E, Meltzer H Y, Overholser J C, Stockmeier C A, Emeson R B, Sanders-Bush E (2001). RNA Editing of the Human Serotonin 5-HT$_{2C}$ Receptor: Alterations in Suicide and Implications for Serotonergic *Pharmacotherapy. Neuropsychopharm.* 24:478-491].

Recently, the availability of potent and selective 5-HT$_{2C}$ receptor agonists made it possible to directly investigate the effects of 5-HT$_{2C}$ agonists and their therapeutic potential. Thus recent studies demonstrated that selective 5-HT$_{2C}$ agonists resulted in decreased food intake and body weight gain in normal and obese rats [Smith B M, et al. (2008). Discovery and structure-activity relationship of (1R)-8-chloro-2,3,4,5-tetrahydro-1-methyl-1H-3-benzazepine (Lorcaserin), a selective serotonin 5-HT$_{2C}$ receptor agonist for the treatment of obesity. *J Med Chem* 51:305-313. Thomsen W J, Grottick A J, Menzaghi F, Reyes-Saldana H, Espitia S, Yuskin D, Whelan K, Martin M, Morgan M, Chen W, Al-Shama H, Smith B, Chalmers D, Behan D (2008) Lorcaserin, A Novel Selective Human 5-HT$_{2C}$ Agonist: In Vitro and In Vivo Pharmacological Characterization. *J Pharmacol Exp Ther.* 325:577-587. Rosenzweig-Lipson S, Zhang J, Mazandarani H, Harrison B L, Sabb A, Sabalski J, Stack G, Welmaker G, Barrett J E, Dunlop J (2006) Antiobesity-like effects of the 5-HT$_{2C}$ receptor agonist WAY-161503. *Brain Res.* 1073-1074:240-251. Dunlop J, Sabb A L, Mazandarani H, Zhang J, Kalgaonker S, Shukhina E, Sukoff S, Vogel R L, Stack G, Schechter L, Harrison B L, Rosenzweig-Lipson S (2005). WAY-163909 [97bR, 10aR)-1,2,3,4,8,9,10,10a-octahydro-7bH-cyclopenta-[b][1,4]diazepino[6,7,1hi]indole], a novel 5-hydroxytryptamine 2C receptor—selective agonist with anorectic activity. *J Pharmacol Exp Ther.* 313:862-869.].

Furthermore, selective 5-HT$_{2C}$ receptor agonists produce antidepressant effects in animal models of depression comparable to those of SSRIs but with a much faster onset of action and a therapeutic window that avoids antidepressant-induced sexual dysfunction. These agonists were also effective in animal models of compulsive behavior such as scheduled induced polydipsia and they also exhibited decreased hyperactivity and aggression in rodents [Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis KL (2007) Antidepressant-like effects of the novel, selective, 5-HT$_{2C}$ receptor agonist WAY-163909 in rodents. *Psychopharmacology* (Berlin) 192:159-170. Rosenzweig-Lipson S, Dunlop J, Marquis K L (2007) 5-HT$_{2C}$ receptor agonists as an innovative approach for psychiatric disorders. *Drug news Perspect,* 20: 565-571. Cryan, J F, Lucki I (2000). Antidepressant-like behavioral effects mediated by 5-Hydroxytryptamine 2C receptors. *J. Pharm. Exp. Ther.* 295:1120-1126.].

Acute or chronic administration of 5-HT$_{2C}$ agonists decreases the firing rate of ventral tegmental area dopamine neurons but not that of substantia nigra. In addition 5-HT$_{2C}$ agonists reduce dopamine levels in the nucleus accumbens but not in the striatum (the region of the brain mostly associated with extrapyramidal side effects) [Di Matteo, V., Di Giovanni, G., Di Mascio, M., & Esposito, E. (1999). SB 242084, a selective serotonin 2C receptor antagonist, increases dopaminergic transmission in the mesolimbic system. *Neuropharmacology* 38, 1195-1205. Di Giovanni, G., Di Matteo, V., Di Mascio, M., & Esposito, E. (2000). Preferential modulation of mesolimbic vs. nigrostriatal dopaminergic function by serotonin2C/2B receptor agonists: a combined in vivo electrophysiological and microdialysis study. *Synapse* 35, 53-61. Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1 hi]indole]: A novel 5-hydroxytryptamine 2C receptor-selective agonist with preclinical antipsychotic-like activity. J Pharmacol Exp Ther 320:486-496.]. Therefore it is expected that 5-HT$_{2C}$ receptor agonists will selectively decrease mesolimibic dopamine levels without affecting the nigrostriatal pathway thus avoiding the EPS side effects of typical antipsychotics. Several 5-HT$_{2C}$ receptor agonists have shown antipsychotic activity in animal models of schizophrenia without EPS based on the lack of effect in catalepsy [Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1 hi]indole]: A novel 5-hydroxytryptamine 2C receptor-selective agonist with preclinical antipsychotic-like activity. *J Pharmacol Exp Ther* 320:486-496. Siuciak J A, Chapin D S, McCarthy S A, Guanowsky V, Brown J, Chiang P, Marala R, Patterson T, Seymour Pa., Swick A, Iredale Pa. (2007) CP-809, 101, a selective 5-HT$_{2C}$ agonist, shows activity in animal models of antipsychotic activity. *Neuropharmacology* 52:279-290]. The antipsychotic activity of 5-HT$_{2C}$ receptor agonists without EPS coupled with their beneficial effects in mood disorders and cognition and their antiobesity like effects render 5-HT$_{2C}$ receptor agonists as unique agents to treat schizophrenia [Rosenzweig-Lipson S, Dunlop J, Marquis KL (2007) 5-HT$_{2C}$ receptor agonists as an innovative approach for psychiatric disorders. *Drug news Perspect,* 20: 565-571. Dunlop J, Marquis K L, Lim H K, Leung L, Kao J, Cheesman C, Rosenzweig-Lipson S (2006). Pharmacological profile of the 5-HT$_{2C}$ receptor agonist WAY-163909; therapeutic potential in multiple indications. *CNS Dug Rev.* 12:167-177.].

In addition 5-HT$_{2C}$ modulation has been implicated in epilepsy [Isaac M (2005). Serotonergic 5-HT$_{2C}$ receptors as a potential therapeutic target for the antiepileptic drugs. *Curr. Topics Med. Chem.* 5:59:67], psoriasis [Thorslund K, Nordlind K (2007). Serotonergic drugs-a possible role in the treatment of psoriasis? *Drug News Perspect* 20:521-525], Parkinson's disease and related motor disorders [Esposito E, Di Mateo V, Pierucci M, Benigno A, Di Giavanni, G (2007). Role of central 5-HT$_{2C}$ receptor in the control of basal ganglia functions. *The Basal Ganglia Pathophysiology: Recent Advances* 97-127], behavioral deficits [Barr A M, Lahmann-Masten V, Paulus M, Gainetdinov R P, Caron M G, Geyer M A (2004). The selective serotonin-2A receptor antagonist M100907 reverses behavioral deficits in dopamine transporter knockout mice. *Neuropsychopharmacology* 29:221-228], anxiety [Dekeyne A, Mannoury la Cour C, Gobert A, Brocco M, Lejuene F, Serres F, Sharp T, Daszuta A, Soumier A, Papp M, Rivet J M, Flik G, Cremers T I, Muller O, Lavielle G, Millan M J (2208). 532006, a novel 5-HT$_{2C}$ receptor antagonists displaying broad-based antidepressant and anxiolytic properties in rodent models. *Psychopharmacology* 199:549-568. Nunes-de-Souza V, Nunes-de-Souza R L, Rodgers R J, Canto-de-Souza A (2008). 5-HT2 receptor activation in the midbrain periaqueductal grey (PAG) reduces anxiety-like behavior in mice. *Behav. Brain Res.* 187:72-79.], migraine [Leone M, Rigamonti A, D'Amico D, Grazzi L, Usai S, Bussone G (2001). The serotonergic system in migraine. *Journal of Headache and Pain* 2(*Suppl.* 1):S43-S46], Alzheimer's disease [Arjona A A, Pooler A M, Lee R K, Wurtman R J (2002). Effect of a 5-HT$_{2C}$ serotonin agonist, dexnorfenfluramine, on amyloid precursor protein metabolism in guinea pigs. *Brain Res.* 951:135-140], pain and spinal cord injury [Nakae A, Nakai K, Tanaka T, Hagihira S, Shibata M, Ueda K, Masimo T (2008). The role of RNA editing of the serotonin 2C receptor in a rat model of oro-facial neuropathic pain. *The European Journal of Neuroscience* 27:2373-2379. Nakae A, Nakai K, Tanaka T, Takashina M, Hagihira S, Shibata M, Ueda K, Mashimo T (2008). Serotonin 2C receptor mRNA editing in neuropathic pain model. *Neurosci. Res.* 60:228-231. Kao T, Shumsky J S, Jacob-Vadakot S, Timothy H B, Murray M, Moxon, K A (2006). Role of the 5-HT$_{2C}$ receptor in improving weight-supported stepping in adult rats spinalized as neonates. *Brain* Res. 1112:159-168.], sexual dysfunction [Motofei I G (2008). A dual physiological character for sexual function: the role of serotonergic receptors. *BJU International* 101:531-534. Shimada I, Maeno K, Kondoh Y, Kaku H, Sugasawa K Kimura Y, Hatanaka K; Naitou Y, Wanibuchi F, Sakamoto S; Tsukamoto S (2008). Synthesis and structure-activity relationships of a series of benzazepine derivatives as 5-HT$_{2C}$ receptor agonists. *Bioorg. Med. Chem.* 16:3309-3320], smoking cessation [Fletcher P J, Le A D, Higgins G A (2008). Serotonin receptors as potential targets for modulation of nicotine use and dependence. *Progress Brain Res.* 172:361-83], substance dependence [Bubar M J, Cunningham K A (2008). Prospects for serotonin 5-HT2R pharmacotherapy in psychostimulant abuse. *Progress Brain Res.* 172:319-46], and ocular hypertension [Sharif N A, McLaughlin M A, Kelly C R (2006). AL-34662: a potent, selective, and efficacious ocular hypotensive serotonin-2 receptor agonist. *J Ocul Pharmacol Ther.* 23:1-13].

Further, 5HT modulation can be useful in the treatment of pain, both neuropathic and nociceptive pain, see for example U.S. Patent application publication US2007/0225277. Obata, Hideaki; Ito, Naomi; Sasaki, Masayuki; Saito, Shigeru; Goto, Fumio. Possible involvement of spinal noradrenergic mechanisms in the antiallodynic effect of intrathecally administered 5-HT2C receptor agonists in the rats with peripheral nerve injury. *European Journal of Pharmacology* (2007), 567(1-2), 89-94. Serotonin2C receptor mRNA editing in neuropathic pain model. Nakae, Aya; Nakai, Kunihiro; Tanaka, Tatsuya; Takashina, Masaki; Hagihira, Satoshi; Shibata, Masahiko; Ueda, Koichi; Mashimo, Takashi. Department of Anesthesiology & Intensive Care Medicine, Graduate School of Medicine, Osaka University, *Neuroscience Research* (Amsterdam, Netherlands) (2008), 60(2), 228-231. Antiallodynic effects of intrathecally administered 5-HT2C receptor agonists in rats with nerve injury. Obata, Hideaki; Saito, Shigeru; Sakurazawa, Shinobu; Sasaki, Masayuki; Usui, Tadashi; Goto, Fumio Department of Anesthesiology, Gunma University Graduate School of Medicine, Maebashi, Gunma, Japan. *Pain* (2004), 108(1-2), 163-169. Influence of 5,7-dihydroxytryptamine (5,7-DHT) on the antinociceptive effect of serotonin (5-HT) 5-HT2C receptor agonist in male and female rats. Brus, Ryszard; Kasperska, Alicja; Oswiecimska, Joanna; Szkilnik, Ryszard. Department of Pharmacology, Silesian Medical University, Zabrze, Pol. *Medical Science Monitor* (1997), 3(5), 654-656.

Modulation of 5HT2 receptors may be beneficial in the treatment of conditions related to bladder function, in particular, urinary incontinence. [Discovery of a novel azepine series of potent and selective 5-HT2C agonists as potential treatments for urinary incontinence. Brennan, Paul E.; Whitlock, Gavin A.; Ho, Danny K. H.; Conlon, Kelly; McMurray, Gordon. *Bioorganic & Medicinal Chemistry Letters* (2009), 19(17), 4999-5003. Investigation of the role of 5-HT2 receptor subtypes in the control of the bladder and the urethra in the anesthetized female rat. Mbaki, Y.; Ramage, A. G. Department of Pharmacology, University College London, London, UK. *British Journal of Pharmacology* (2008), 155(3), 343-356.] In particular, compounds with agonist activity at 5-HT$_{2C}$ have been shown to be useful in treating urinary incontinence, see for example U.S. Patent application publications US2008/0146583 and US 2007/0225274.

Further pre-clinical data suggest that 5-HT$_{2C}$ agonists could be useful for the treatment of a number of psychiatric diseases, including schizophrenia, bipolar disorders, depression/anxiety, substance use disorders and especially disorders like neuropsychiatric symptoms in Alzheimer's disease: Aggression, psychosis/agitation represent key unmet medical needs. Clinical (Shen J H Q et al., A 6-week randomized, double-blind, placebo-controlled, comparator referenced trial of vabicaserin in acute schizophrenia. Journal of Psychiatric Research 53 (2014) 14-22; Liu J et al., Prediction of Efficacy of Vabicaserin, a 5-HT$_{2C}$ Agonist, for the Treatment of Schizophrenia Using a Quantitative Systems Pharmacology Model. CPT Pharmacometrics Syst. Pharmacol. (2014) 3, e111;) and preclinical data (Dunlop J et al., Characterization of Vabicaserin (SCA-136), a Selective 5-Hydroxytryptamine 2C Receptor Agonist. J Pharmacol Exp Ther (2011) 337, 673-80; Siuciak J et al., CP-809, 101, a selective 5-HT$_{2C}$ agonist, shows activity in animal models of antipsychotic activity. Neuropharmacology 52 (2007) 279-290; Mosienko V et al., Exaggerated aggression and decreased anxiety in mice deficient in brain serotonin. Transl Psychiatry (2012) 2, e122; Del Guidice T et al., Stimulation of 5-HT$_{2C}$ Receptors Improves Cognitive Deficits Induced by Human Tryptophan Hydroxylase2 Loss of Function Mutation. Neuropsychopharmacology (2014) 39, 1125-

1134; Rosenzweig-Lipson et al., Antidepressant-like effects of the novel, selective, 5-HT$_{2C}$ receptor agonist WAY-163909 in rodents. Psychopharmacology (2007) 192:159-170) suggest 5-HT$_{2C}$ receptor stimulation to result in therapeutic efficacy in aggression, psychosis agitation and moderate pro-cognitive effects (Del Guidice T et al., Stimulation of 5-HT$_{2C}$ Receptors Improves Cognitive Deficits Induced by Human Tryptophan Hydroxylase2 Loss of Function Mutation. Neuropsychopharmacology (2014) 39, 1125-1134; Siuciak J et al., CP-809, 101, a selective 5-HT$_{2C}$ agonist, shows activity in animal models of antipsychotic activity. Neuropharmacology 52 (2007) 279-290).

In the use and the method of the invention, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

In one aspect, the present invention provides pharmaceutical compositions. The pharmaceutical compositions of the present invention comprise the compounds of the present invention or an N-oxide, a tautomeric form, a stereoisomer or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention or an N-oxide, a tautomeric form, a stereoisomer or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M.

Berge et al. describe pharmaceutically acceptable salts in detail in (*J. Pharmaceutical Sciences,* 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The following examples serve to explain the invention without limiting it.

EXAMPLES

The compounds were either characterized via proton-NMR in $d_6$-dimethylsulfoxide, d-chloroform or $d_4$-methanol on a 400 MHz, 500 MHz or 600 MHz NMR instrument (Bruker AVANCE), or by $^{13}$C-NMR at 125 MHz, or by mass spectrometry, generally recorded via HPLC-MS in a fast gradient on C18-material (electrospray-ionisation (ESI) mode).

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.), multiplet (m), doublet of doublets (dd), doublet of doublets of doublets (ddd) etc.

Enantiomers were Separated/Purified by Chiral Supercritical Fluid Chromatography (SFC) (Method A).

Method A:
Analytical Separation Method:
Instrument: Thar analytical SFC
Column: Chiralpak AD-3 3 µm, 0.46 cm id×10 cm L
Mobile phase: A for SFC $CO_2$ and B for EtOH (0.05% IPAm)
Gradient: B in A from 10% to 40% in 5 minutes
Flow rate: 4.0 mL/min
Wavelength: 220 nm
System Back Pressure: 100 bar
Preparative Separation Method:
Instrument: Thar SFC Pre-80
Column: Chiralpak AD-H 5 µm, 3.0 cm id×25 cm L
Mobile phase: A for SFC $CO_2$ and B EtOH (0.05% $NH_4OH$)
Gradient: A:B=78:22
Flow rate: 60 mL/min
Wavelength: 220 nm
System Back Pressure: 100 bar
Sample preparation: dissolved in Methanol, 14 mg/mL
Injection: 1.0 ml per injection.
IPAm: Isopropylamine
Preparative HPLC was Carried Out Under Following Conditions:
Method A:
Instrument: Shimadzu LC-20AP preparative HPLC
Column: Luna(2) C18 250*50 mm i.d. 10 u
Mobile phase: A for $H_2O$ (0.075% TFA) and B for MeCN
Gradient: B from 12% to 42% in 20 min
Flow rate: 80 ml/min
Wavelength: 220 & 254 nm
Injection amount: 0.65 g per injection
Method B:
Instrument: Gilson 281 semi-preparative HPLC system
Mobile phase: A for $H_2O$ (0.075% TFA) and B for MeCN
Column: Luna C18 100*30, 5 um, 100A
Flow rate: 25 ml/min
Monitor wavelength: 220 & 254 nm
Gradient:

| Time | B % |
|------|-----|
| 0.00 | 80 |
| 12.0 | 100 |
| 12.2 | 100 |
| 14.2 | 100 |
| 14.4 | 80 |
| 16.0 | 80 |

Method C
C.1 Analytical SFC

Analytical samples were run on an Agilent 1260 Infinity Hybrid SFC System, controlled by Agilent OpenLab CDS ChemStation Edition. The system consists of an injector, a heated column compartment including a switch for 6 columns, a $CO_2$-booster pump, a binary pump module for $CO_2$ and modifier flow and an UV-detector. The backpressure regulator was set to 160 bars and heated to 60° C. If not stated otherwise, the columns were 100 mm in length, 4.6 mm in diameter and packed with 5 μm material. They were kept at room temperature during analysis. As mobile phase, a mixture of liquefied $CO_2$ and organic modifier with additive was used as indicated for each sample. The flow rate was kept at 3.5 mL/min.

C.2 Preparative SFC

Preparative separations were carried out on a Waters Prep 100q SFC System, controlled by Waters MassLynx Software. The system consists of an open bed injector/collector, a heated column compartment including a switch for 6 columns, a $CO_2$-booster pump, a pump module for modifier flow and an UV-detector. To enable quantitative collection, the gas liquid separator was driven with a make-up flow of 30 mL/min Methanol. The backpressure regulator was set to 120 bar and heated to 60° C. If not stated otherwise, the columns were 250 mm in length, 20 mm in diameter and packed with 5 μm material. They were kept at 30° C. during the separation. As mobile phase, a mixture of liquefied $CO_2$ and organic modifier with additive was used as indicated for each sample. The flow rate was kept at 100 g/min.

LCMS Method:

LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% TFA in water, mobile phase B was 0.018% TFA in MeCN. The column used for the chromatography was a 2.1×50 mm Venusil XBP-C18 column (5 μm particles). Detection methods are diode array (DAD) and evaporative light scattering (ELSD) detection as well as positive/negative electrospray ionization).

Abbreviations:

h hour(s)
min minute(s)
r.t. room temperature (20-25° C.)
PE petroleum ether
EtOH ethanol
MeOH methanol
DCM dichloromethane
DCE dichloroethane
THF tetrahydrofuran
DMF N,N-dimethylformamide
MeCN acetonitrile
EtOAc ethyl acetate
TFA trifluoroacetic acid
DIPEA diisopropylethyl amine
X-Phos 2-dicyclohexylphosphino-2',4',6'-triisopropylbiphenyl I. Preparation Examples Example 1

8-Cyclopropyl-2,3,4,6,7,8-hexahydro-1H-[1,4]diazepino[6,7,1-ij]quinoline (compound Ia.1 wherein $R^6$ is cyclopropyl and $R^{4a}$, $R^{4b}$, $R^{5a}$, $R^{5b}$ and $R^{7a}$ are hydrogen)

1.1 4-Cyclopropylquinoline

A mixture of 4-bromoquinoline (18 g, 87 mmol), cyclopropylboronic acid (29.7 g, 346 mmol), tricyclohexylphosphine (4.85 g, 17.3 mmol), $K_3PO_4$ (73.5 g, 346 mmol) and $PdOAc_2$ (1.942 g, 8.65 mmol) in toluene (200 mL) and water (20 mL) was stirred for 16 h at 100° C. under $N_2$. The resulting mixture was concentrated under reduced pressure and the residue was purified by column chromatography on silica gel (PE:EtOAc=10:1) to give the title compound (10 g, yield 61.2%).

$^1$H NMR (400 MHz; $CDCl_3$): δ 9.00 (d, J=4.4 Hz, 1H), 8.55 (d, J=8.4 Hz, 1H), 8.34 (d, J=8.4 Hz, 1H), 7.93 (t, J=8.0 Hz, 1H), 7.80 (t, J=8.0 Hz, 1H), 7.24 (d, J=4.4 Hz, 1H), 2.68-2.61 (m, 1H), 1.42-1.36 (m, 2H), 1.09-1.05 (m, 2H).

1.2 1-(2-Amino-2-oxoethyl)-4-cyclopropylquinolin-1-ium bromide

A mixture of 4-cyclopropylquinoline from step 1.1 (9 g, 53.2 mmol) and 2-bromoacetamide (14.67 g, 106 mmol) in EtOH (100 mL) was stirred at 90° C. for 16 h. After cooling to 20° C., the mixture was filtered, and the residue was dried in high vacuum to give the title compound (9 g, yield 55.1%).

$^1$H NMR (400 MHz; $d_6$-DMSO): δ 9.24 (d, J=6.0 Hz, 1H), 8.88 (d, J=8.0 Hz, 1H), 8.24-8.13 (m, 3H), 8.03 (t, J=8.0 Hz, 1H), 7.76 (s, 1H), 7.69 (d, J=6.4 Hz, 1H), 5.71 (s, 2H), 3.11-3.05 (m, 1H), 1.55-1.52 (m, 2H), 1.34-1.31 (m, 2H).

1.3 2-(4-Cyclopropyl-2H-quinolin-1-yl)acetamide

To a solution of 1-(2-amino-2-oxoethyl)-4-cyclopropylquinolin-1-ium bromide from step 1.2 (9 g, 29.3 mmol) in MeOH (200 mL), $NaBH_4$ (11.08 g, 293 mmol) was added in portions at 0° C., and then the mixture was stirred at 60° C. for 2 hours. After cooled to 20° C., water (50 mL) was added, and the reaction mixture was extracted with DCM (50 mL×2), and the organic phase was dried with $Na_2SO_4$, concentrated under reduced pressure to give crude title compound (5 g, 74.8% yield), which was used directly in the next step.

LCMS (ESI$^+$): m/z 228.9 (M+H)$^+$, RT: 1.03 min.

1.4 2-(4-Cyclopropyl-3,4-dihydroquinolin-1(2H)-yl)acetamide

To a solution of 2-(4-cyclopropyl-2H-quinolin-1-yl)acetamide from step 1.3 (5 g, 21.9 mmol) in MeOH (100 mL), Raney Ni (1.286 g, 21.9 mmol) was added under Ar, and the reaction mixture was stirred for 12 h at 20° C. under $H_2$ (15 psi of pressure). Then the mixture was filtered, the filtrate was concentrated under reduced pressure and the residue was purified by preparative HPLC (method A) to give the title compound (1.8 g, yield 35.7%)

$^1$H NMR (400 MHz; $CDCl_3$): δ 7.18 (d, J=7.2 Hz, 1H), 6.93 (t, J=7.2 Hz, 1H), 6.57 (t, J=7.6 Hz, 1H), 6.45 (s, 1H), 6.25 (d, J=8.4 Hz, 1H), 6.25 (s, 1H), 3.65 (s, 2H), 3.30-3.27 (m, 1H), 3.16-3.14 (m, 1H), 1.96-1.81 (m, 3H), 0.73-0.70 (m, 1H), 0.53-0.52 (m, 1H), 0.33-0.32 (m, 1H), 0.27-0.23 (m, 1H), 0.05-0.02 (m, 1H)

1.5 2-(4-Cyclopropyl-3,4-dihydroquinolin-1(2H)-yl)ethanamine

To a solution of 2-(4-cyclopropyl-3,4-dihydroquinolin-1 (2H)-yl)acetamide from step 1.4 (1.8 g, 7.82 mmol) in THF (50 mL), a solution of $BH_3$.THF (15.6 mL, 15.63 mmol) was added at 0° C., and the reaction solution was stirred for 12 h at 70° C. After cooling to 20° C., MeOH (20 mL) was added dropwise at 0° C. The reaction solution was stirred for 30 minutes at 20° C. and then concentrated under reduced pressure to give a residue, which was purified by preparative HPLC (method A) to give the title compound (900 mg, yield 53.2%)

$^1$H NMR (400 MHz; $CDCl_3$): δ 7.81 (s, 1H), 7.19 (d, J=7.6 Hz, 1H), 6.93 (t, J=7.6 Hz, 1H), 6.57-6.49 (m, 2H), 3.41-3.38 (m, 3H), 3.33-3.19 (m, 1H), 3.08-3.07 (m, 1H), 2.99-2.96 (m, 2H), 1.89-1.86 (m, 1H), 1.80-1.73 (m, 2H), 0.71-0.68 (m, 1H), 0.53-0.52 (m, 1H), 0.35-0.32 (m, 1H), 0.25-0.22 (m, 1H), 0.05-0.02 (m, 1H)

1.6 8-Cyclopropyl-2,3,4,6,7,8-hexahydro-1H-[1,4]diazepino[6,7,1-ij]quinoline

To a solution of 2-(4-cyclopropyl-3,4-dihydroquinolin-1 (2H)-yl)ethanamine from step 1.5 (900 mg, 4.16 mmol) and 37% formaldehyde solution (0.93 mL, 12.48 mmol) in EtOH (15 mL), TFA (0.962 mL, 12.48 mmol) was added at 0° C., and the reaction mixture was stirred for 2 h at 80° C. Then the reaction solution was concentrated under reduced pressure and the residue was purified by preparative HPLC (method A) to give the title compound (500 mg, yield 52.6%).

LCMS (ESI$^+$): m/z 229.1 (M+H)$^+$, RT: 0.979 min.

1.7 Racemic resolution of 8-cyclopropyl-2,3,4,6,7,8-hexahydro-1H-[1,4]diazepino[6,7,1-ij]quinoline to (S)-8-cyclopropyl-2,3,4,6,7,8-hexahydro-1H-[1,4]diazepino[6,7,1-ij]quinoline and (R)-8-cyclopropyl-2,3,4,6,7,8-hexahydro-1H-[1,4]diazepino[6,7,1-ij]quinoline 8-Cyclopropyl-2,3,4,6,7,8-hexahydro-1H-[1,4]diazepino[6,7,1-ij]quinoline (500 mg, 2.19 mmol) was separated by chiral SFC (method A) to give enantiomer 1.A (107.7 mg, yield 21.5%), and enantiomer 1.B (125.6 mg, yield 25.1%).

Enantiomer 1.A was collected from 7.0 min to 9.6 min; and enantiomer 1.B was collected from 10.2 min to 12.8 min.

$^1$H NMR of enantiomer 1.A (400 MHz; CD$_3$OD): δ 7.33 (d, J=7.6 Hz, 1H), 7.01 (d, J=7.6 Hz, 1H), 6.78 (t, J=7.6 Hz, 1H), 3.85 (s, 2H), 3.43-3.41 (m, 1H), 3.29-3.26 (m, 1H), 3.14-3.12 (m, 2H), 3.06-3.04 (m, 2H), 2.06-1.96 (m, 2H), 1.86-1.84 (m, 1H), 0.87-0.85 (m, 1H), 0.71-0.69 (m, 1H), 0.51-0.46 (m, 2H), 0.25-0.24 (m, 1H)

LCMS (ESI$^+$) of enantiomer A: m/z 229.1 (M+H)$^+$, RT: 2.455 min.

$^1$H NMR of enantiomer 1.B (400 MHz; CD$_3$OD): δ 7.45 (d, J=7.6 Hz, 1H), 7.12 (d, J=7.2 Hz, 1H), 6.87 (t, J=7.6 Hz, 1H), 4.16 (s, 2H), 3.48-3.43 (m, 1H), 3.32-3.30 (m, 5H), 2.07-1.98 (m, 2H), 1.87-1.86 (m, 1H), 0.87-0.85 (m, 1H), 0.71-0.69 (m, 1H), 0.51-0.46 (m, 2H), 0.26-0.25 (m, 1H)

LCMS (ESI$^+$) of enantiomer B: m/z 229.1 (M+H)$^+$, RT: 2.460 min.

Example 2

8-Cyclobutyl-2,3,4,6,7,8-hexahydro-1H-[1,4]diazepino[6,7,1-ij]quinoline (compound Ia.1 wherein R$^6$ is cyclobutyl and R$^{4a}$, R$^{4b}$, R$^{5a}$, R$^{5b}$ and R$^{7a}$ are hydrogen)

2.1 4-Cyclobutylquinoline

A mixture of 4-bromoquinoline (600 mg, 2.88 mmol), di(adamantan-1-yl)(butyl)-phosphine (70 mg, 0.195 mmol), Pd(OAc)$_2$ (26 mg, 0.116 mmol), potassium cyclobutyltrifluoroborate (600 mg, 3.70 mmol) and Cs$_2$CO$_3$ (2819 mg, 8.65 mmol) in toluene (11 mL) and water (1.1 mL) was heated at 100° C. for 72 h under N$_2$. After cooling to 25° C., water (20 mL) was added, and the mixture was extracted with EtOAc (30 mL×2). The organic phase was dried over Na$_2$SO$_4$, filtered and concentrated under reduced pressure to give a residue, which was purified by preparative HPLC (method A) to give the title compound (300 mg, 56.8% yield) as yellow oil.

$^1$H NMR (400 MHz; CDCl$_3$): δ 8.85 (s, 1H), 8.10 (d, J=8.4 Hz, 1H), 7.93-7.91 (m, 1H), 7.68 (t, J=8.0 Hz, 1H), 7.54-7.50 (m, 1H), 7.26 (d, J=4.9 Hz, 1H), 4.19-4.10 (m, 1H), 2.59-2.51 (m, 2H), 2.36-2.26 (m, 2H), 2.24-2.13 (m, 1H), 1.97-1.90 (m, 1H)

2.2 1-Benzyl-4-cyclobutyl-quinolin-1-ium bromide

A mixture of 4-cyclobutylquinoline from step 2.1 (100 mg, 0.546 mmol) and (bromomethyl)benzene (747 mg, 4.37 mmol) in toluene (15 mL) was stirred for 12 h at 80° C. After cooling, the resulting mixture was filtered and the residue was dried by high vacuum to give the title compound (50 mg, yield 13%), which was used in the next step without further purification.

2.3 1-Benzyl-4-cyclobutyl-1,2,3,4-tetrahydroquinoline

To a solution of 1-benzyl-4-cyclobutyl-quinolin-1-ium bromide from step 2.2 (200 mg, 0.565 mmol) in MeOH (20 mL) was added NaBH$_4$ (320 mg, 8.47 mmol) in portions at 25° C. and the reaction mixture was stirred for 3 h at 25° C. Then Raney nickel (128 mg, 2.179 mmol) was added at 25° C. under Ar, and the reaction solution was stirred for 2 h at 15 psi pressure of H$_2$. The reaction mixture was filtered, the filtrate was concentrated under reduced pressure and the residue was purified by preparative HPLC (method B) to give the title compound (100 mg, yield 49.6%).

$^1$H NMR (400 MHz; CDCl$_3$): δ 7.26-7.14 (m, 5H), 6.93-6.89 (m, 2H), 6.5-6.43 (m, 2H), 4.42 (t, J=4.9 Hz, 2H), 3.34-3.27 (m, 1H), 3.20-3.14 (m, 1H), 2.63-2.58 (m, 1H), 2.47-2.37 (m, 1H), 2.01-1.83 (m, 4H), 1.78-1.65 (m, 4H).

2.4 4-Cyclobutyl-1,2,3,4-tetrahydroquinoline

To a solution of 1-benzyl-4-cyclobutyl-1,2,3,4-tetrahydroquinoline from step 2.3 (195 mg, 0.703 mmol) in DCE (20 mL), 1-chloroethyl carbonochloridate (502 mg, 3.51 mmol) was added and the solution was heated to 80° C. for 12 h under N$_2$. After cooling to 20° C., MeOH (5 mL) was added and the resulting solution was heated to 80° C. for 3 h. The mixture was concentrated under reduced pressure and the residue was purified by preparative HPLC (method A, however gradient: B from 5% to 35% in 20 min and 0.25 g per injection) to give the title compound (126 mg, yield 96%).

$^1$H NMR (400 MHz; CDCl$_3$): δ 6.92-6.88 (m, 2H), 6.52-6.48 (m, 1H), 6.30 (d, J=8.0 Hz, 1H), 3.23-3.15 (m, 2H), 2.57-2.55 (m, 1H), 2.45-2.35 (m, 1H), 2.0-1.9 (m, 3H), 1.73-1.66 (m, 6H).

2.5 2-(4-Cyclobutyl-3,4-dihydroquinolin-1(2H)-yl)acetamide

To a solution of 4-cyclobutyl-1,2,3,4-tetrahydroquinoline from step 2.4 (100 mg, 0.534 mmol) in DMF (20 mL), 2-iodoacetamide (593 mg, 3.2 mmol) was added and the solution was heated to 120° C. for 12 h under N$_2$. Water (20 mL) was added; the mixture was extracted with EtOAc (50 mL×2), and the organic phase was washed with HCl (20 mL, 1N) and brine, dried and concentrated under reduced pressure to give the title compound (100 mg, yield 77%).

$^1$H NMR (400 MHz; CDCl$_3$): δ 7.04-6.96 (m, 2H), 6.64-6.60 (m, 1H), 6.438 (d, J=8.0 Hz, 1H), 6.35 (s, 1H), 5.35 (s, 1H), 3.82-3.69 (m, 2H), 3.29-3.25 (m, 1H), 3.17-3.14 (m, 1H), 2.62-2.59 (m, 1H), 2.39-2.35 (m, 1H), 1.98-1.85 (m, 4H), 1.75-1.69 (m, 4H).

2.6 2-(4-Cyclobutyl-3,4-dihydroquinolin-1(2H)-yl)ethanamine

To a solution of 2-(4-cyclobutyl-3,4-dihydroquinolin-1 (2H)-yl)acetamide from step 2.5 (150 mg, 0.614 mmol) in THF (20 mL), BH$_3$THF (5 mL, 5 mmol) was added, and the solution was heated to 80° C. for 12 h under N$_2$. After cooling to 25° C., MeOH (15 mL) was added dropwise, and the reaction solution mixture was stirred 30 minutes at 25° C. Then the resulting solution was concentrated under reduced pressure and the residue was purified by preparative HPLC to give the title compound (100 mg, yield 77%) (method B, however with following gradient:

| Time | B % |
|------|-----|
| 0.00 | 15 |
| 12.0 | 55 |
| 12.1 | 55 |
| 12.2 | 100 |
| 13.5 | 100 |
| 13.6 | 15 |
| 15.0 | 15) |

$^1$H NMR (400 MHz; CD$_3$OD): δ 7.04-6.96 (m, 2H), 6.54 (d, J=8.0, 1H), 6.58-6.54 (m, 1H), 3.59-3.51 (m, 2H), 3.21-3.11 (m, 3H), 3.82-3.69 (m, 2H), 3.29-3.25 (m, 1H), 3.17-3.14 (m, 1H), 2.62-2.59 (m, 1H), 2.65-2.55 (m, 1H), 2.5-2.4 (m, 1H), 2.06-1.76 (m, 9H).

2.7 8-Cyclobutyl-2,3,4,6,7,8-hexahydro-1H-[1,4]diazepino[6,7,1-ij]quinoline

To a solution of 2-(4-cyclobutyl-3,4-dihydroquinolin-1(2H)-yl)ethanamine from step 2.6 (150 mg, 0.651 mmol) in EtOH (20 mL), formaldehyde (0.448 mL, 6.51 mmol) and TFA (0.502 mL, 6.51 mmol) were added and the reaction mixture was heated at 80° C. for 2 h under N$_2$. The resulting solution was concentrated under reduced pressure and the residue was purified by preparative HPLC to give the title compound (50 mg, yield 31.3%) (method B, however with following gradient:

| Time | B % |
|------|-----|
| 0.00 | 10 |
| 12.0 | 50 |
| 12.1 | 50 |
| 12.2 | 100 |
| 13.5 | 100 |
| 13.6 | 10 |
| 15.0 | 10). |

Example 3

8-(3-Methyloxetan-3-yl)-2,3,4,6,7,8-hexahydro-1H-[1,4]diazepino[6,7,1-ij]quinoline (compound Ia.1 wherein R$^6$ is 3-methyloxetan-3-yl and R$^{4a}$, R$^{4b}$, R$^{5a}$, R$^{5b}$ and R$^{7a}$ are hydrogen)

3.1 4-(3-Methyloxetan-3-yl)-3,4-dihydroquinolin-2(1H)-one

In a 5 mL microwave vial containing 3-(3-methyloxetan-3-yl)-acrylic acid ethyl ester (500 mg, 0.588 mmol, 1.00 eq), 2-aminophenyl boronic ester (805 mg, 1.18 mmol, 2.00 eq), potassium carbonate (812 mg, 1.18 mmol, 2.00 eq) and [RhOH(COD)]$_2$ (67 mg, 0.029 mmol, 0.05 eq) was added 2% wt. TPGS-750-M solution in water (3 mL) (TPGS-750-M: a surfactant composed of a lipophilic α-tocopherol moiety and a hydrophilic PEG-750-M chain, joined by a succinic acid linker; forms spontaneously micelles upon dissolution in water. From Sigma-Aldrich). The mixture was stirred vigorously at ambient temperature for 24 h. Then the reaction mixture was extracted with ethyl acetate. The organic phase was dried over MgSO$_4$, filtrated and reduced under vacuum. The crude product was purified by column chromatography on silica (eluent: 0-10% methanol in dichloromethane) to yield the title compound (680 mg, 96% yield).

$^1$H NMR (500 MHz, CDCl$_3$) δ 9.15 (s, 1H), 7.22 (ddd, J=8.0, 6.5, 2.3 Hz, 1H), 7.06-6.97 (m, 2H), 6.89-6.83 (m, 1H), 4.83 (d, J=5.9 Hz, 1H), 4.63 (d, J=5.8 Hz, 1H), 4.41 (d, J=5.7 Hz, 1H), 4.29 (d, J=6.0 Hz, 1H), 3.57 (dd, J=7.3, 4.7 Hz, 1H), 2.70 (dd, J=16.6, 7.3 Hz, 1H), 2.40 (dd, J=16.7, 4.7 Hz, 1H), 1.32 (s, 3H) ppm.

$^{13}$C NMR (125 MHz, CDCl$_3$) δ 171.45, 137.42, 128.34, 128.06, 123.40, 122.79, 116.16, 82.07, 81.95, 43.56, 42.78, 31.98, 19.10 ppm.

ESI-MS: m/z (%): 218.20 (100, [M+H]$^+$).

3.2 4-(3-Methyloxetan-3-yl)-1,2,3,4-tetrahydroquinoline 640 mg of 4-(3-methyloxetan-3-yl)-3,4-dihydroquinolin-2(1H)-one from step 3.1 (2.95 mmol, 1.00 eq) was dissolved in 2 mL of THF (anhydrous) and 5.89 mL of borane tetrahydrofurane complex (5.89 mmol, 1 M in THF, 2.00 eq) was slowly added. The mixture was heated in a microwave at 60° C. for 20 min. Then the reaction mixture was quenched with HCl (1 M) and the aqueous phase was extracted with ethyl acetate. Subsequently the organic phase was extracted three times with HCl (1M) and NaOH (1M) was added to the aqueous phase until pH 10. This was then extracted with dichloromethane three times. The organic phase was dried over MgSO$_4$ and reduced under vacuum. The crude product was purified by column chromatography on silica (eluent: 0-10% methanol in dichloromethane) to yield the title compound (345 mg, 52% yield).

ESI-MS: m/z (%): 204.10 (100, [M+H]$^+$).

3.3 2-(4-(3-Methyloxetan-3-yl)-3,4-dihydroquinolin-1(2H)-yl)acetamide

A mixture of 170 mg of 4-(3-methyloxetan-3-yl)-1,2,3,4-tetrahydroquinoline from step 3.2 (0.836 mmol, 1.00 eq), 2-iodoacetamide (309 mg, 1.67 mmol, 2.00 eq) and DIPEA (0.57 ml, 3.35 mmol, 4.00 eq) in DMF (3 mL) was heated in a microwave at 130° C. for 2 h. Then NaOH (1M) was added and the mixture was extracted with dichloromethane. The organic phase was dried over MgSO$_4$ and reduced under vacuum. The crude product was purified by column chromatography on silica (eluent: 0-10% methanol in dichloromethane) to yield the title compound (136 mg, 56% yield).

ESI-MS: m/z (%): 261.20 (100, [M+H]$^+$).

3.4 2-(4-(3-Methyloxetan-3-yl)-3,4-dihydroquinolin-1(2H)-yl)ethanamine

To a solution of 50 mg of 2-(4-(3-methyloxetan-3-yl)-3,4-dihydroquinolin-1(2H)-yl)acetamide from step 3.3 (0.192 mmol, 1.00 eq) in THF (2 ml) 0.768 mL of lithium aluminium hydride (1 M in THF, 0.768 mmol, 4.00 eq) was slowly added at 0° C. The mixture was stirred at 0° C. for 10 min and was then warmed up to r.t. and stirred for further 6 h at r.t. Then water (0.02 mL) was added followed by 10% aqueous NaOH (0.02 mL) and water (0.069 mL) again. Subsequently MgSO$_4$ was added, the mixture was filtrated and the solvent was evaporated. The crude product was purified by column chromatography on silica (eluent: 0-10% methanol in dichloromethane) to yield the title compound (30 mg, 63% yield).

ESI-MS: m/z (%): 247.20 (100, [M+H]$^+$).

3.5 8-(3-Methyloxetan-3-yl)-2,3,4,6,7,8-hexahydro-1H-[1,4]diazepino[6,7,1-ij]quinoline A mixture of 30 mg of 2-(4-(3-methyloxetan-3-yl)-3,4-dihydroquinolin-1(2H)-yl)ethanamine from step 3.4 (0.122 mmol, 1.00 eq), formaldehyde (9.5 μL, 0.128 mmol, 1.10 eq) and TFA (10.3 μL, 0.128 mmol, 1.10 eq) in ethanol (1 mL) was stirred at ambient temperature for 2 h. Then NaOH (1M) was added and the mixture was extracted with dichloromethane. The organic phase was dried over MgSO$_4$ and reduced under vacuum. The crude product was purified by column chromatography on silica (eluent: 0-10% methanol in dichloromethane) to yield the title compound (16 mg, 51% yield).

$^1$H NMR (600 MHz, CDCl$_3$) δ 6.98 (d, 1H), 6.74 (t, J=7.5 Hz, 1H), 6.44 (d, J=7.8, 1.3 Hz, 1H), 4.97 (d, J=5.4 Hz, 1H), 4.77 (d, J=5.5 Hz, 1H), 4.50 (dd, J=5.4, 0.8 Hz, 1H), 4.31 (dd, J=5.5, 0.8 Hz, 1H), 3.96 (d, J=14.3 Hz, 1H), 3.84 (d, J=14.3 Hz, 1H), 3.38 (dd, J=10.6, 5.5 Hz, 1H), 3.26-3.22 (m, 2H), 3.13-3.03 (m, 3H), 1.70-1.62 (m, 1H), 1.62-1.52 (m, 1H), 1.28 (s, 3H).

ESI-MS: m/z (%): 259.20 (100, [M+H]$^+$).

Example 4

8-(2,2-Difluorocyclopropyl)-2,3,4,6,7,8-hexahydro-1H-[1,4]diazepino[6,7,1-ij]quinoline (compound Ia.1 wherein R$^6$ is 2,2-difluorocyclopropyl and R$^{4a}$, R$^{4b}$, R$^{5a}$, R$^{5b}$ and R$^{7a}$ are hydrogen)

4.1 4-(2,2-Difluorocyclopropyl)-3,4-dihydroquinolin-2(1H)-one

A mixture of 1.26 g of (2,2-difluorocyclopropyl)-acrylic acid ethyl ester (7.16 mmol, 1.00 eq), 1.86 g of 2-aminophenyl boronic ester (13.6 mmol, 1.90 eq), 1.60 g of potassium tert-butoxide (14.3 mmol, 2.00 eq) and 163 mg of [RhOH(COD)]$_2$ (0.358 mmol, 0.05 eq) in dioxane (10 mL) was heated in the microwave at 145° C. for 1 h. Then water and 1M HCl were added and the reaction mixture was extracted with ethyl acetate. The organic phase was dried over MgSO$_4$, filtrated and reduced under vacuum. The crude product was purified by column chromatography on silica (eluent: 0-10% methanol in dichloromethane) to yield the title product (44%, 3.17 mmol).

ESI-MS: m/z (%): 224.10 (100, [M+H]$^+$).

4.2 4-(2,2-Difluorocyclopropyl)-1,2,3,4-tetrahydroquinoline 885 mg of 4-(2,2-difluorocyclopropyl)-3,4-dihydroquinolin-2(1H)-one (3.96 mmol, 1.00 eq) from step 4.1 was dissolved in 10 mL of THF (dry) and 5.95 mL of borane tetrahydrofurane complex (1 M in THF, 3.00 eq) were slowly added. The mixture was heated in a microwave at 90° C. for 2 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over MgSO$_4$ and reduced under vacuum. The crude product was purified by column chromatography on silica (eluent: 0-10% methanol in dichloromethane) to yield the desired product (19%, 0.765 mmol).

ESI-MS: m/z (%): 210.15 (100, [M+H]$^+$).

4.3 2-(4-(2,2-Difluorocyclopropyl)-3,4-dihydroquinolin-1(2H)-yl)acetamide

A mixture of 180 mg of 4-(2,2-difluorocyclopropyl)-1,2,3,4-tetrahydroquinoline (0.860 mmol, 1.00 eq) from step 4.2, 318 mg 2-iodoacetamide (1.72 mmol, 2.00 eq) and 0.585 mL of DIPEA (3.35 mmol, 4.00 eq) in DMF (2 mL) was heated in a microwave at 100° C. for 8 h. Then NaOH (1M) was added and the mixture was extracted with dichloromethane. The organic phase was dried over MgSO$_4$ and reduced under vacuum. The crude product was purified by column chromatography on silica (eluent: 0-10% methanol in dichloromethane) to yield the title product (93%, 0.803 mmol).

ESI-MS: m/z (%): 267.15 (100, [M+H]$^+$).

4.4 2-(4-(2,2-Difluorocyclopropyl)-3,4-dihydroquinolin-1(2H)-yl)ethanamine

To a solution of 225 mg of 2-(4-(2,2-difluorocyclopropyl)-3,4-dihydroquinolin-1(2H)-yl)acetamide (0.845 mmol, 1.00 eq) from step 4.3 in THF (10 ml) was added 1.27 mL of borane tetrahydrofurane complex (2 M in THF, 2.53 mmol, 3.00 eq). The mixture was heated in a microwave at 90° C. for 2 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over MgSO$_4$ and reduced under vacuum. The crude product was purified by column chromatography on silica (eluent: 0-30% methanol in dichloromethane) to yield the title product (64%, 0.543 mmol).

ESI-MS: m/z (%): 253.15 (100, [M+H]$^+$).

4.5 8-(2,2-Difluorocyclopropyl)-2,3,4,6,7,8-hexahydro-1H-[1,4]diazepino[6,7,1-ij]quinoline A mixture of 137 mg of 2-(4-(2,2-difluorocyclopropyl)-3,4-dihydroquinolin-1(2H)-yl)ethanamine (0.543 mmol, 1.00 eq) from step 4.4, formaldehyde (0.570 mmol, 1.05 eq) and TFA (0.597 mmol, 1.10 eq) in ethanol (5 mL) was stirred at ambient temperature for 24 h. Then NaOH (1M) was added and the mixture was extracted with dichloromethane. The organic phase was dried over MgSO$_4$ and reduced under vacuum. The crude product was purified by column chromatography on silica (eluent: 0-10% methanol in dichloromethane) to yield the title product (64%, 0.346 mmol).

ESI-MS: m/z (%): 265.20 (100, [M+H]$^+$).

$^1$H NMR (500 MHz, CDCl$_3$) of mixture of diastereomers: δ 7.21-7.13 (m, 2H), 7.04-6.98 (m, 2H), 6.85 (t, J=7.5 Hz, 1H), 6.77 (t, J=7.5 Hz, 1H), 3.96-3.88 (m, 4H), 3.39-3.17 (m, 4H), 3.15-3.08 (m, 8H), 2.63-2.53 (m, 2H), 2.11-2.01 (m, 1H), 2.01-1.91 (m, 1H), 1.89-1.75 (m, 2H), 1.73-1.59 (m, 3H), 1.53-1.43 (m, 1H), 1.42-1.34 (m, 1H), 1.14-1.05 (m, 1H). (NH not detected)

4.6 Analytical separation of the 4 isomers of 8-(2,2-difluorocyclopropyl)-2,3,4,6,7,8-hexahydro-1H-[1,4]diazepino[6,7,1-ij]quinoline obtained in step 4.5

The Separation was Carried Out in Two Steps Via Method C:

Two peaks were separated on a Phenomenex LUX Amylose-2 Column (250×4.6 mm, 5 µm) (t$_R$ [min]=3.4, 4.1). The mobile phase consisted of 90% CO$_2$ and 10% modifier. As modifier, MeOH with 0.2 Vol % of aqueous ammonia solution (25%) was used. The first peak was then subjected to a second separation on a Daicel Chiralcel® OD-H column (100×4.6 mm, 5 µm) (t$_R$ [min]=4.1, 4.6). The mobile phase consisted of 95% CO$_2$ and 5% modifier. As modifier, MeOH with 0.2 Vol % of aqueous ammonia solution (25%) was used.

The second peak was separated on a Daicel Chiralpak® AD-H (100×4.6 mm, 5 µm) (t$_R$ [min]=3.7, 4.5). The mobile phase consisted of 95% CO$_2$ and 5% modifier. As modifier, MeOH with 0.2 Vol % of aqueous ammonia solution (25%) was used.

4.7 Preparative separation of the 4 isomers of 8-(2,2-difluorocyclopropyl)-2,3,4,6,7,8-hexahydro-1H-[1,4]diazepino[6,7,1-ij]quinoline obtained in step 4.5

The Separation of the 4 Isomers was Carried Out in Two Steps by UV-Detection at 214 nm:

Two peaks were separated on a Phenomenex LUX Amylose-2 Column (250×21.2 mm, 5 µm) (t$_R$ [min]=3.1, 3.8). The mobile phase consisted of 90% CO$_2$ and 10% modifier. As modifier, MeOH with 0.2 Vol % of aqueous ammonia solution (25%) was used. The first peak was then subjected to a second separation on a Daicel Chiralcel® OD-H column (250×20 mm, 5 µm) (t_R [min]=9.2, 10.1). The mobile phase consisted of 95% $CO_2$ and 5% modifier. As modifier, MeOH with 0.2 Vol % of aqueous ammonia solution (25%) was used.

The second peak was separated on a YMC CHIRAL Amylose-C column (250×20 mm, 5 µm) (t_R [min]=7.1, 8.2). The mobile phase consisted of 95% $CO_2$ and 5% modifier. As modifier, MeOH with 0.1 Vol % diethylamine was used.

Isomer 4.A of 8-(2,2-difluorocyclopropyl)-2,3,4,6,7, 8-hexahydro-1H-[1,4]diazepino[6,7,1-ij]quinolone (single enantiomer of the compound of example 4.5)

ESI-MS: m/z (%): 265.20 (100, [M+H]$^+$).
The retention time according to the analytical method described above is 4.1 min and according to the preparative method described above 9.2 min.

Isomer 4.B of 8-(2,2-difluorocyclopropyl)-2,3,4,6,7, 8-hexahydro-1H-[1,4]diazepino[6,7,1-ij]quinolone (single enantiomer of the compound of example 4.5)

ESI-MS: m/z (%): 265.20 (100, [M+H]$^+$).
The retention time according to the analytical method described above is 4.6 min and according to the preparative method described above 10.1 min.

Isomer 4.0 of 8-(2,2-difluorocyclopropyl)-2,3,4,6,7, 8-hexahydro-1H-[1,4]diazepino[6,7,1-ij]quinolone (single enantiomer of the compound of example 4.5)

ESI-MS: m/z (%): 265.20 (100, [M+H]$^+$).
The retention time according to the analytical method described above is 3.7 min and according to the preparative method described above method 7.1 min.

Isomer 4.D of 8-(2,2-difluorocyclopropyl)-2,3,4,6,7, 8-hexahydro-1H-[1,4]diazepino[6,7,1-ij]quinolone (single enantiomer of the compound of example 4.5)

ESI-MS: m/z (%): 265.20 (100, [M+H]$^+$).
The retention time according to the analytical method described above is 4.5 min and according to the preparative method described above 8.2 min.

Example 5

8-(Oxetan-3-yl)-2,3,4,6,7,8-hexahydro-1H-[1,4]diazepino[6,7,1-ij]quinoline (compound Ia.1 wherein $R^6$ is oxetan-3-yl and $R^{4a}$, $R^{4b}$, $R^{5a}$, $R^{5b}$ and $R^{7a}$ are hydrogen)

5.1 4-(Oxetan-3-yl)-3,4-dihydroquinolin-2(1H)-one

A mixture of 750 mg of oxetan-3-yl-acrylic acid ethyl ester (2.40 mmol, 1.00 eq), 658 mg of 2-aminophenyl boronic ester (4.80 mmol, 2.00 eq), 664 mg of potassium carbonate (4.80 mmol, 2.00 eq) and 54.8 mg of [RhOH (COD)]$_2$ (0.120 mmol, 0.05 eq) in 2% wt. TPGS-750-M solution in water (15 mL) was stirred vigorously at ambient temperature for the 48 h. Then the reaction mixture was extracted with ethyl acetate. The organic phase was dried over $MgSO_4$, filtered and reduced under vacuum. The crude product was purified by column chromatography on silica (eluent: 0-10% methanol in dichloromethane) to yield the title product (90%, 2.17 mmol).

ESI-MS: m/z (%): 204.10 (100, [M+H]$^+$).

5.2 4-(Oxetan-3-yl)-1,2,3,4-tetrahydroquinoline

To a solution of 882 mg of 4-(oxetan-3-yl)-3,4-dihydroquinolin-2(1H)-one (2.17 mmol, 1.00 eq) from step 5.1 in THF (20 ml) 6.51 mL of lithium aluminium hydride (1 M in THF, 6.51 mmol, 3.00 eq) was slowly added at 0° C. The mixture was stirred at 0° C. for 10 min and was then warmed up to room temperature and stirred for further 6 h at room temperature. Then the mixture was cooled to 0° C. and water (0.03 mL) was added followed by 10% aqueous NaOH (0.03 mL) and water (0.1 mL) again. The mixture was stirred at 0° C. for 1 h. Then $MgSO_4$ was added and the mixture was filtrated and the solvent was evaporated. The crude product was purified by column chromatography on silica (eluent: 0-10% methanol in dichloromethane) to yield the title product (13%, 0.301 mmol).

ESI-MS: m/z (%): 190.20 (100, [M+H]$^+$).

5.3 2-(4-(Oxetan-3-yl)-3,4-dihydroquinolin-1(2H)-yl)acetamide

A mixture of 57 mg of 4-(oxetan-3-yl)-1,2,3,4-tetrahydroquinoline (0.301 mmol, 1.00 eq) from step 5.2, 111 mg of 2-iodoacetamide (0.602 mmol, 2.00 eq) and 0.205 mL of DIPEA (1.20 mmol, 4.00 eq) in DMF (1 mL) was heated in a microwave at 100° C. for 16 h. Then NaOH (1M) was added and the mixture was extracted with dichloromethane. The organic phase was dried over $MgSO_4$ and reduced under vacuum. The crude product was purified by column chromatography on silica (eluent: 0-10% methanol in dichloromethane) to yield the title product (55%, 0.166 mmol).

ESI-MS: m/z (%): 247.20 (100, [M+H]$^+$).

5.4 2-(4-(Oxetan-3-yl)-3,4-dihydroquinolin-1(2H)-yl)ethanamine

To a solution of 41 mg of 2-(4-(oxetan-3-yl)-3,4-dihydroquinolin-1(2H)-yl)acetamide (0.166 mmol, 1.00 eq) from step 5.3 in THF (4 ml) 0.499 mL of lithium aluminium hydride (1 M in THF, 0.499 mmol, 3.00 eq) was slowly added at 0° C. The mixture was stirred at 0° C. for 10 min and was then warmed up to room temperature and stirred for further 6 h at room temperature. Then the mixture was cooled to 0° C. and water (0.03 mL) was added followed by 10% aqueous NaOH (0.03 mL) and water (0.1 mL) again. The mixture was stirred at 0° C. for 1 h. Then $MgSO_4$ was added and the mixture was filtrated and the solvent was evaporated. The crude product was purified by column chromatography on silica (eluent: 0-10% methanol in dichloromethane) to yield the title product (38%, 0.064 mmol).

ESI-MS: m/z (%): 233.20 (100, [M+H]$^+$).

5.5 8-(Oxetan-3-yl)-2,3,4,6,7,8-hexahydro-1H-[1,4]diazepino[6,7,1-ij]quinoline

A mixture of 86 mg of 2-(4-(oxetan-3-yl)-3,4-dihydroquinolin-1(2H)-yl)ethanamine (0.370 mmol, 1.00 eq) from step 5.4, formaldehyde (0.389 mmol, 1.05 eq) and TFA (0.407 mmol, 1.10 eq) in ethanol (3 mL) was stirred at ambient temperature for 2 h. Then NaOH (1M) was added and the mixture was extracted with dichloromethane. The organic phase was dried over $MgSO_4$ and reduced under vacuum. The crude product was purified by SFC to yield the title product (3.5%, 0.013 mmol).

ESI-MS: m/z (%): 245.30 (100, [M+H]$^+$).
$^1$H NMR (500 MHz, Methanol-d$_4$): δ 6.97 (d, J=7.3, 1.4 Hz, 1H), 6.79 (d, J=7.4 Hz, 1H), 6.70 (t, J=7.5 Hz, 1H), 4.90-4.80 (m, 1H), 4.79-4.70 (m, 2H), 4.68-4.60 (m, 1H), 3.79 (q, J=14.0 Hz, 2H), 3.36-3.27 (m, 2H), 3.27-3.17 (m, 2H), 3.20-3.06 (m, 3H), 3.05-2.92 (m, 2H), 1.94-1.84 (m, 1H), 1.67-1.57 (m, 1H).

Example 6

8-(Tetrahydro-2H-pyran-4-yl)-2,3,4,6,7,8-hexahydro-1H-[1,4]diazepino[6,7,1-ij]quinoline (compound Ia.1 wherein $R^6$ is tetrahydro-2H-pyran-4-yl and $R^{4a}$, $R^{4b}$, $R^{5a}$, $R^{5b}$ and $R^{7a}$ are hydrogen)

6.1 4-(Tetrahydro-2H-pyran-4-yl)-3,4-dihydroquinolin-2(1H)-one

A mixture of 100 mg of tetrahydropyran-4-yl-acrylic acid ethyl ester (0.588 mmol, 1.00 eq), 161 mg of 2-aminophenyl boronic ester (1.18 mmol, 2.00 eq), 162 mg of potassium carbonate (1.18 mmol, 2.00 eq) and 13.4 mg of [RhOH(COD)]$_2$ (0.029 mmol, 0.05 eq) in 2% wt. TPGS-750-M solution in water (3 mL) was stirred vigorously at ambient temperature for 48 h and then at 70° C. for further 20 h. The reaction mixture was extracted with ethyl acetate. The organic phase was dried over MgSO$_4$, filtrated and reduced under vacuum. The crude product was purified by column chromatography on silica (eluent: 0-20% methanol in dichloromethane) to yield the title product (67%, 0.395 mmol).

ESI-MS: m/z (%): 232.20 (100, [M+H]$^+$).

6.2 4-(Tetrahydro-2H-pyran-4-yl)-1,2,3,4-tetrahydroquinoline

To a solution of 91.4 mg of 4-(tetrahydro-2H-pyran-4-yl)-3,4-dihydroquinolin-2(1H)-one (0.395 mmol, 1.00 eq) from step 6.1 in THF (2 ml) was added 0.790 mL of borane tetrahydrofurane complex (2 M in THF, 1.58 mmol, 4.00 eq). The mixture was stirred at room temperature for 16 h and then heated in a microwave at 90° C. for 2 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over MgSO$_4$ and reduced under vacuum to yield the title product (44%, 0.173 mmol).

ESI-MS: m/z (%): 218.20 (100, [M+H]$^+$).

6.3 2-(4-(Tetrahydro-2H-pyran-4-yl)-3,4-dihydroquinolin-1(2H)-yl)acetamide

A mixture of 37.6 mg of 4-(tetrahydro-2H-pyran-4-yl)-1,2,3,4-tetrahydroquinoline (0.173 mmol, 1.00 eq) from step 6.2, 128 mg of 2-iodoacetamide (0.692 mmol, 4.00 eq) and 0.177 mL of DIPEA (1.04 mmol, 6.00 eq) in DMF (3 mL) was heated in a microwave at 120° C. for 8 h. Then NaOH (1M) was added and the mixture was extracted with dichloromethane. The organic phase was dried over MgSO$_4$ and reduced under vacuum. The crude product was purified by column chromatography on silica (eluent: 0-30% methanol in dichloromethane) to yield the title product.

ESI-MS: m/z (%): 275.20 (100, [M+H]$^+$).

6.4 2-(4-(Tetrahydro-2H-pyran-4-yl)-3,4-dihydroquinolin-1(2H)-yl)ethanamine

To a solution of 191 mg of 2-(4-(tetrahydro-2H-pyran-4-yl)-3,4-dihydroquinolin-1(2H)-yl)acetamide (0.696 mmol, 1.00 eq) from step 6.3 in THF (5 ml) was added 1.74 mL of borane tetrahydrofurane complex (2 M in THF, 3.48 mmol, 5.00 eq). The mixture was stirred at room temperature for 16 h and then heated in a microwave at 90° C. for 1 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over MgSO$_4$ and reduced under vacuum to yield the title product (76%, 0.529 mmol).

ESI-MS: m/z (%): 261.20 (100, [M+H]$^+$).

6.5 8-(Tetrahydro-2H-pyran-4-yl)-2,3,4,6,7,8-hexahydro-1H-[1,4]diazepino[6,7,1-ij]quinoline A mixture of 33.8 mg of 2-(4-(tetrahydro-2H-pyran-4-yl)-3,4-dihydroquinolin-1(2H)-yl)ethanamine (0.130 mmol, 1.00 eq) from step 6.4, formaldehyde (0.130 mmol, 1.00 eq) and TFA (0.143 mmol, 1.10 eq) in ethanol (2 mL) was stirred at ambient temperature for 48 h and then at 70° C. for further 4 h. The solvent was removed under vacuum. The residue was dissolved in DCM and washed with saturated aqueous sodium bicarbonate solution. The organic layer was dried over Na$_2$SO$_4$, filtrated and reduced under vacuum. The crude product was purified by column chromatography on silica (eluent: 0-30% methanol in dichloromethane) to yield the title compound (15%, 0.019 mmol).

ESI-MS: m/z (%): 273.20 (100, [M+H]$^+$).

$^1$H NMR (600 MHz, Methanol-d$_4$): δ 7.14 (td, J=7.4, 1.6 Hz, 2H), 6.85 (t, J=7.5 Hz, 1H), 4.29 (d, J=13.7 Hz, 1H), 4.17 (d, J=13.8 Hz, 1H), 4.01-3.91 (m, 2H), 3.63 (s, 1H), 3.50-3.45 (m, 1H), 3.43-3.30 (m, 4H), 3.26 (ddd, J=12.1, 10.4, 4.0 Hz, 1H), 2.66 (s, 1H), 2.63 (dt, J=7.9, 5.2 Hz, 1H), 2.09-2.01 (m, 1H), 1.89-1.82 (m, 1H), 1.82-1.74 (m, 1H), 1.61-1.55 (m, 1H), 1.55-1.49 (m, 2H), 1.39-1.27 (m, 1H). (NH not detected)

Example 7

8-(Tetrahydrofuran-3-yl)-2,3,4,6,7,8-hexahydro-1H-[1,4]diazepino[6,7,1-ij]quinoline (compound Ia.1 wherein $R^6$ is tetrahydrofuran-3-yl and $R^{4a}$, $R^{4b}$, $R^{5a}$, $R^{5b}$ and $R^{7a}$ are hydrogen)

7.1 4-(Tetrahydrofuran-3-yl)-3,4-dihydroquinolin-2(1H)-one

A mixture of 100 mg of tetrahydrofuran-3-yl-acrylic acid methyl ester (0.640 mmol, 1.00 eq), 175 mg of 2-aminophenyl boronic ester (1.28 mmol, 2.00 eq), 177 mg of potassium carbonate (1.28 mmol, 2.00 eq) and 14.6 mg of [RhOH(COD)]$_2$ (0.032 mmol, 0.05 eq) in 2% wt. TPGS-750-M solution in water (3 mL) was stirred vigorously at ambient temperature for the 48 h and then at 70° C. for further 6 h. The reaction mixture was extracted with ethyl acetate. The organic phase was dried over MgSO$_4$, filtrated and reduced under vacuum. The crude product was purified by column chromatography on silica (eluent: 0-30% methanol in dichloromethane) to yield the title product (81%, 0.516 mmol).

ESI-MS: m/z (%): 218.20 (100, [M+H]$^+$).

7.2 4-(Tetrahydrofuran-3-yl)-1,2,3,4-tetrahydroquinoline

To a solution of 112 mg of 4-(tetrahydrofuran-3-yl)-3,4-dihydroquinolin-2(1H)-one (0.516 mmol, 1.00 eq) from step 7.1 in THF (2 ml) was added 1.03 mL of borane tetrahydrofurane complex (2 M in THF, 2.06 mmol, 4.00 eq). The mixture was stirred at room temperature for 16 h and then heated in a microwave at 90° C. for 2 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over MgSO$_4$ and reduced under vacuum to yield the title product (69%, 0.358 mmol).

ESI-MS: m/z (%): 204.20 (100, [M+H]$^+$).

7.3 2-(4-(Tetrahydrofuran-3-yl)-3,4-dihydroquinolin-1(2H)-yl)acetamide

A mixture of 72.7 mg of 4-(tetrahydrofuran-3-yl)-1,2,3,4-tetrahydroquinoline (0.358 mmol, 1.00 eq) from step 7.2, 265 mg of 2-iodoacetamide (1.43 mmol, 4.00 eq) and 0.367 mL of DIPEA (1.43 mmol, 6.00 eq) in DMF (3 mL) was heated in a microwave at 120° C. for 8 h. Then NaOH (1M) was added and the mixture was extracted with dichloromethane. The organic phase was dried over $MgSO_4$ and reduced under vacuum. The crude product was purified by column chromatography on silica (eluent: 0-70% methanol in dichloromethane) to yield the title product.

ESI-MS: m/z (%): 261.20 (100, $[M+H]^+$).

7.4 2-(4-(Tetrahydrofuran-3-yl)-3,4-dihydroquinolin-1(2H)-yl)ethanamine

To a solution of 480 mg of 2-(4-(tetrahydrofuran-3-yl)-3,4-dihydroquinolin-1(2H)-yl)acetamide (1.84 mmol, 1.00 eq) from step 7.3 in THF (5 ml) was added 4.61 mL of borane tetrahydrofurane complex (2 M in THF, 9.22 mmol, 5.00 eq). The mixture was stirred at room temperature for 16 h and then heated in a microwave at 90° C. for 2 h. Then the reaction mixture was quenched with HCl (1 M) and the aqueous phase was extracted with ethyl acetate. The organic phase was extracted three times with HCl (1M) and to the aqueous phase was added NaOH (1M) until pH 10 and was then extracted with dichloromethane three times. The organic phase was dried over $MgSO_4$ and reduced under vacuum. The crude product was purified by column chromatography on silica (eluent: 0-70% methanol in dichloromethane) to yield the title product (12%, 0.215 mmol).

ESI-MS: m/z (%): 247.20 (100, $[M+H]^+$).

7.5 8-(Tetrahydrofuran-3-yl)-2,3,4,6,7,8-hexahydro-1H-[1,4]diazepino[6,7,1-ij]quinoline A mixture of 53.0 mg of 2-(4-(tetrahydrofuran-3-yl)-3,4-dihydroquinolin-1(2H)-yl)ethanamine (0.215 mmol, 1.00 eq) from step 7.4, formaldehyde (0.215 mmol, 1.00 eq) and TFA (0.237 mmol, 1.10 eq) in ethanol (2 mL) was stirred at ambient temperature for 84 h. Then the solvent was removed under vacuum. The residue was dissolved with DCM and washed with saturated aqueous sodium bicarbonate solution. The organic layer was dried over $Na_2SO_4$, filtrated and reduced under vacuum. The crude product was purified by preparative HPLC to yield the title compound (38%, 0.082 mmol).

ESI-MS: m/z (%): 259.20 (100, $[M+H]^+$).

$^1$H NMR of mixture of diastereomers (600 MHz, Methanol-$d_4$): δ 7.22-7.05 (m, 4H), 6.87-6.79 (m, 2H), 4.30 (d, J=13.9 Hz, 2H), 4.16 (dd, J=13.8, 4.4 Hz, 2H), 3.98-3.90 (m, 3H), 3.80-3.62 (m, 4H), 3.53-3.30 (m, 13H), 2.82-2.71 (m, 2H), 2.60-2.43 (m, 2H), 2.17-2.09 (m, 1H), 2.04-1.97 (m, 1H), 1.95-1.86 (m, 4H), 1.85-1.79 (m, 1H), 1.72-1.62 (m, 1H). (NH not detected)

Example 8

8-Cyclopropyl-10-(2-methoxyethyl)-2,3,4,6,7,8-hexahydro-1H-[1,4]diazepino[6,7,1-ij]quinoline (compound Ia.1 wherein $R^6$ is cyclopropyl, $R^{4a}$, $R^{4b}$, $R^{5a}$ and $R^{5b}$ are hydrogen, and $R^{7a}$ is 2-methoxyethyl)

8.1 tert-Butyl 8-cyclopropyl-3,4,7,8-tetrahydro-1H-[1,4]diazepino[6,7,1-ij]quinoline-2(6H)-carboxylate A solution of 980 mg of 8-cyclopropyl-2,3,4,6,7,8-hexahydro-1H-[1,4]diazepino[6,7,1-ij]quinoline (4.29 mmol, 1.00 eq) from example 1.6, 1.20 mL of triethylamine (8.58 mmol, 2.00 eq) and 937 mg of di-tert-butyl dicarbonate (4.29 mmol, 1.00 eq) in DCM (20 mL) was stirred 30 min at room temperature. Then the organic phase was extracted with water, dried over $MgSO_4$ and the solvent was evaporated to yield the title compound (100%, 4.29 mmol).

ESI-MS: m/z (%): 329.20 (100, $[M+H]^+$).

8.2 tert-Butyl 10-bromo-8-cyclopropyl-3,4,7,8-tetrahydro-1H-[1,4]diazepino[6,7,1-ij]quinoline-2(6H)-carboxylate A solution of 600 mg of tert-butyl 8-cyclopropyl-3,4,7,8-tetrahydro-1H-[1,4]diazepino[6,7,1-ij]quinoline-2(6H)-carboxylate (1.83 mmol, 1.00 eq) from step 8.1 in THF (20 mL) was cooled to 0° C. Then 325 mg N-bromosuccinimide (1.83 mmol, 1.00 eq) was added and the mixture was stirred for 30 min at 0° C. The solvent was evaporated to yield the title compound.

ESI-MS: m/z (%): 408.20 (100, $[M+H]^+$).

8.3 tert-Butyl 8-cyclopropyl-10-(2-methoxyethyl)-3,4,7,8-tetrahydro-1H-[1,4]diazepino[6,7,1-ij]quinoline-2(6H)-carboxylate Under an argon atmosphere a mixture of 100 mg of tert-butyl 10-bromo-8-cyclopropyl-3,4,7,8-tetrahydro-1H-[1,4]diazepino[6,7,1-ij]quinoline-2(6H)-carboxylate (0.245 mmol, 1.00 eq) from step 8.2, 40.7 mg of potassium trifluoro(2-methoxyethyl)borate (0.245 mmol, 1.00 eq), 240 mg of cesium carbonate (0.736 mmol, 3.00 eq), 2.04 mg of $Pd(OAc)_2$ (0.009 mmol, 0.04 eq) and 8.19 mg of X-Phos (0.017 mmol, 0.07 eq) in degassed THF (4 mL) and water (0.5 mL) was heated in a microwave at 120° C. for 20 h. Then the solvent was evaporated to yield the title compound.

ESI-MS: m/z (%): 387.30 (100, $[M+H]^+$).

8.4 8-Cyclopropyl-10-(2-methoxyethyl)-2,3,4,6,7,8-hexahydro-1H-[1,4]diazepino[6,7,1-ij]quinoline To a solution of 100 mg of tert-Butyl 8-cyclopropyl-10-(2-methoxyethyl)-3,4,7,8-tetrahydro-1H-[1,4]diazepino[6,7,1-ij]quinoline-2(6H)-carboxylate (0.259 mmol, 1.00 eq) in DCM (3 mL) was added 0.199 mL TFA (2.59 mmol, 10.0 eq) and the mixture was stirred for 18 h at room temperature and then at 70° C. for further 8 h. The solvent was evaporated and the crude product was purified via preparative HPLC to yield the title compound (3.8%, 0.010 mmol).

ESI-MS: m/z (%): 287.30 (100, $[M+H]^+$).

$^1$H NMR (500 MHz, Methanol-$d_4$): δ 7.36 (d, J=2.1 Hz, 1H), 7.03 (d, J=2.0 Hz, 1H), 4.20 (d, J=1.8 Hz, 2H), 3.57 (t, J=6.7 Hz, 2H), 3.48-3.40 (m, 1H), 3.35-3.25 (m, 5H), 3.32 (s, 3H), 2.78 (t, J=6.7 Hz, 2H), 2.09-2.01 (m, 1H), 2.01-1.93 (m, 1H), 1.88-1.78 (m, 1H), 1.29 (s, 1H), 0.92-0.79 (m, 1H), 0.74-0.66 (m, 1H), 0.55-0.43 (m, 2H), 0.29-0.20 (m, 1H).

Example 9

8-Cyclopropyl-10-(methoxymethyl)-2,3,4,6,7,8-hexahydro-1H-[1,4]diazepino[6,7,1-ij]quinoline (compound Ia.1 wherein $R^6$ is cyclopropyl, $R^{4a}$, $R^{4b}$, $R^{5a}$ and $R^{5b}$ are hydrogen, and $R^{7a}$ is methoxymethyl)

9.1 tert-butyl 8-cyclopropyl-10-(methoxymethyl)-3,4,7,8-tetrahydro-1H-[1,4]diazepino[6,7,1-ij]quinoline-2(6H)-carboxylate Under an argon atmosphere a mixture of 70 mg of tert-butyl 10-bromo-8-cyclopropyl-3,4,7,8-tetrahydro-1H-[1,4]diazepino[6,7,1-ij]quinoline-2(6H)-carboxylate (0.172 mmol, 1.00 eq) from step 8.2, 52.2 mg of potassium trifluoro(2-methoxymethyl)borate (0.344 mmol, 2.00 eq), 168 mg of cesium carbonate (0.516 mmol, 3.00 eq), 1.43 mg of $Pd(OAc)_2$ (0.006 mmol, 0.04 eq) and 5.73 mg of X-Phos (0.012 mmol, 0.07 eq) in degassed dioxane (4 mL) and water (0.5 mL) was heated in a microwave at 130° C. for 40 h.

Then the mixture was extracted with DCM and the organic phase was washed with water and dried over MgSO$_4$, filtrated and solvent was evaporated to yield the title compound.

ESI-MS: m/z (%): 373.30 (100, [M+H]$^+$).

9.2 8-cyclopropyl-10-(methoxymethyl)-2,3,4,6,7,8-hexahydro-1H-[1,4]diazepino[6,7,1-ij]quinoline To a solution of 51.6 mg of tert-butyl 8-cyclopropyl-10-(methoxymethyl)-3,4,7,8-tetrahydro-1H-[1,4]diazepino[6,7,1-ij]quinoline-2(6H)-carboxylate (0.139 mmol, 1.00 eq) from step 9.2 in DCM (3 mL) was added 0.107 mL of TFA (1.39 mmol, 10.0 eq) and the mixture was stirred for 48 h at room temperature. Then the solvent was evaporated and the crude product was purified via preparative HPLC to yield the title compound (2.2%, 0.003 mmol).

ESI-MS: m/z (%): 273.20 (100, [M+H]$^+$).

Example 10

8-Cyclopropyl-2,3,4,6,7,8-hexahydro-1H-[1,4]diazepino[6,7,1-ij]quinoline-10-carbonitrile (compound Ia.1 wherein R$^6$ is cyclopropyl, R$^{4a}$, R$^{4b}$, R$^{5a}$ and R$^{5b}$ are hydrogen, and R$^{7a}$ is cyano)

10.1 tert-Butyl 10-cyano-8-cyclopropyl-3,4,7,8-tetrahydro-1H-[1,4]diazepino[6,7,1-ij]quinoline-2(6H)-carboxylate Under an argon atmosphere a mixture of 30 mg of tert-butyl 10-bromo-8-cyclopropyl-3,4,7,8-tetrahydro-1H-[1,4]diazepino[6,7,1-ij]quinoline-2(6H)-carboxylate (0.074 mmol, 1.00 eq) from step 8.2, 38.9 mg of potassium hexacyanoferrate(II) trihydrate (0.092 mmol, 1.25 eq), 25.4 mg of potassium carbonate (0.184 mmol, 2.50 eq), 3.31 mg of Pd(OAc)$_2$ (0.015 mmol, 0.20 eq) and 14.04 mg of X-Phos (0.029 mmol, 0.40 eq) in degassed dioxane (2 mL) and water (2 mL) was heated in a microwave at 100° C. for 10 h. Then the mixture was extracted with DCM and the organic phase was washed with water and dried over MgSO$_4$, filtrated and the solvent was evaporated to yield the title compound.

ESI-MS: m/z (%): 354.30 (100, [M+H]$^+$).

10.2 8-Cyclopropyl-2,3,4,6,7,8-hexahydro-1H-[1,4]diazepino[6,7,1-ij]quinoline-10-carbonitrile To a solution of 33.6 mg of tert-butyl 10-cyano-8-cyclopropyl-3,4,7,8-tetrahydro-1H-[1,4]diazepino[6,7,1-ij]quinoline-2(6H)-carboxylate (0.095 mmol, 1.00 eq) from step 10.1 in DCM (10 mL) was added 0.073 mL of TFA (0.951 mmol, 10.0 eq) and the mixture was stirred for 18 h at room temperature and heated in a microwave for further 4 h at 50° C. and then at 70° C. for further 3 h. The solvent was evaporated and the crude product was purified via preparative HPLC to yield the title compound (10%, 0.009 mmol).

ESI-MS: m/z (%): 254.20 (100, [M+H]$^+$).

$^1$H NMR (600 MHz, Methanol-d$_4$): δ 7.66 (dd, J=2.1, 0.9 Hz, 1H), 7.43 (d, J=2.0 Hz, 1H), 4.34 (s, 2H), 3.70-3.61 (m, 2H), 3.56-3.51 (m, 1H), 3.48 (t, J=5.1 Hz, 2H), 3.41-3.36 (m, 1H), 2.08-2.03 (m, 1H), 2.02-1.98 (m, 1H), 1.91-1.83 (m, 1H), 0.91-0.82 (m, 1H), 0.76-0.69 (m, 1H), 0.61-0.54 (m, 1H), 0.48-0.40 (m, 1H), 0.31-0.24 (m, 1H). (NH not detected)

II. Biological Tests

Functional Activity

1. Human 5-HT$_{2C}$ Functional Assay

The functional activity of compounds of formula I was assayed by incubation with U2OS_HTR$_{2C}$_β-Arrestin cells (DiscoverX, 93-0289C3) to induce beta-arrestin2 recruitment to the 5-HT$_{2C}$ receptor. The agonist-induced recruitment and proximity of the receptor and beta-arrestin2 leads to complementation and formation of active β-galactosidase. The enzyme complementation results in enzyme activity, which is measured following the termination of the agonist incubation using DiscoveRx's detection reagent, which contains a chemiluminescent substrate which produces a high intensity signal. Cells were plated and a medium-change to a 1% serum containing medium was performed 24 h later. The next day, test compounds were added and incubated for 1.5 h before addition of detection reagent.

The response produced was measured and compared with the response produced by 10 [mu]M 5-HT or the maximal effect induced by 5-HT (defined as 100%) to which it was expressed as a percentage response (relative efficacy). Dose response curves were constructed using Graphpad Prism (Graph Software Inc.) or using in house adapted software using a 4 parameter dose response model with variable slope (fit=(Bottom+(Top-Bottom)/(1+10^((Log EC50-x)*HillSlope))res=(y-fit)). Results are compiled in the table below.

2. Human 5-HT$_{2A}$ Functional Assay

Functional activity on the 5-HT$_{2A}$ receptor was determined by testing the effect of the compounds I on calcium mobilisation in CHO-K1 cells, stably transfected with human 5-HT$_{2A}$ receptor. Cells were seeded into sterile black 384-well plates with clear bottom at 25,000 cells/well in a volume of 25 μl and grown for 5-6 hours at 37° C., in 5% CO$_2$ in tissue culture medium ("Ultra CHO" by LONZA), containing 1% dialysed FCS and 50 μg/ml gentamicin (Invitrogen). After this incubation, medium was replaced by a serum free version of the same tissue culture medium followed by incubation overnight at 37° C. and in 5% CO$_2$. Cells were then loaded with a fluorescent calcium-sensitive dye in the presence of 0.07% probenecid for an hour at 37° C., according to the manufacturer's protocol (Ca5-Assay Kit, Molecular Devices), followed by an additional 60 min incubation at room temperature. Serial compound dilutions (final concentrations of 10$^{-10}$ to 10$^{-5}$M, prepared in HBSS+ 50 mM HEPES) were first added to the cells alone ("first addition" to assess agonism on the 5-HT$_{2A}$ receptor), then after 8 min, serotonin was added to the same wells at a final concentration of 3×10$^{-8}$ M ("second addition" to see potential antagonistic effect) and the maximal calcium response was determined using a FLIPR® Tetra instrument (Molecular Devices) in each of the two steps. The relative efficacy of the compounds was calculated as a percentage of the maximal effect induced by serotonin alone (defined as 100%). To determine EC$_{50}$/IC$_{50}$ values, concentration-response curves were fitted using a four-parameter logistic equation (IDBS Biobook™). K$_b$ values were calculated from IC$_{50}$ values, according to Cheng & Prusoff.

3. Human 5-HT$_{2B}$ Functional Assay

Functional activity on the 5-HT$_{2B}$ receptor was determined by testing the effect of the compounds I on calcium mobilisation in CHO-FlpIn cells, stably transfected with human 5-HT$_{2B}$ receptor. Cells were seeded into sterile black 384-well plates with clear bottom at 30,000 cells/well in a volume of 25 μl and grown overnight at 37° C., in 5% CO$_2$ in tissue culture medium ("CHO-S-SFM II" by Invitrogen), containing 1% dialysed FCS and 50 μg/ml gentamicin (Invitrogen). On the next morning, medium was replaced by a serum free version of the same tissue culture medium for a further incubation for 4 hours at 37° C. and in 5% CO$_2$. Cells were then loaded with a fluorescent calcium-sensitive dye in the presence of 0.07% probenecid for an hour at 37° C., according to the manufacturer's protocol (Ca5-Assay Kit, Molecular Devices), followed by an additional 60 min incubation at room temperature. Serial compound dilutions (final concentrations of 10$^{-10}$ to 10$^{-5}$M, prepared in HBSS+ 50 mM HEPES) were first added to the cells alone ("first addition" to assess agonism on the 5-HT$_{2B}$ receptor), then after 8 min, serotonin was added to the same wells at a final concentration of $10^{-8}$ M ("second addition" to see potential antagonistic effect) and the maximal calcium response was determined using a FLIPR® Tetra instrument (Molecular Devices) in each of the two steps. The relative efficacy of the compounds was calculated as a percentage of the maximal effect induced by serotonin alone (defined as 100%). To determine EC$_{50}$/IC$_{50}$ values, concentration-response curves were fitted using a four-parameter logistic equation (IDBS Biobook™). K$_b$ values were calculated from IC$_{50}$ values, according to Cheng & Prusoff.

TABLE

| # | EC50 5-HT$_{2C}$[1] | % efficacy | EC50 5-HT$_{2A}$[2] | % efficacy | Selectivity[4] (based on agonism) | EC50 5-HT$_{2B}$[3] | Selectivity[5] (based on agonism) |
|---|---|---|---|---|---|---|---|
| 1 | +++ | 105 | + | 25 | 122 | * | antagonist |
| 1.A | +++ | 89 | * |  | antagonist[6] | * | antagonist |
| 1.B | +++ | 121 | ++ | 50 | 23 | * | antagonist |
| 2 | ++ | 54 | * |  | antagonist | * | antagonist |
| 3 | ++ | 88 | * |  | antagonist | * | full[7] |
| 4 | ++ | 88 | ++ | 19 | 6 | * | antagonist |
| 4.A | ++ | 85 | * |  | antagonist | * | full |
| 4.B | ++ | 99 | + | 33 | 18 | * | antagonist |
| 4.C | ++ | 80 | * |  | antagonist | * | antagonist |
| 4.D | ++ | 111 | ** | 24 | 45 | * | antagonist |
| 5 | + | 82 | * |  | antagonist | * | full |

[1]Potency (EC50 5-HT$_{2C}$) in functional assay
[2]Potency (EC50 5-HT$_{2A}$) in functional assay
[3]Potency (EC50 5-HT$_{2B}$) in functional assay
[4]EC50 5-HT$_{2A}$/EC50 5-HT$_{2C}$
[5]EC50 5-HT$_{2B}$/EC50 5-HT$_{2C}$
[6]"antagonist" indicates functional antagonism with no measurable agonistic effect
[7]"full" indicates no measurable agonistic effect at 10 μM (highest concentration in assay)
Potency (EC50):
* >10 nM
** 1 μM to 10 μM
+ from 200 nM to <1 μM
++ from 20 nM to <200 nM
+++ <20 nM

We claim:
1. A compound of the formula (I)

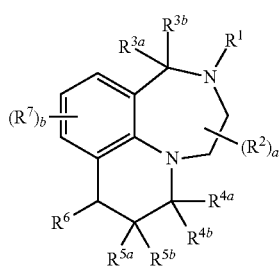

(I)

wherein
R$^1$ is selected from the group consisting of hydrogen, cyano, C$_1$-C$_6$-alkyl, fluorinated C$_1$-C$_6$-alkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy, fluorinated C$_1$-C$_6$-alkoxy, —C(=O)R$^9$, phenyl, phenyl-C$_1$-C$_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and SO$_2$ and optionally also 1 or 2 C=O and/or C=S groups as ring members, where the cyclic moieties in the three last-mentioned radicals may be substituted with one or more substituents R$^{10}$;

each R$^2$ is independently selected from the group consisting of cyano, nitro, C$_1$-C$_6$-alkyl, fluorinated C$_1$-C$_6$alkyl, C$_1$-C$_6$-hydroxyalkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy-C$_1$-C$_4$-alkyl, fluorinated C$_1$-C$_6$-alkoxy-C$_1$-C$_4$-alkyl, —CH$_2$NR$^{11a}$R$^{11b}$, —C(=O)R$^9$, phenyl, phenyl-C$_1$-C$_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, SO$_2$, C=O and C=S as ring members, where the cyclic moieties in the six last-mentioned radicals may be substituted with one or more substituents R$^{10}$;

R$^{3a}$ and R$^{3b}$, independently of each other, are selected from the group consisting of hydrogen, cyano, nitro, C$_1$-C$_6$-alkyl, fluorinated C$_1$-C$_6$-alkyl, C$_1$-C$_6$-hydroxyalkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy-C$_1$-C$_4$-alkyl, fluorinated C$_1$-C$_6$-alkoxy-C$_1$-C$_4$-alkyl, —CH$_2$NR$^{11a}$R$^{11b}$, —C(=O)R$^9$, phenyl, phenyl-C$_1$-C$_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, SO$_2$, C=O and C=S as ring members, where the cyclic moieties in the six last-mentioned radicals may be substituted with one or more substituents R$^{10}$;

R$^{4a}$ and R$^{4b}$, independently of each other, are selected from the group consisting of hydrogen, cyano, nitro, C$_1$-C$_6$-alkyl, fluorinated C$_1$-C$_6$-alkyl, C$_1$-C$_6$-hydroxyalkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy-C$_1$-C$_4$-alkyl, fluorinated C$_1$-C$_6$-alkoxy-C$_1$-C$_4$-alkyl, —CH$_2$NR$^{11a}$R$^{11b}$, —C(=O)R$^9$, phenyl, phenyl-C$_1$-

$C_2$-alkyl, and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; or $R^{4a}$ and $R^{4b}$ form together a group =O or =S;

$R^{5a}$ and $R^{5b}$, independently of each other, are selected from the group consisting of hydrogen, halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfonyl, $C_1$-$C_6$-alkylsulfonyl, fluorinated $C_1$-$C_6$-alkylsulfonyl, $-NR^{11a}$-$R^{11b}$, $-CH_2NR^{11a}R^{11b}$, $-NR^{11a}C(O)R^9$, $-C(=O)R^9$, $SO_2NR^{11a}R^{11b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{10}$; where $R^{5a}$ and $R^{5b}$ are not simultaneously hydroxy;

$R^6$ is a cyclic radica selected from the group consisting of $C_3$-$C_6$-cycloalkyl which may carry one or more radicals $R^8$; and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$, and optionally also 1 or 2 groups C=O and/or C=S, as ring members, where the heterocyclic ring may be substituted with one or more substituents $R^{10}$;

each $R^7$ is independently selected from the group consisting of halogen, cyano, nitro, hydroxy, $C_1$-$C_6$-alkyl, fluorinated $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkenyl, fluorinated $C_3$-$C_8$-cycloalkenyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $-NR^{11a}R^{11b}$, $-CH_2NR^{11a}R^{11b}$, $-NR^{11a}C(O)R^9$, $-C(=O)R^9$, $SO_2NR^{11a}R^{11b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals my be substituted with one or more substituents $R^{10}$;

each $R^8$ is independently selected from the group consisting of halogen, cyano, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $-NR^{11a}R^{11b}$, $-CH_2NR^{11a}R^{11b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{10}$; or two radicals $R^8$ bound to the same carbon atom may form together a group =O or =S;

each $R^9$ is independently selected from the group consisting of hydrogen, cyano, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $-NR^{11a}R^{11b}$, $-CH_2NR^{11a}R^{11b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{10}$;

each $R^{10}$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, fluorinated $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsuifonyl, $-COOH$, $-NR^{11a}R^{11b}$, $-CH_2NR^{11a}R^{11b}$, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, $SO_2NR^{11a}R^{11b}$, $C_1$-$C_6$-alkylcarbonyloxy and fluorinated $C_1$-$C_6$-alkylcarbonyloxy; or two radicals $R^{10}$, together with the atom(s) they are bound to, form a saturated, partially unsaturated or maximally unsaturated 3-, 4-, 5-, 6- or 7-membered carbocyclic or heterocyclic ring, where the heterocyclic ring contains 1, 2 or 3 heteroatoms or heteroatom groups independently selected from N, O, S, NO, SO, $SO_2$, C=O and C=S as ring members;

$R^{11a}$ and $R^{11b}$, independently of each other and independently of each occurrence, are selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, phenyl and benzyl, where the phenyl moieties in the two last-mentioned radicals may carry 1, 2 or 3 substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy; or, if $R^{11a}$ and $R^{11b}$ are hound to the same nitrogen atom, together with this nitrogen atom may form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, $SO$, $SO_2$, C=O and C=S as ring members, and where the ring may be substituted with one or more substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy;

a is 0, 1 or 2; and b is 0, 1, 2 or 3;

or an N-oxide, a tautorneric form, a stereoisomer or a pharmaceutically acceptable salt thereof.

2. The compound of claim 1, where $R^1$ is selected from hydrogen and $C_1$-$C_6$-alkyl.

3. The compound of claim 2, where $R^1$ is hydrogen.

4. The compound of claim 1, where $R^2$ is selected from $C_1$-$C_6$-alkyl, fluorinated $C_1$-$C_6$-alkyl, $C_1$-$C_6$-alkoxy-$C_1$-$C_4$-alkyl and fluorinated $C_1$-$C_6$-alkoxy-$C_1$-$C_4$-alkyl.

5. The compound of claim 4, where $R^2$ is selected from $C_1$-$C_6$-alkyl and fluorinated $C_1$-$C_6$-alkyl.

6. The compound of claim 5, where $R^2$ is selected from methyl and $CF_3$.

7. The compound of claim 1, where $R^{3a}$ and $R^{3b}$, independently of each other, are selected from hydrogen, cyano, nitro, $C_1$-$C_6$-alkyl and fluorinated $C_1$-$C_6$-alkyl.

8. The compound of claim 7, where $R^{3a}$ is selected from hydrogen, cyano, nitro, $C_1$-$C_6$-alkyl and fluorinated $C_1$-$C_6$-alkyl; and $R^{3b}$ is hydrogen.

9. The compound of claim 8, Where $R^{3a}$ is selected from hydrogen and methyl; and $R^{3b}$ is hydrogen.

10. The compound of claim 9, where $R^{3a}$ and $R^{3b}$ are hydrogen.

11. The compound of claim 1, where $R^{4a}$ and $R^{4b}$, independently of each other, are selected from hydrogen, $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl, or form together a group =O.

12. The compound of claim 11, where $R^{4a}$ and $R^{4b}$ are hydrogen.

13. The compound of claim 1, where $R^{5a}$ is selected from hydrogen, halogen, $C_1$-$C_6$-alkyl, fluorinated $C_1$-$C_6$-alkyl and $C_1$-$C_6$-alkoxy-$C_1$-$C_4$-alkyl; and $R^{5b}$ is hydrogen.

14. The compound of claim 13, where $R^{5a}$ is hydrogen or methyl; and $R^{5b}$ is hydrogen.

15. The compound of claim 1, where $R^6$ is $C_3$-$C_6$-cycloalkyl which may carry one or more radicals $R^8$.

16. The compound of claim 15, where each $R^8$ is independently selected from the group consisting of halogen, cyano, $C_1$-$C_6$-alkyl, fluorinated $C_1$-$C_6$-alkyl, $C_1$-$C_4$-alkoxy-$C_1$-$C_4$-alkyl and fluorinated $C_1$-$C_4$-alkoxy-$C_1$-$C_4$-alkyl.

17. The compound of claim 15, where $R^6$ is selected from cyclopropyl, cyclobutyl, cyclopentyl, cyclohexyl, 2,2-difluorocyclopropyl and 3,3-difluorocyclobutyl.

18. The compound of claim 17, where $R^6$ is 2,2-difluorocyclopropyl.

19. The compound of claim 17, where $R^6$ is selected from cyclopropyl and cyclobutyl.

20. The compound of claim 19, where $R^6$ is cyclopropyl.

21. The compound of claim 1, where $R^6$ is a 3-, 4-, 5-, 6- or 7-membered saturated heterocyclic ring containing 1, 2 or 3 heteroatoms or heteroatom groups independently selected from N, O, S, NO, SO and $SO_2$, and optionally also 1 or 2 groups C=O and/or C=S, as ring members, where the heterocyclic ring may be substituted with one or more substituents $R^{10}$.

22. The compound of claim 21, where $R^{10}$ is selected halogen, $C_1$-$C_6$-alkyl and fluorinated $C_1$-$C_6$-alkyl.

23. The compound of claim 22, where $R^{10}$ is methyl.

24. The compound of claim 21, where $R^6$ is a 3-, 4-, 5- or 6-membered saturated heterocyclic ring containing 1 or 2 heteroatoms or heteroatom groups independently selected from N, O, S, NO, SO and $SO_2$ as ring members, where the heterocyclic ring may be substituted with one or more substituents $R^{10}$.

25. The compound of claim 24, where $R^6$ is a 4-membered saturated heterocyclic ring containing 1 heteroatom or heteroatom group selected from N, O, S, NO, SO and $SO_2$ as ring member, where the heterocyclic ring may be substituted with one or more substituents $R^{10}$.

26. The compound of claim 25, where $R^6$ is a 4-membered saturated heterocyclic ring containing an oxygen atom as ring member, where the heterocyclic ring may be substituted with one or more substituents $R^{10}$.

27. The compound of claim 26, where $R^6$ is oxetan-3-yl, where the oxetan-3-yl may be substituted with one or more substituents $R^{10}$.

28. The compound of claim 24, where $R^6$ is a 5- or 6-membered saturated heterocyclic ring containing 1 heteroatom or heteroatom group selected from N, O, S, NO, SO and $SO_2$ as ring member, where the heterocyclic ring may be substituted with one or more substituents $R^{10}$.

29. The compound of claim 28, where $R^6$ is a 5- or 6-membered saturated heterocyclic ring containing an oxygen atom as ring member, where the heterocyclic ring may be substituted with one or more substituents $R^{10}$.

30. The compound of claim 29, where $R^6$ is tetrahydrofuran-3-yl or tetrahydropyran-4-yl, where the terahydrofuran-3-yl and tetrahydropyran-4-yl may be substituted with one or more substituents $R^{10}$.

31. The compound of claim 1, where each $R^7$ is independently selected from halogen, cyano, nitro, hydroxy, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy and fluorinated $C_1$-$C_6$-alkoxy.

32. The compound of claim 31, where each $R^7$ is independently selected from halogen, $C_1$-$C_4$-alkyl, fluorinated $C_1$-$C_4$-alkyl, $C_1$-$C_4$-alkoxy and fluorinated $C_1$-$C_4$-alkoxy.

33. The compound of claim 32, where $R^7$ is fluoro.

34. The compound of claim 1, where each $R^7$ is independently selected from cyano and $C_1$-$C_4$-alkoxy-$C_1$-$C_4$-alkyl.

35. The compound of claim 1, where a is 0 or 1.

36. The compound of claim 35, where when a is 1, $R^2$ is bound in the beta position relative to the nitrogen ring atom carrying $R^1$.

37. The compound of claim 1, where b is 0 or 1.

38. The compound of claim 1, wherein the compound is a compound of formula (I.1)

(I.1)

wherein a is 0 or 1.

39. The compound of claim 38, wherein the compound is a compound of formula (I.1.1)

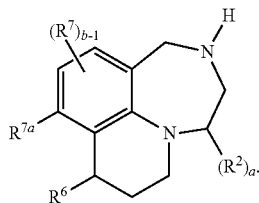

(I.1.1)

wherein
$R^{7a}$ is hydrogen, chloro, fluoro or methyl; and
a is 0 or 1.

40. A pharmaceutical composition comprising a therapeutically effective amount of a compound of claim 1, or an N-oxide, a tautomeric form, a stereoisomer or a pharmaceutically acceptable salt thereof, in combination with at least one pharmaceutically acceptable carrier and/or auxiliary substance.

41. A method for modulating 5-hydroxytryptamine$_{2C}$ receptor activity in a subject, which method comprises administering to a subject in need thereof a compound of claim 1, or an N-oxide, a tautomeric form, a stereoisomer or a pharmaceutically acceptable salt thereof.

42. The method of claim 41, wherein the subject suffers from a disorder selected from the group consisting of diabetes, damage of the central nervous system, an ocular hypertension, an eating disorder, a cardiovascular disorder, a gastrointestinal disorder and a disorder of the central nervous system.

43. The method of claim 41, wherein the subject suffers from a disorder selected from the group consisting of bipolar disorder, depression, anxiety, post-traumatic syndrome, psychosis, schizophrenia, memory loss, dementia of aging, Alzheimer's disease, social phobia, attention deficit hyperactivity disorder, autism, mutism, disruptive behavior disorder, impulse control disorder, borderline personality disorder, obsessive compulsive disorder, migraine, raised intracranial pressure, epilepsy, alcohol abuse, cocaine abuse, tobacco abuse, smoking cessation, sexual dysfunction in males, erectile dysfunction in males, sexual dysfunction in females, premenstrual syndrome, late luteal phase syndrome, chronic fatigue syndrome, chronic fatigue syndrome, psoriasis, Parkinson's disease, psychosis in Parkinson's disease, Lewy body dementia, spinal cord injury, trauma, stroke, pain, bladder dysfunction, urinary incontinence, encephalitis, meningitis, obesity, bulimia, weight loss, anorexia nervosa, ocular hypertension, diabetes insipidus, diabetes mellitus, type I diabetes, type II diabetes, type III diabetes, diabetes secondary to pancreatic diseases, diabetes related to steroid use, hyperglycemia, insulin resistance, an adjustment disorder, an organic mental disorder, an eating disorder, a diabetes complication, a mood episode, a cognitive deficit of schizophrenia, a neuropsychiatric symptom in Alzheimer's disease, a neuropsychiatric symptom in Lewy body dementia, a neuropsychiatric symptom in Parkinson's disease, a behavioral disorder associated with dementia, a panic disorder, a mental disorder in childhood, a seizure disorder, a substance use disorder, a sleep disorder, a cardiovascular disorder and a gastrointestinal disorder.

44. The method of claim 41, wherein the subject suffers from a disorder selected from the group consisting of bipolar disorder, depression, schizophrenia, obesity, a substance use disorder, a neuropsychiatric symptom in Alzheimer's disease and a neuropsychiatric symptom in Parkinson's disease.

45. A method for producing a compound of formula (I) according to claim 1, wherein the compound is represented by formula (I'):

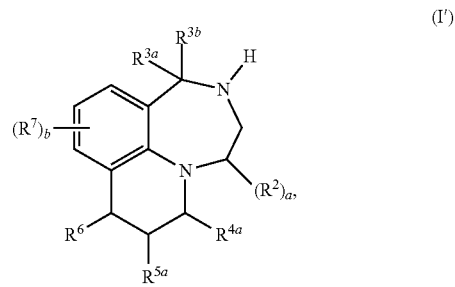

(I')

wherein a, b, $R^2$, $R^{3a}$, $R^{3b}$, $R^{4a}$, $R^{5a}$, $R^6$ and $R^7$ are as defined in claim 1,
comprising the following steps:
(i) reacting a compound of formula 1,

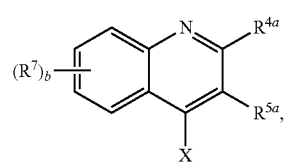

1 wherein X is Cl, Br, I or $OS(O)_2CF_3$, and b, $R^{4a}$, $R^{5a}$, $R^6$ and $R^7$ are as defined in claim 1, with a compound, $R_6$—$B(OH)_2$ or $K^+(R^6$—$BF_3)^-$, wherein $R^6$ is as defined in claim 1,
in the presence of a palladium catalyst, to provide a compound of formula 2,

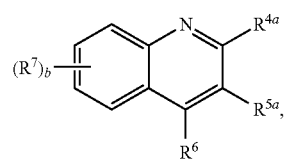

2 wherein b, $R^{4a}$, $R^{5a}$, $R^6$ and $R^7$ are as defined in claim 1;
(ii) reacting the compound of formula 2 above with benzyl bromide, to provide a compound of formula 3,

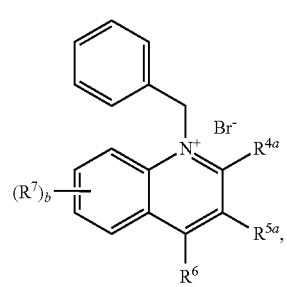

3 wherein b, $R^{4a}$, $R^{5a}$, $R^6$ and $R^7$ are as defined in claim 1;

(iii) reducing the compound of formula 3 above, to provide a compound of formula 4,

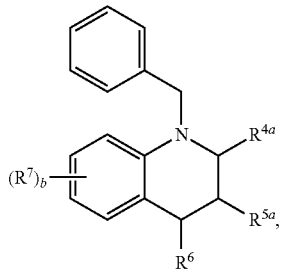

4 wherein b, $R^{4a}$, $R^{5a}$, $R^6$ and $R^7$ are as defined in claim 1;

(iv) deprotecting the compound of formula 4 above, to provide a compound of formula 5,

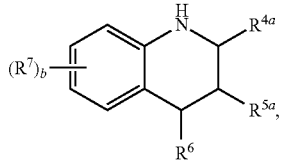

5 wherein b, $R^{4a}$, $R^{5a}$, $R^6$ and $R^7$ are as defined in claim 1;

(v) reacting the compound of formula 5 above with a compound of formula 6,

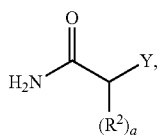

6 wherein Y is Cl, Br or I, and a and $R^2$ are as defined in claim 1, to provide a compound of formula 7,

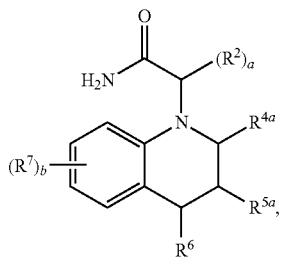

7 wherein a, b, $R^2$, $R^{4a}$, $R^{5a}$, $R^6$ and $R^7$ are as defined in claim 1;

(vi) reducing the carbonyl group of the compound of formula 7 above, to provide a compound of formula 8,

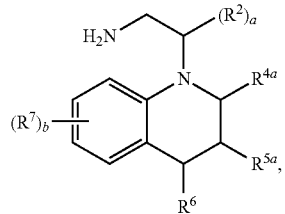

8 wherein a, b, $R^2$, $R^{4a}$, $R^{5a}$, $R^6$ and $R^7$ are as defined in claim 1; and (vii) cyclizing the compound of formula 8 above with a compound of formula 9,

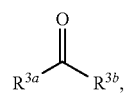

9 wherein $R^{3a}$ and $R^{3b}$ are as defined in claim 1, with the exception of $NO_2$ and CN, in the presence of a strong acid, to provide a compound of formula (I'),

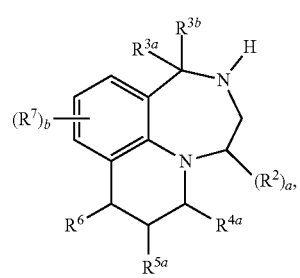

(I')

wherein a, b, $R^2$, $R^{3a}$, $R^{3b}$, $R^{4a}$, $R^{5a}$, $R^6$ and $R^7$ are as defined in claim 1.

46. A method for producing a compound of formula (I) according to claim 1, wherein the compound is represented by formula (I'):

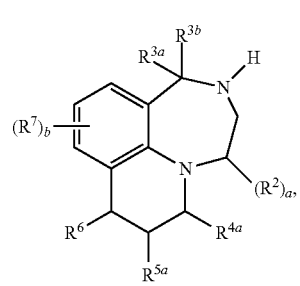

(I')

wherein a, b, $R^2$, $R^{3a}$, $R^{3b}$, $R^{4a}$, $R^{5a}$, $R^6$ and $R^7$ are as defined in claim 1, comprising the following steps:

(i) reacting a compound of formula 1,

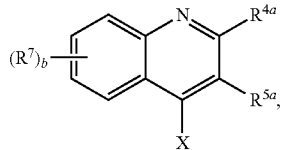

1 wherein X is Cl, Br, I or $OS(O)_2CF_3$, and b, $R^{4a}$, $R^{5a}$, $R^6$ and $R^7$ are as defined in claim 1, with a compound, $R_6-B(OH)_2$ or $K^+(R^6-BF_3)^-$, wherein $R^6$ is as defined in claim 1, in the presence of a palladium catalyst, to provide a compound of formula 2,

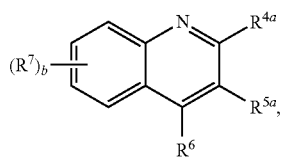

2 wherein b, $R^{4a}$, $R^{5a}$, $R^6$ and $R^7$ are as defined in claim 1;

(ii) reacting the compound of formula 2 above with a compound of formula 6,

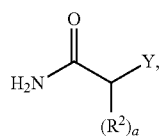

6 wherein Y is Cl, Br or I, and a and $R^2$ are as defined in claim 1, to provide a compound of formula 10,

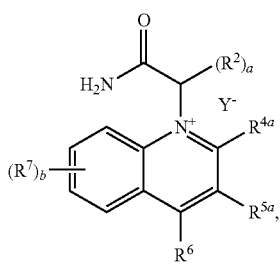

10 wherein Y is Cl, Br or I, and a, b, $R^2$, $R^{4a}$, $R^{5a}$, $R^6$ and $R^7$ are as defined in claim 1;

(iii) reducing the compound of formula 10 above, to provide a compound of formula 7,

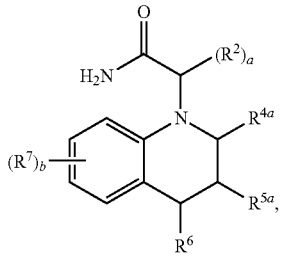

7 wherein a, b, $R^2$, $R^{4a}$, $R^{5a}$, $R^6$ and $R^7$ are as defined in claim 1;

(iv) reducing the carbonyl group of the compound of formula 7 above, to provide a compound of formula 8,

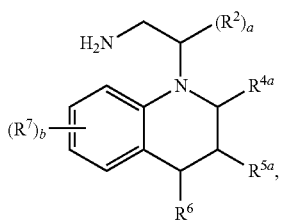

8 wherein a, b, $R^2$, $R^{4a}$, $R^{5a}$, $R^6$ and $R^7$ are as defined in claim 1; and (v) cyclizing the compound of formula 8 above with a compound of formula 9,

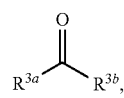

9 wherein $R^{3a}$ and $R^{3b}$ are as defined in claim 1, with the exception of $NO_2$ and CN, in the presence of a strong acid, to provide a compound of formula (I'),

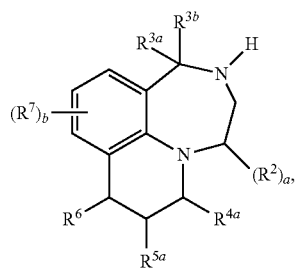

(I')

wherein a, b, $R^2$, $R^{3a}$, $R^{3b}$, $R^{4a}$, $R^{5a}$, $R^6$ and $R^7$ are as defined in claim 1.

47. A method for producing a compound of formula (I) according to claim 1, wherein the compound is represented by formula (I"):

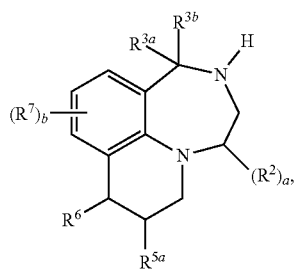

wherein a, b, $R^2$, $R^{3a}$, $R^{3b}$, $R^{5a}$, $R^6$ and $R^7$ are as defined in claim 1,
comprising the following steps:
(i) reacting a compound of formula 11,

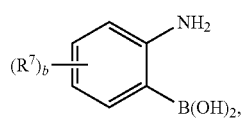

wherein b and $R^7$ are as defined in claim 1,
with a compound of formula 12,

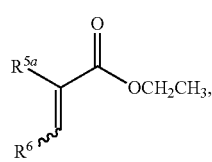

wherein $R^{5a}$ and $R^6$ are as defined in claim 1,
in the presence of a rhodium catalyst, to provide a compound of formula 13,

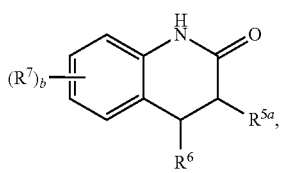

wherein b, $R^{5a}$, $R^6$ and $R^7$ are as defined in claim 1;
(ii) reducing the carbonyl group of the compound of formula 13 above, to provide a compound of formula 14,

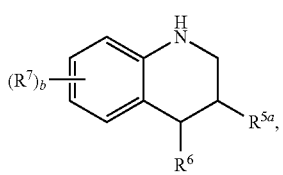

wherein b, $R^{5a}$, $R^6$ and $R^7$ are as defined in claim 1;

(iii) reacting the compound of formula 14 above with a compound of formula 6,

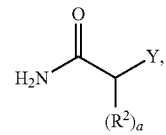

wherein Y is Cl, Br or I, and a and $R^2$ are as defined in claim 1,
to provide a compound of formula 15,

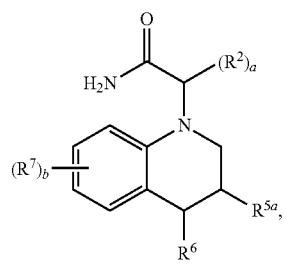

wherein a, b, $R^2$, $R^{5a}$, $R^6$ and $R^7$ are as defined in claim 1;
(iv) reducing the carbonyl group of the compound of formula 15 above, to provide a compound of formula 16,

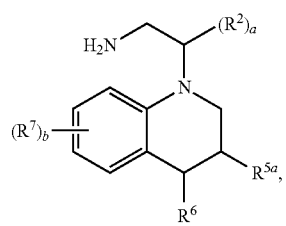

wherein a, b, $R^2$, $R^{5a}$, $R^6$ and $R^7$ are as defined in claim 1; and
(v) cyclizing the compound of formula 16 above with a compound of formula 9,

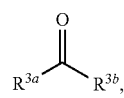

wherein $R^{3a}$ and $R^{3b}$ are as defined in claim 1, with the exception of $NO_2$ and CN,
in the presence of a strong acid, to provide a compound of formula (I"),

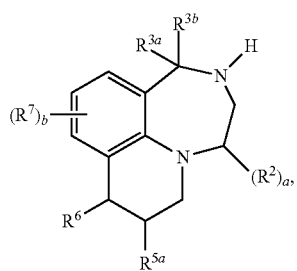

(I″)

wherein a, b, $R^2$, $R^{3a}$, $R^{3b}$, $R^{5a}$, $R^6$ and $R^7$ are as defined in claim 1.

48. A compound selected from the group consisting of:
8-cyclopropyl-2,3,4,6,7,8-hexahydro-1H-[1,4]diazepino[6,7,1-ij]quinoline-10-carbonitrile;
8-cyclopropyl-10-(2-methoxyethyl)-2,3,4,6,7,8-hexahydro-1H-[1,4]diazepino[6,7,1-ij]quinoline;
8-cyclopropyl-10-(methoxymethyl)-2,3,4,6,7,8-hexahydro-1H-[1,4]diazepino[6,7,1-ij]quinoline;
8-cyclopropyl-2,3,4,6,7,8-hexahydro-1H-[1,4]diazepino[6,7,1-ij]quinoline;
(R)-8-cyclopropyl-2,3,4,6,7,8-hexahydro-1H-[1,4]diazepino[6,7,1-ij]quinoline;
(S)-8-cyclopropyl-2,3,4,6,7,8-hexahydro-1H-[1,4]diazepino[6,7,1-ij]quinoline;
8-(2,2-difluorocyclopropyl)-2,3,4,6,7,8-hexahydro-1H-[1,4]diazepino[6,7,1-ij]quinoline;
8-cyclobutyl-2,3,4,6,7,8-hexahydro-1H-[1,4]diazepino[6,7,1-ij]quinoline;
(R)-8-cyclobutyl-2,3,4,6,7,8-hexahydro-1H-[1,4]diazepino[6,7,1-ij]quinoline;
(S)-8-cyclobutyl-2,3,4,6,7,8-hexahydro-1H-[1,4]diazepino[6,7,1-ij]quinoline;
8-(oxetan-3-yl)-2,3,4,6,7,8-hexahydro-1H-[1,4]diazepino[6,7,1-ij]quinoline;
8-(3-methyloxetan-3-yl)-2,3,4,6,7,8-hexahydro-1H-[1,4]diazepino[6,7,1-ij]quinoline;
8-(tetrahydro-2H-pyran-4-yl)-2,3,4,6,7,8-hexahydro-1H-[1,4]diazepino[6,7,1-ij]quinoline; and
8-(tetrahydrofuran-3-yl)-2,3,4,6,7,8-hexahydro-1H-[1,4]diazepino[6,7,1-ij]quinoline;

or a stereoisomer or a pharmaceutically acceptable salt thereof.

* * * * *